US008545248B2

(12) United States Patent
Davey et al.

(10) Patent No.: US 8,545,248 B2
(45) Date of Patent: Oct. 1, 2013

(54) SYSTEM TO CONTROL FLUID FLOW BASED ON A LEAK DETECTED BY A SENSOR

(75) Inventors: Melville Davey, Guilford, CT (US); George Roth, Fairfield, CT (US); David Marran, Durham, CT (US); William Mileski, Ledyard, CT (US); John Nobile, Fairfield, CT (US)

(73) Assignee: Life Technologies Corporation, Carlsbad, CA (US)

( * ) Notice: Subject to any disclaimer, the term of this patent is extended or adjusted under 35 U.S.C. 154(b) by 0 days.

(21) Appl. No.: 13/340,484

(22) Filed: Dec. 29, 2011

(65) Prior Publication Data
US 2012/0143531 A1 Jun. 7, 2012

Related U.S. Application Data

(63) Continuation-in-part of application No. 12/986,963, filed on Jan. 7, 2011, now Pat. No. 8,398,418.

(60) Provisional application No. 61/293,048, filed on Jan. 7, 2010, provisional application No. 61/374,602, filed on Aug. 17, 2010, provisional application No. 61/428,733, filed on Dec. 30, 2010.

(51) Int. Cl.
*H01R 13/52* (2006.01)
(52) U.S. Cl.
USPC .......................................... 439/271
(58) Field of Classification Search
USPC ......... 439/271–274, 587; 702/51; 73/40.5 R
See application file for complete search history.

(56) References Cited

U.S. PATENT DOCUMENTS

| 5,571,395 | A | 11/1996 | Park et al. |
| 6,802,720 | B2 | 10/2004 | Weiss et al. |
| 6,854,985 | B1 | 2/2005 | Weiss |
| 6,896,778 | B2 * | 5/2005 | Lauks .......................... 204/400 |
| 7,037,128 | B2 * | 5/2006 | Yaworski et al. ............. 439/276 |
| 7,059,874 | B2 | 6/2006 | Weiss |
| 7,077,659 | B2 | 7/2006 | Weiss et al. |
| 7,223,105 | B2 | 5/2007 | Weiss et al. |
| 7,249,954 | B2 | 7/2007 | Weiss |
| 7,520,761 | B2 | 4/2009 | Weiss |
| 2003/0181071 | A1 | 9/2003 | Weiss et al. |
| 2003/0224633 | A1 | 12/2003 | Weiss |

(Continued)

FOREIGN PATENT DOCUMENTS

| AU | 2003247705 | 2/2005 |
| JP | 08-313479 | 11/1996 |

(Continued)

OTHER PUBLICATIONS

PCT/US2011/020590 International Search Resort Mailed Sep. 15, 2011.

(Continued)

*Primary Examiner* — Chandrika Prasad

(57) ABSTRACT

A system including a communication interface to communicatively couple to a sensor cartridge, a fluidic subsystem to exchange a reagent solution with the sensor cartridge, and a computational circuitry communicatively coupled to the communication interface and the fluidic subsystem. The computation circuitry is to monitor a sensor signal of a sensor of the sensor cartridge, detect a leak based on the sensor signal, and control fluid flow of the fluidic subsystem in response to detecting.

21 Claims, 29 Drawing Sheets

(56) References Cited

U.S. PATENT DOCUMENTS

| | | |
|---|---|---|
| 2004/0127071 A1 | 7/2004 | Weiss et al. |
| 2005/0101167 A1 | 5/2005 | Weiss et al. |
| 2007/0015375 A1 | 1/2007 | Weiss |
| 2008/0139020 A1 | 6/2008 | Weiss |
| 2009/0215296 A1* | 8/2009 | Chambers .................... 439/271 |
| 2010/0248284 A1 | 9/2010 | Chen et al. |

FOREIGN PATENT DOCUMENTS

| | | |
|---|---|---|
| JP | 2948049 | 9/1999 |
| JP | 2003254951 | 9/2003 |
| JP | 2009524045 | 6/2009 |
| KR | 19970010981 | 7/1997 |
| TW | 200827886 | 7/2008 |
| WO | 2005013427 | 2/2005 |
| WO | 2008011245 | 1/2008 |

OTHER PUBLICATIONS

PCT/US2011/020590 Written Opinion Mailed Sep. 15, 2011.

PCT/US2007/071984 International Search Report mailed Mar. 27, 2008.

PCT/US2011/020590 International Preliminary Report on Patentability mailed Jul. 10, 2012.

* cited by examiner

SYSTEM TO CONTROL FLUID FLOW BASED ON A LEAK DETECTED BY A SENSOR

CROSS-REFERENCE TO RELATED APPLICATION(S)

This application is a continuation-in-part of U.S. patent application Ser. No. 12/986,963, filed Jan. 7, 2011, which claims benefit of U.S. Provisional Application No. 61/293,048, filed Jan. 7, 2010 and claims benefit of U.S. Provisional Application No. 61/374,602, filed Aug. 17, 2010. This application also claims the benefit of U.S. Provisional Application No. 61/428,733 filed Dec. 30, 2010. Each of the above applications is incorporated herein by reference in its entirety.

FIELD OF THE DISCLOSURE

This disclosure, in general, relates to systems and methods for control of a measurement system.

BACKGROUND

Electrochemical detection is attractive because it provides high sensitivity, small dimensions, low cost, fast response, and compatibility with microfabrication technologies. These characteristics have led to the development of a variety of sensors based on amperometric, potentiometric or impedimetric signals and their assembly into arrays for chemical, biochemical and cellular applications. In particular, several of these developments involve the use of large-scale arrays of electrochemical sensors for monitoring multiple reaction steps on a large plurality of analytes confined to such an array. Typically in such systems, analytes are randomly distributed among an array of confinement regions, such as microwells or reaction chambers, and reagents are delivered to such regions by a fluidics system that directs flows of reagents through a flow cell containing the sensor array. Microwells in which reactions take place, as well as empty wells where no reactions take place, may be monitored by one or more electronic sensors associated with each of the microwells.

Such systems are subject to a host of interrelated phenomena that make highly sensitive measurements challenging, particularly under low signal conditions. Such phenomena include unstable reference voltage for the electrical sensors, lack of knowledge as to which confinement regions contain analytes, variability in the amount of reagents delivered by a flow stream to analytes confined to different regions of an array, potential mixing of successively delivered reagents, changes in instrument temperature, fluid leaks that may affect fluid potential, extraneous electrical interference, e.g. 60 Hz noise, cell phones, or the like, all of which may affect the quality of signals collected. In addition, "decoding" signals and relating them to identification and quantification of analytes subject to interrogation by the electrochemical detection system presents challenges in terms of throughput, precision, and accuracy.

In view of the above, it would be advantageous to have available a system for carrying out multi-reagent electrochemical reactions in parallel on a large number of analytes which overcame the deficiencies of current approaches.

SUMMARY

In a first aspect, a system includes a communication interface to communicatively couple to a sensor cartridge, a fluidic subsystem to exchange a reagent solution with the sensor cartridge, and a computational circuitry communicatively coupled to the communication interface and the fluidic subsystem. The computation circuitry is to monitor a sensor signal of a sensor of the sensor cartridge, detect a leak based on the sensor signal, and control fluid flow of the fluidic subsystem in response to detecting.

In a second aspect, a method of controlling a system includes establishing communicative coupling between a communication interface and a sensor cartridge, establishing fluid communication between a fluidic subsystem and a sensor cartridge, monitoring a sensor signal of the sensor cartridge via the communication interface, detecting a leak based on a characteristic of the sensor signal, and controlling fluid flow of the fluidic subsystem in response to detecting the leak.

In a third aspect, a computer readable medium includes non-transitory computer operable instructions operable by a computational circuitry to perform a method comprising monitoring a sensor signal of a sensor cartridge via a communication interface. The sensor cartridge is communicatively coupled to the communication interface and in fluid communication with a fluid subsystem. The method further includes detecting a leak based on a characteristic of the sensor signal and controlling fluid flow of the fluidic subsystem in response to detecting the leak.

These above-characterized aspects, as well as other aspects, of the present teaching are exemplified in a number of illustrated implementations and applications, some of which are shown in the figures and characterized in the claims section that follows. However, the above summary is not intended to describe each illustrated embodiment or every implementation of the present teaching.

BRIEF DESCRIPTION OF THE DRAWINGS

The present disclosure may be better understood, and its numerous features and advantages made apparent to those skilled in the art by referencing the accompanying drawings.

The use of the same reference symbols in different drawings indicates similar or identical items.

DETAILED DESCRIPTION

Figure 1A:
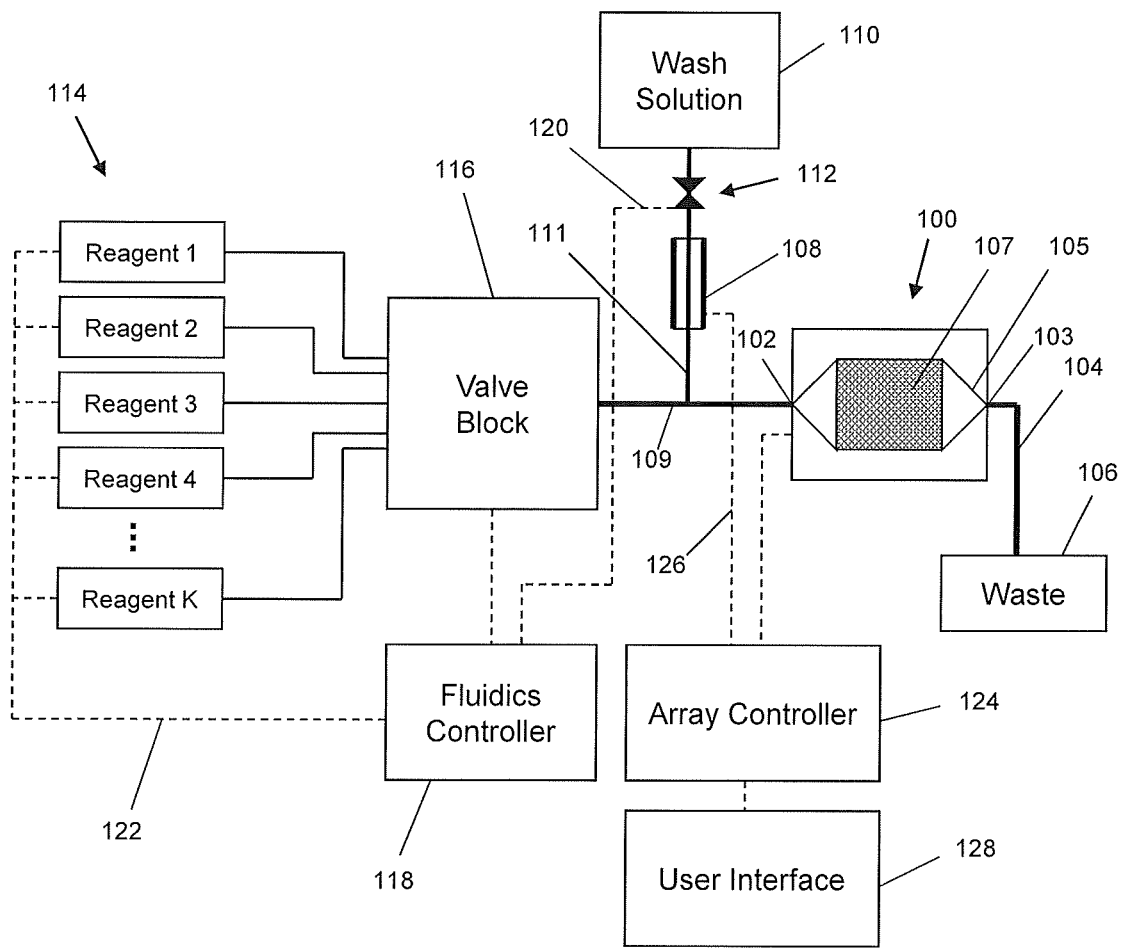
FIG. 1A illustrates components of one embodiment of the apparatus of the present teaching.

While the present teaching is amenable to various modifications and alternative forms, specifics thereof have been shown by way of example in the drawings and will be described in detail. It should be understood, however, that the intention is not to limit the present teaching to the particular embodiments described. On the contrary, the intention is to cover all modifications, equivalents, and alternatives falling within the spirit and scope of the present teaching. For example, the microelectronics portion of the apparatus and array is implemented in CMOS technology for purposes of illustration. It should be appreciated, however, that the disclosure is not intended to be limiting in this respect, as other semiconductor-based technologies may be utilized to implement various aspects of the microelectronics portion of the systems discussed herein.

In one aspect, the present teaching is directed to apparatus and methods for carrying out and monitoring a plurality of multi-step reactions with electronic sensors. The multi-step reactions may be cyclic, such as in DNA sequencing reactions, DNA synthesis reactions, or the like, where repeated cycles of one or more steps are carried out, or they may be non-cyclic, such as in multi-component labeling reactions, as for example, in a sandwich assay using enzymatic labels. Multi-step reactions may also result from the presence of a biological material, such as living cells or tissue sample, where responses, e.g. the presence or absence of metabolites, are detected in response to a series of reagent exposures, which may be drug candidate molecules, or the like. Preferably, electronic sensors of the present teaching are integrated into a sensor array suitable for sensing individual reactions taking place on or adjacent to a surface of the array. In one embodiment, an array of reaction confinement regions is integral with such a sensor array. An array of reaction confinement regions may take the form of a microwell array or a reaction chamber array made by conventional micro- or nanofabrication techniques, for example, as described in Rothberg et al, U.S. patent publication US2009/0127589 and Rothberg et al, U.K. patent application GB24611127. In one embodiment, each microwell or reaction chamber in such an array has at least one sensor that is in a sensing relationship so that one or more characteristics of a reaction in the microwell or reaction chamber can be detected or measured. Typically electronic sensors of the present teaching measure directly or indirectly (for example, by the use of a binding compound or label) reaction byproducts including, but not limited to, chemical species resulting from a reaction or physical changes caused by a reaction, such as increases or decreases in temperature, e.g. as disclosed in Rothberg et al (U.S. and U.K. patent publications cited above). Preferably, electronic sensors of the present teaching convert changes in the presence, concentration or amounts of reaction byproducts into an output signal, which may be a change in a voltage level or a current level which, in turn, may be processed to extract information about a reaction. Electronic sensors of the array, or a subset of such sensors, may also be used to monitor the presence or concentration of reactants, indicator molecules, or other reagents, such as reagents for identifying microwells containing analytes (described more fully below). In a preferred embodiment, sensors of the array comprise at least one chemically sensitive field effect transistor that is configured to generate at least one output signal related to a property of a chemical reaction in proximity thereof. Such properties may include a concentration (or a change in concentration) of a reactant or product, or a value of physical property (or a change in such value), such as temperature. Desirable configurations and physical characteristic of electronic sensor arrays and microwell arrays are described more fully below. In one embodiment of such sensor arrays, the chemFETs of the sensors include a floating gate. In another embodiment of the present teaching, electronic sensors of the array each generate an output signal that depends in part on the value of the voltage of a reference electrode that is in fluid contact with microwell array. In particular embodiments, a single reference electrode is provided so that each sensor generates output signals with the same reference voltage.

Components of one embodiment of the present teaching are illustrated diagrammatically in FIG. 1A. Flow cell and sensor array (100) comprise an array of reaction confinement regions (which may comprise a microwell array) that is operationally associated with a sensor array, so that, for example, each microwell has a sensor suitable for detecting an analyte or reaction property of interest. Preferably, a microwell array is integrated with the sensor array as a single chip, as explained more fully below. A flow cell can have a variety of designs for controlling the path and flow rate of reagents over the microwell array. In some embodiments, a flow cell is a microfluidics device. That is, it may be fabricated with micromachining techniques or precision molding to include additional fluidic passages, chambers, and so on. In one aspect, a flow cell comprises an inlet (102), an outlet (103), and a flow chamber (105) for defining the flow path of reagents over the microwell array (107). Embodiments of the flow cell are described more fully below. Reagents are discarded into a waste container (106) after exiting flow cell and sensor array (100). In accordance with the present teaching, a function of the apparatus is to deliver different reagents to flow cell and sensor array (100) in a predetermined sequence, for predetermined durations, at predetermined flow rates, and to measure physical or chemical parameters in the microwells that provide information about the status of a reaction taking place therein, or in the case of empty wells, information about the physical or chemical environment in the flow cell. To this end, fluidics controller (118) controls by lines (120 and 122) the driving forces for an exemplary fluidic subsystem including a plurality of reagents (114) and the operation of valves (for example, 112 and 116) by conventional instrument control software, e.g. LabView (National Instruments, Austin, Tex.). The reagents may be driven through the fluid pathways, valves and flow cell by pumps, by gas pressure, or other conventional methods. In embodiments where a single reference electrode (108) is positioned upstream of flow cell and sensor array (100), preferably a single fluid or reagent is in contact with reference electrode (108) throughout an entire multi-step reaction. This is achieved with the configuration illustrated in FIG. 1A where reagents 1 through K (114) are directed through passage (109) to flow cell (105). When those reagents are flowing, valve (112) is shut, thereby preventing any wash solution from flowing into passage (109). Although the flow of wash solution is stopped, there is still uninterrupted fluid and electrical communication between reference electrode, passage (109), and sensor array (107). At most reagents 1 through K when flowing through passage (109) diffuse into passage (111), but the distance between reference electrode (108) and the junction between passages (109) and (111) is selected so that little or no amount of the reagents flowing in common passage (109) reach reference electrode (108). Although FIG. 1A and other figures illustrate an electrode (for example, reference electrode, 108) as a cylinder concentric with a fluid passage (for example, 111), reference electrodes, such as (108), may have a variety of different shapes. For example, it could be a wire inserted into the lumen of (111). In one aspect, reference electrode (108) constitutes a section of passage (112) that is made of a conductive material, such as stainless steel, gold, or the like. Preferably the material is inert with respect to reagents in contact with it. Reference electrode (108) in one embodiment is a tube made of a conductive material which forms part of passage (112). Generally in the figures, whenever electrodes are represented as a cylinder concentric with a flow path, such figure element is intended to comprise electrodes having a variety of configurations, as noted, but with a preferred configuration as a tube of conductive material enclosing part of a flow path.

The value of the reference voltage depends on the interface between the electrode and the solution in which the electrode is in contact. It has been observed and appreciated that (for example) solutions of different nucleoside triphosphates cause the reference voltage to change, thereby causing undesirable changes in the output signals of the sensors. For multi-step reactions using frequent wash steps, wash solution (110) may be selected as the reagent in continuous contact with reference electrode (108) as illustrated in FIG. 1A. (That is, the wash solution would be the "selected electrolyte" or "selected reagent" and the dNTP reagents would be the "non-selected electrolytes" or "non-selected reagents" as the terms are used elsewhere herein). As further described below, in certain DNA sequencing methods washes are implemented after each introduction of nucleoside triphosphates; thus, in such methods a wash solution is preferably in continuous contact with reference electrode. Such contact may be obtained by including a reservoir for holding the selected electrolyte, such as the wash solution, which is connected by a branch passage (e.g. 111) to a common passage (e.g. 109) for delivering electrolytes to a reaction vessel. In one aspect, the branch passage has a valve disposed between the reservoir (e.g., 110) and a junction with the common passage, wherein the reference electrode is disposed in the branch passage between the valve and the junction such that the reference electrode is in fluid communication with the reaction vessel and such that whenever the valve (e.g. 112) is shut and fluid within the branch passage is stationary, substantially no non-selected electrolyte contacts the reference electrode. The only transfer of non-selected electrolyte into the branch passage is by diffusion; thus, the reference electrode may be place sufficiently far away from the junction so that minimal or no non-selected electrolyte reaches it during the time the selected electrolyte is stationary.

Further components of this embodiment include array controller (124) (e.g., an embodiment of a computational circuitry) for providing bias voltages and timing and control signals to the sensor array (if such components are not integrated into the sensor array), and for collecting or processing output signals. Information from flow cell and sensor array (100), as well as instrument settings and controls may be displayed and entered through user interface (128). For some embodiments, for example, nucleic acid sequencing, the temperature of flow cell and sensor array (100) is controlled so that reactions take place and measurements are made at a known, and preferably, a predetermined temperature. Such temperature may be controlled by conventional temperature control devices, such as, a Peltier device, or the like. In one aspect, temperature is conveniently controlled by controlling the temperatures of the reagents flowing through the flow cell. Noise in output signals due to temperature differences within an array or due to temperature fluctuations may be recorded by temperature reference sensors within the array, as described in Rothberg et al (published patent application cited above). Such noise may then be subtracted from the output signal in conventional signal processing techniques.

Figure 2A:
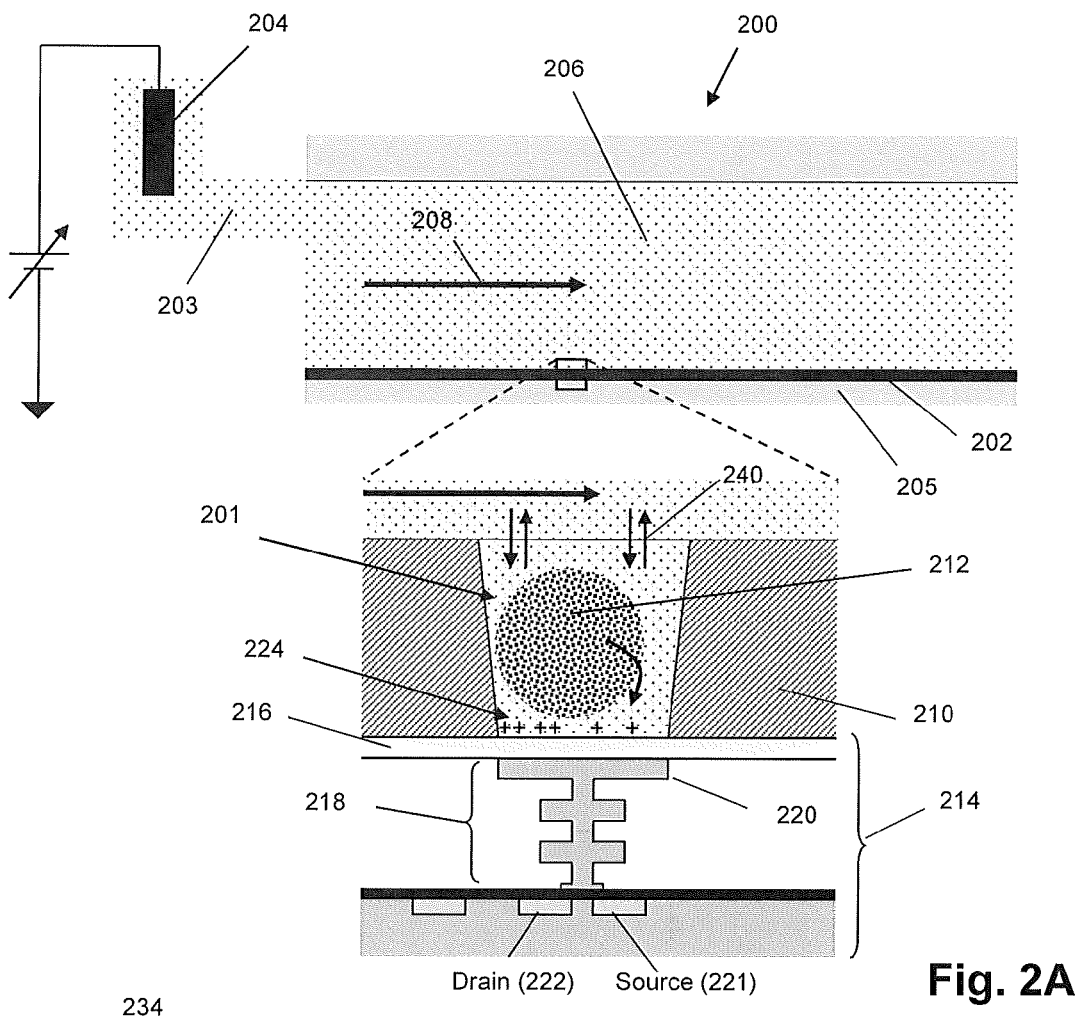
FIG. 2A illustrates a section of a flow cell with an external reference electrode and enlargement of an exemplary electronic sensor.

FIG. 2A is an expanded and cross-sectional view of flow cell (200) showing a portion (206) of a flow chamber with reagent flow (208) moving across the surface of microwell array (202) over the open ends of the microwells. Preferably, microwell array (202) and sensor array (205) together form an integrated unit forming a bottom wall or floor of flow cell (200). In one embodiment, reference electrode (204) is fluidly connected to flow chamber (206). A microwell (201) and sensor (214) are shown in an expanded view. Microwell (201) may be formed by conventional microfabrication technique, as described briefly below. Microwell volume, shape, aspect ratio (such as, base width-to-well depth ratio), and the like, are design choices that depend on a particular application, including the nature of the reaction taking place, as well as the reagents, byproducts, and labeling techniques (if any) that are employed. Sensor (214) is a chemFET with floating gate (218) having sensor plate (220) separated from the microwell interior by passivation layer (216). Sensor (214) is predominantly responsive to (and generates an output signal related to) the amount of charge (224) present on the passivation layer (216) opposite of sensor plate (220). Changes in charge (224) cause changes in the current between source (221) and drain (222) of the FET, which may be used directly to provide a current-based output signal or indirectly with additional circuitry to provide a voltage output signal. Reactants, wash solutions, and other reagents move into microwells from flow chamber (206) primarily by diffusion (240).

Typically reactions carried out in microwells (202) are analytical reactions to identify or determine characteristics or properties of an analyte of interest. Such reactions generate directly or indirectly byproducts that affect the amount of charge adjacent to sensor plate (220). (Indirect detection may occur, for example, if byproduct chelators or other binding compounds are used that affect the sensor after binding an analyte of interest, or if labeling moieties are employed, such as enzymes that may generate a secondary byproduct as the result of a binding event, or the like) If such byproducts are produced in small amounts or rapidly decay or react with other constituents, then multiple copies of the same analyte may be analyzed in microwell (201) at the same time in order in increase the output signal ultimately generated. In one embodiment, multiple copies of an analyte may be attached to solid phase support (212), either before or after deposition into a microwell. Solid phase supports (212) may include microparticles, nanoparticles, beads, solid and porous, comprising gels, and the like. For nucleic acid analytes, multiple, connected copies may be made by rolling circle amplification (RCA), exponential RCA, and like techniques, to produce an amplicon without the need of a solid support.

Figure 2B:
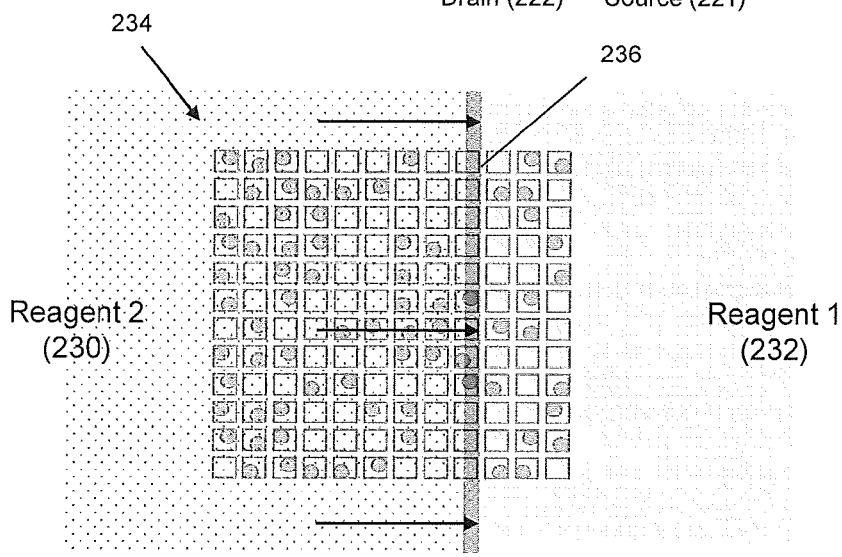
FIG. 2B illustrates the movement of two successive reagents over a section of a microwell array with an ideally uniform flow front between the different reagents.

As mentioned above, in one aspect, flow cells of the present teaching constrain reagents to move transversely in a laminar flow over a microwell array. The rate of flow is a design choice depending on the nature of the reactions carried out, the geometry and size of the flow chamber and microwell array, and the like. Generally, however, when different reagents are successively delivered to the microwells, a flow cell delivers each new reagent flow with a uniform flow front as it transits the flow chamber during the switch from one reagent to another. That is, flow cell design and reagent flow rate are selected so that as one reagent follows another with little or no mixing occurring at the boundary between the successive fluids. FIG. 2B illustrates a uniform flow front between two reagents moving across section (234) of a microwell array. A "uniform flow front" means that successive reagents, e.g. reagent 1 (232) and reagent 2 (230), undergo little or no mixing as the reagents move across the microarray, thereby keeping boundary (236) between reagent 1 (232) and reagent 2 (230) narrow as it moves across a microarray. Such boundaries may be linear for flow cells having inlets and outlets at opposite ends of their flow chambers, or such boundaries may be curvilinear for flow cells having central inlets (or outlets) and peripheral outlets (or inlets).

Reference Electrodes for Electronic Sensor Arrays

The fluid-electrode interface influences the way the reference potential is transmitted into the fluid. That is, the interface potential between the fluid and the electrode fluctuates with the composition of the fluid (which may be somewhat turbulent and inhomogeneous), introducing a voltage offset to the potential of the bulk fluid which varies with time and possibly location, as well. Considerably greater reference potential stability may be achieved by moving the location of the reference electrode so that it is substantially isolated from changes in fluid composition. This may be accomplished by introducing a conductive solution of a consistent composition over at least part of the surface of the electrode (hereafter the "electrode solution" or "selected electrolyte"), arranging the electrode to avoid it coming into direct contact with the changing fluids in the flow cell and, instead, arranging the electrode solution (not the electrode) to come into electrical contact with the fluid in the flow cell. The result is a transfer of the reference potential to the flow cell solution (be it a reagent or wash or other solution) that is considerably more stable than is obtained by direct insertion of an electrode into the flow cell solution. This arrangement is referred to as a liquid-liquid or fluid-fluid reference electrode interface. The fluid-fluid interface may be created downstream from the flow cell, upstream from the flow cell (as exemplified in FIG. 1A), or in the flow cell. Examples of such alternative embodiments are shown in Figs. FIGS. 1B-1E.

Figure 1B:
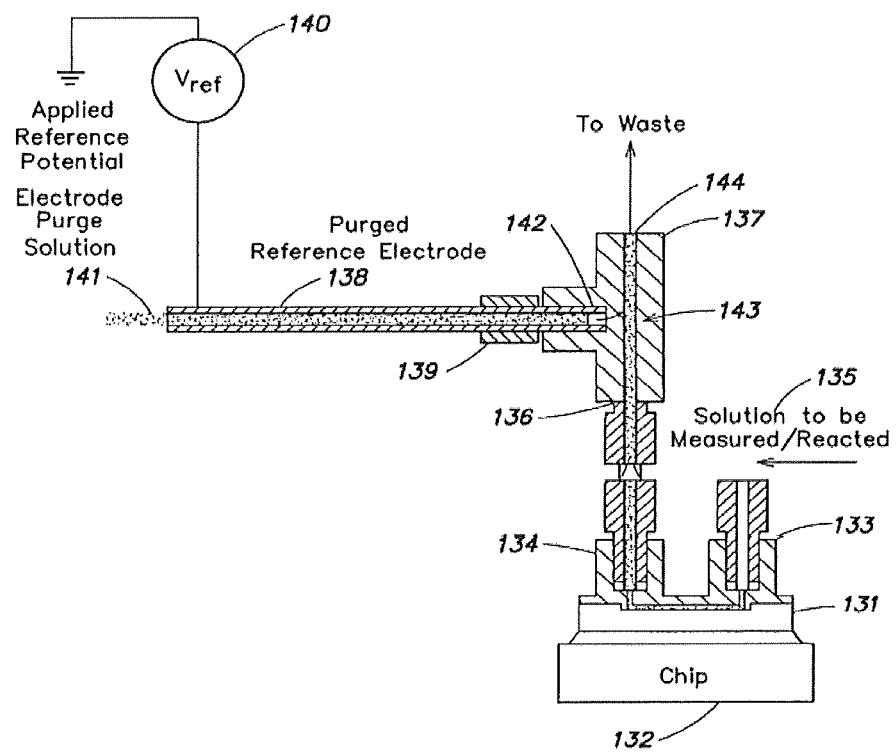
FIG. 1B is a diagrammatic illustration of a cross-section of a first example of a fluid-fluid reference electrode interface in which the reference electrode is introduced downstream in the reagent path from the flow cell.

Turning first to FIG. 1B, there is shown a diagrammatic illustration of an embodiment in which the fluid-fluid interface is created downstream from the flow cell. In this example, the flow cell apparatus (131) is, as above, mounted on a chip (132) which contains the sensor array (not shown). The flow cell apparatus includes an inlet port (133) and an outlet port (134). That is, the reagent fluids are introduced into port (133) via conduit (134) and they exit via port (134). A first port (136) of a fluid "Tee" connector (137) is coupled onto flow cell outlet port 134 via conventional couplings to receive the fluid exiting from the flow cell. A reference electrode such as a hollow electrically conductive tube (138) is fed into another port of the Tee connector via a fluid-tight coupling (139). The reference electrode is connected to a reference potential source (140) and a suitable electrode solution (141) is flowed into the center bore of the electrode tube.

Two modes of operation are possible. According to a first mode, the electrode solution may be flowed at a rate that is high enough to avoid backflow or diffusion from the fluid flowing out of the flow cell. According to a second mode, once the electrode solution has filled the electrode and come into contact with the outlet flow from the flow cell, a valve (not shown) may be closed to block further flow of the electrode solution into the electrode and, as the electrode solution is an incompressible liquid, there will be substantially no flow into or out of the electrode, yet the fluid-fluid interface will remain intact. This presumes, of course an absence of bubbles and other compressible components. For a fluid-fluid interface to take the place of a metal-fluid interface, the tip (142) of the electrode (138) is positioned to stop within the Tee connector short of the fluid flow out of the flow cell, so that it is the "electrode solution," not the electrode itself, that meets the outlet flow from the flow cell, indicated at (143), and carries the reference potential from the electrode to the reagent solution exiting the flow cell. The two fluid streams interact in the Tee connector at (143) and if the electrode solution is flowing, it flows out the third port (144) of the Tee connector with the reagent flow, as a waste fluid flow, for disposal. This approach eliminates interfacial potential changes at the electrode surface. Using a fluid-fluid interface to convey a stable reference potential from a reference electrode to a flow cell, various alternative embodiments are possible.

Figure 1C:
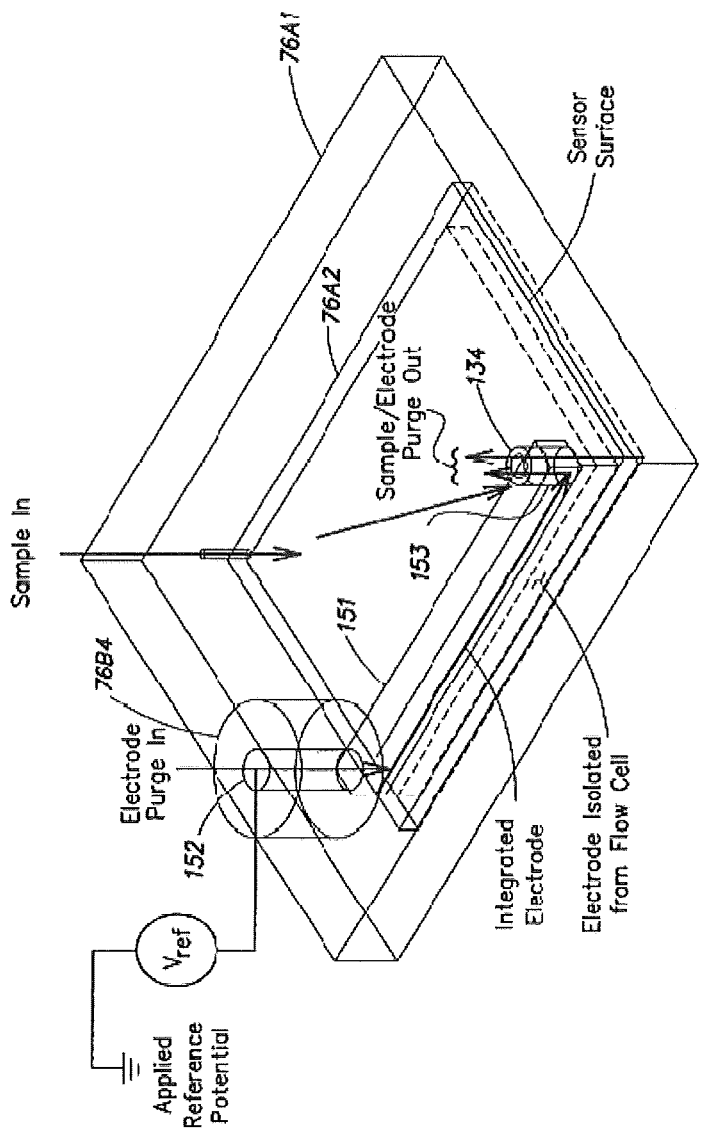
FIGS. 1C and 1D are diagrammatic illustrations of two alternative examples of ways to construct apparatus to achieve the fluid-fluid interface of FIG. 1B.

In one alternative, illustrated in FIG. 1C, the referencing junction (i.e., the fluid-fluid interface) can be moved into the structure of the members forming the flow cell or even into the sensor chip itself, but with the electrode solution never entering the flow cell. For example, a manifold (151) may be formed in the flow cell assembly outside the flow chamber itself, having an inlet (152) for receiving electrode solution and an outlet (153) in fluid communication with the flow cell's outlet conduit (134). The electrode may be a separate element disposed in the manifold or it may be a metallization applied to an interior surface of the manifold.

Alternatively, the manifold can be formed in the substrate of the chip itself by fabricating in the substrate a hollow region which can serve as a conduit allowing fluid passage from an inlet end to an outlet end. An electrode may be inserted therein via a separate inlet port (152) or part of the (interior or exterior, ass appropriate) surface of the conduit may be metalized during fabrication, to serve as the electrode. The flow path for reagent fluid to exit the flow chamber may include a conduit portion and the electrode conduit/manifold may deliver electrode solution to the reagent fluid outlet conduit, wherein the two fluids come into contact to provide the fluid-fluid interface that applies the reference electrode voltage to the flow cell.

In each instance, the electrode may be hollow and have the electrode solution delivered through its interior, or the electrode solution may be delivered over the exterior of the electrode. For example, as shown in FIG. 1C, the electrode may be hollow, such as being the interior surface of the manifold 151, and it may have an exterior that is insulated from the flow cell using any suitable structure and material (not shown, to avoid obfuscation of the basic idea).

The electrode assembly thus may be built into the sensor chip itself or into the flow cell or its housing, coupled with a fluid inlet through which electrode solution may be introduced. The flow path for reagent fluid to exit the flow chamber may include a conduit portion (134) into which the electrode solution is presented, and wherein the two fluid flows come into contact to provide the fluid-fluid interface. The electrode solution may flow or be static.

Figure 1D:
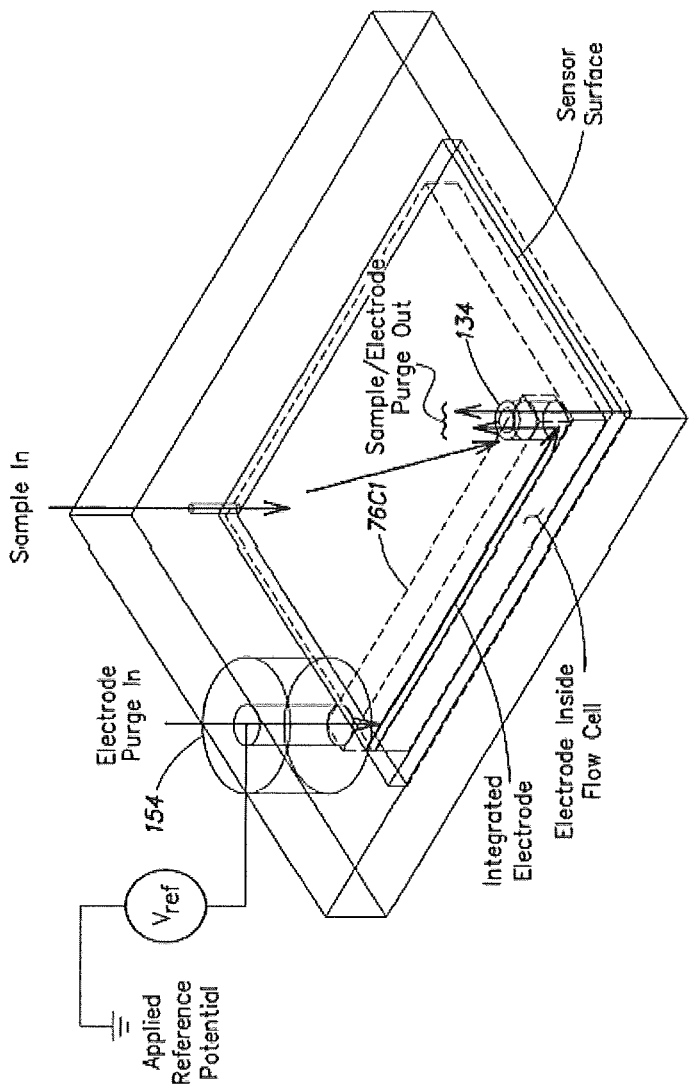
Figure 1E:
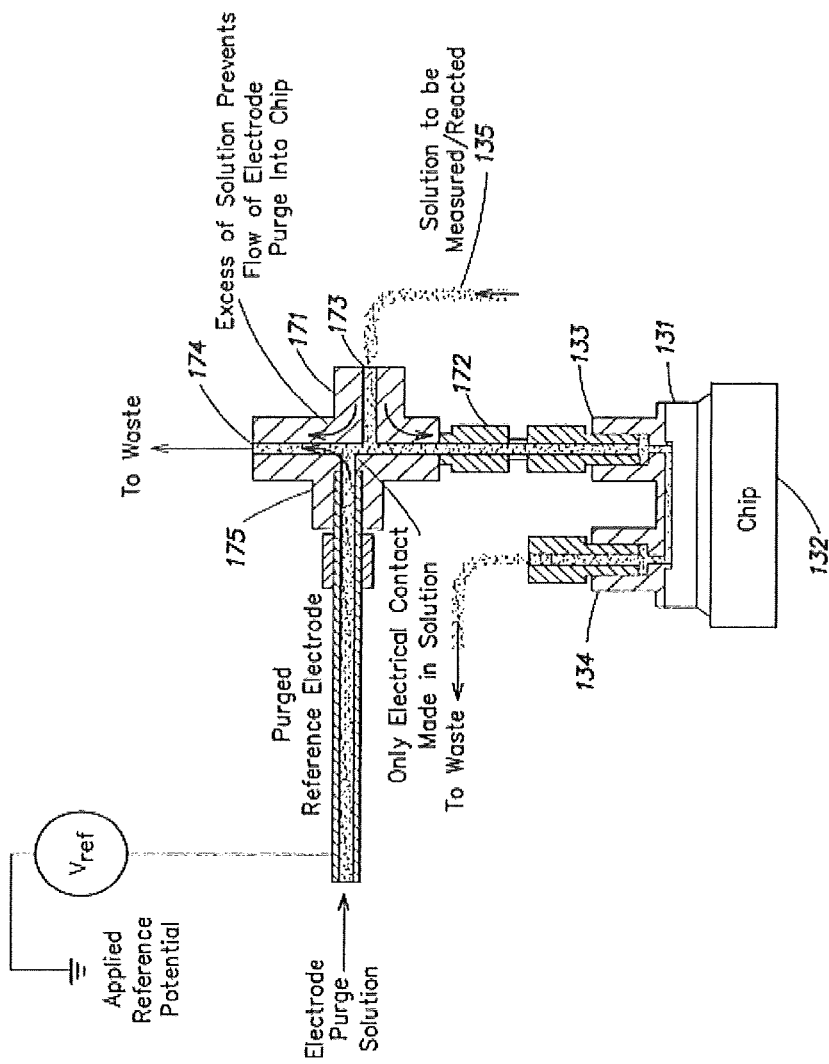
FIG. 1E is a diagrammatic illustration of a cross-section of a second example of a fluid-fluid reference electrode interface in which the reference electrode is introduced upstream in the reagent path from the flow cell.

As a further alternative embodiment, depicted in FIG. 1D, the electrode structure may be integrated into or disposed within the flow cell itself. This may be done in two distinctly different ways. First, the electrode solution may be introduced into the flow chamber and flowed from an inlet (154) into the flow cell (provided for that purpose) to an outlet port (134) through which both the electrode solution and the reagent flow exit the flow chamber. If both fluids are arranged to move through the chamber in a laminar flow, they will not intermix (or there will be little mixing and interaction) until they reach the outlet. So there need not be a barrier between the two fluids. Their entire region of contact will be the locus of fluid-fluid interfacing, which may provide considerably more surface for that interface than the other illustrated alternatives. Second, a fluid conduit may be provided adjacent to the flow chamber or even fully or partly within the flow chamber, with a non-conductive exterior. The electrode may extend along the interior of the conduit, between an electrode fluid inlet and a fluid outlet that permits the electrode solution to interface with the reagent flow, such as in a common outlet conduit (134).

In the foregoing examples, the reference potential is introduced either in or downstream of the flow cell. However, the same approach is possible with the electrode provided upstream of the flow cell, as shown diagrammatically in FIG. 1E. There, (133) is the inlet port to the flow cell and (134) is the outlet port, as in FIG. 1B. A cross-connector (171) having four ports has a first port (172) coupled onto the inlet port. A second port (173) receives the solution to be reacted or measured (e.g., a reagent) via inlet conduit (135). A third port (174) is used as a waste outlet port. The fourth port (175) receives the electrode in the same manner as previously shown in FIG. 1B. Within the cross-connector, the electrode solution and the solution to be reacted/measured interact to transmit the reference potential into the flow cell. In contrast with some of the other alternative embodiments, however, at least some implementations of this embodiment may require that the solution to be measured/reacted must have a sufficiently high flow rate as to prevent flow of the electrode solution into the flow chamber. However, with judicious configuring of the cross-connector, it may still be possible to avoid the need to flow electrode solution continuously.

Instrumentation Systems/Electronics & Software
Gain-Based Chip Calibration

In various embodiments, it may be desirable to provide a calibration routine used for preparing the electrochemical detection system for analysis. As described above, the substrate or chip upon which analytes are disposed during an analysis may comprise a sensor array. It may be desirable to calibrate the signal acquisition sensitivity or gain of the system so as to improve or optimize performance of the system by performing a calibration routine. For example by adjusting the sensor response so as to normalize or bring a substantial majority of the pixels associated with the sensor array into a desired operating range. In various embodiments, the desired operating range of the pixels may be selected so as to be aligned with the sensor DAC's. In one exemplary embodiment, the sensor array may have an approximate output voltage in range of +/−2V. It may however be desirable, to use a subset or portion of this range for example, approximately a 256 mV acquisition window with which to sample from the +/−2V range. Such sampling may be directed into a multi-bit digitizer and may aid in improving signal resolution over noise and improving accuracy of sampling.

In various embodiments such as those pertaining to nucleic acid sequencing operations, the window size may be selected such that a substantial majority of pixels lie within and/or are centered. Such an approach may help ensure that usable pixels are available for sequencing. Further it may be noted that the shape of the distribution may change with the input reference electrode voltage, as well as the overall gain of the selected group of pixels. In various embodiments, sweeping the reference electrode range and sweeping the DAC window, and perturbing the reference electrode, can provide insights into the gain at each pixel. Furthermore, an overall average gain for the chip or sensor array may be calculated at a selected reference electrode voltage. In various embodiments, maximizing the gain and moving the DAC window such that the majority of pixels lie inside that window may be performed to improve the signal to noise ratio for the sensor array. Furthermore, such an approach may aid in improving or maximizing the number of pixels in range. Software implementation of the above-described methods may therefore be helpful in effectively using the sensor array.

Use of Electronic Sensors to Locate Analytes in Microwells

Figure 3A:
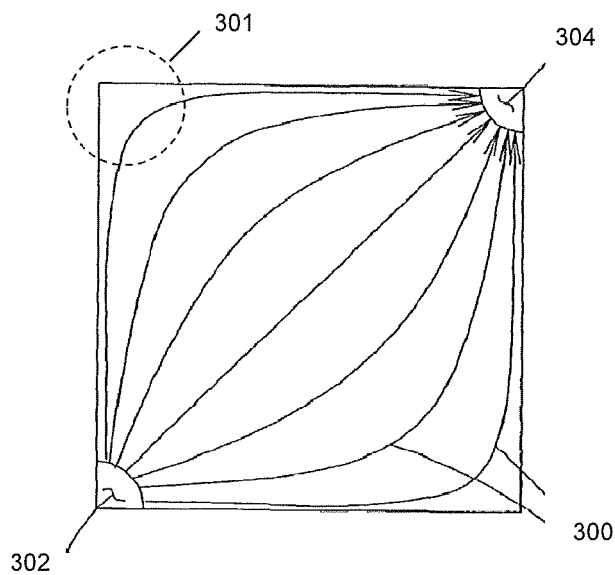
FIG. 3A is a diagram illustrating flow paths through a flow chamber having diagonally opposed inlet and outlet.

In one aspect of the present teaching, electronic sensors are used to locate microwells that contain analyte or particles and microwells that are empty. Such a process is useful because output signals from empty wells allows the estimation of common noise components that may be subtracted from output signals measured from analyte-containing microwells, thereby improving signal-to-noise ratios. Moreover, in many embodiments analytes or particles are randomly disposed in microwells by placing them in solution and flowing them into the flow chamber where they settle randomly into microwells, as illustrated in FIG. 3A, and further exemplified in Rothberg et al (U.S. patent publication cited above); thus, a method of electronically identifying which microwells contain analyte and which are empty is needed.

Usually, only a single analyte is disposed in a single microwell. In one aspect, multiple copies of the same analyte are attached to solid support, such as a bead or particle, which, in turn, is selected to match a microwell in size and shape so that only a single solid support fits into a single microwell, thereby ensuring only one kind of analyte is in a single microwell. As mentioned above, for some types of analytes, such as nucleic acids, methods are available, such as rolling circle amplification (RCA), or the like, to construct connected amplicons that form a single body that may exclusively occupy a microwell. After the random distribution of analytes into microwells, electronic sensors responsive to changes in surface charge may be used to identify microwells containing analyte. Thus, in one aspect, a method of the present teaching includes introducing a sensor-active reagent, which may be the same or different as a reagent used in an analytical process of interest, which is capable of altering the charge adjacent to a sensor as a function of its concentration.

In one embodiment, this aspect of the present teaching may comprise the following steps: (a) changing reagents in a flow chamber from a first reagent that sensors generate in response thereto a first output signal to a second reagent that sensors to generate in response thereto a second output signal; and (b) correlating a time delay in the generation of a second output signal by a sensor in response to said changing with the presence of an analyte in its corresponding microwell. Any type of electrochemical sensor may be used in this aspect of the present teaching, including a potentiometric sensor, an impedimetric sensor, or an amperometric sensor, so long as the output signal depends on the interaction of an electrode or other analyte-sensitive surface and the sensor-active reagent whose arrival is delayed by physical or chemical obstructions in a microwell. In one embodiment, the sensor-active reagent is a wash solution at a different pH than the reagent it replaces, which may also be the wash solution. The step of changing reagents includes recording the output signals of the sensors in the array so that a continuous time record of signal values (or a digital representation thereof) is obtained which can be analyzed to determine the timing of changes in output signals that correspond to the times at which the sensor-active reagent reach the respective sensors. Such data recording and analysis may be carried out by conventional data acquisition and analysis components.

Figure 2C:
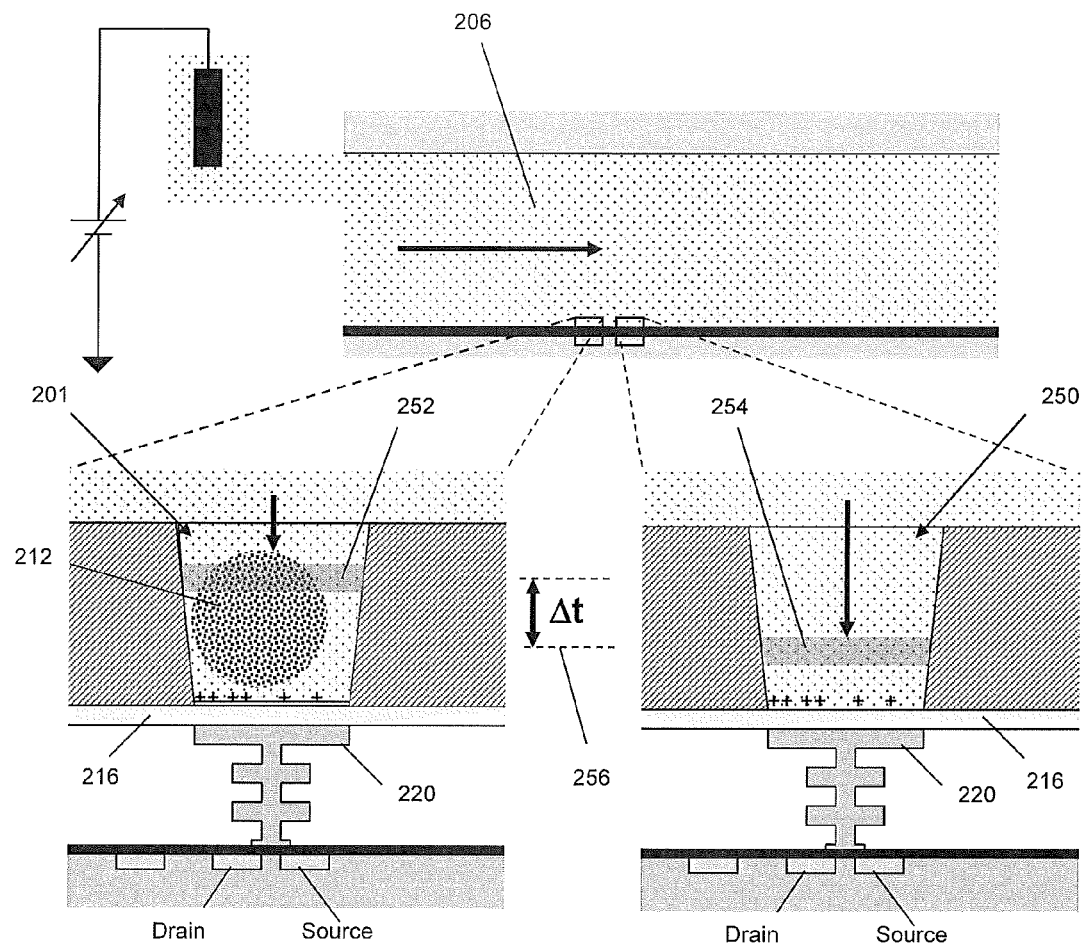
FIG. 2C illustrates how a particle retards the progress of a sensor-active reagent, thereby creating an output signal time delay that may be used to determine the presence of the particle in the microwell.
Figure 2D:
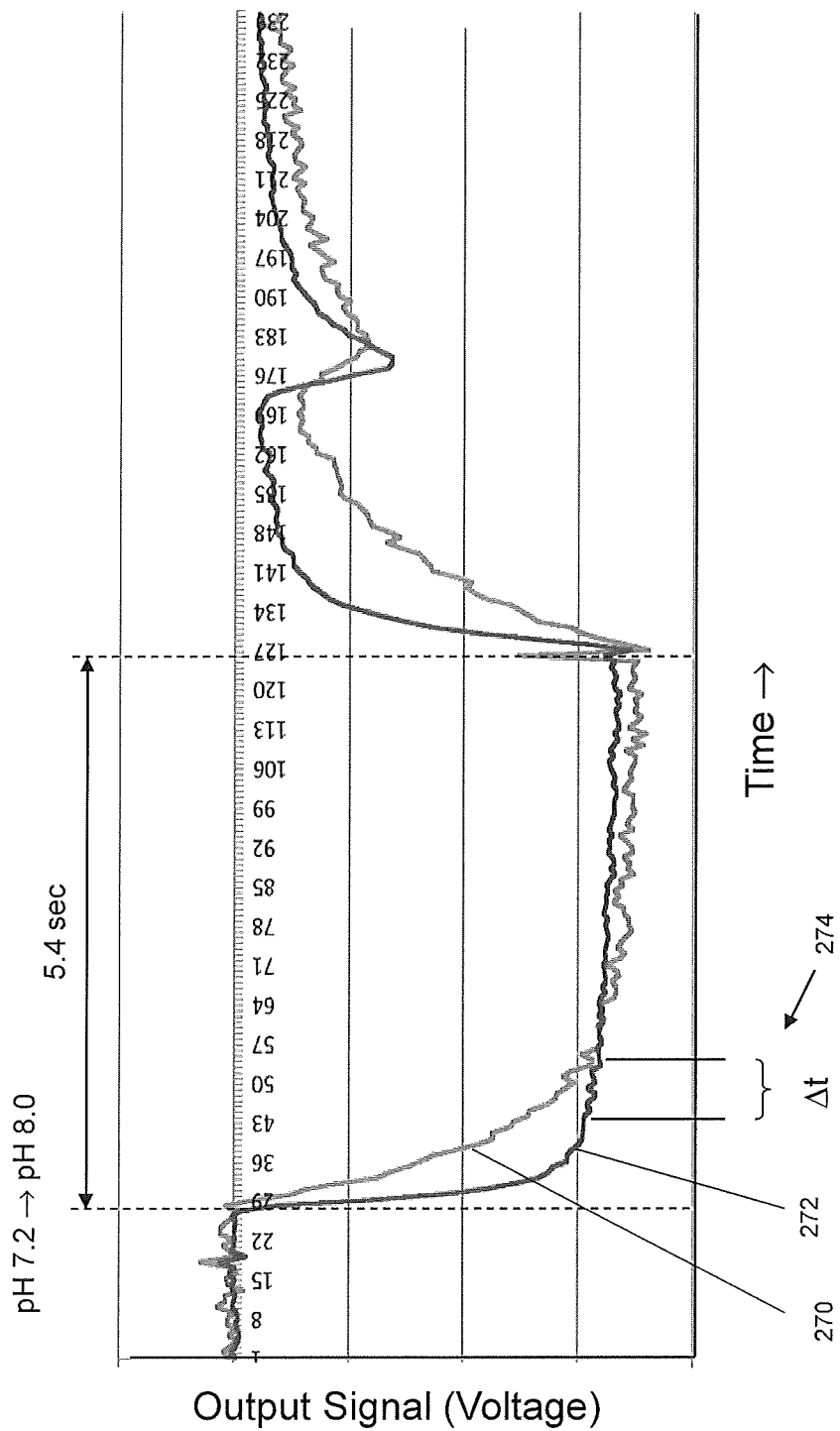
FIG. 2D compares output signal data from a microwell with a particle and a microwell without a particle.
Figure 3B:
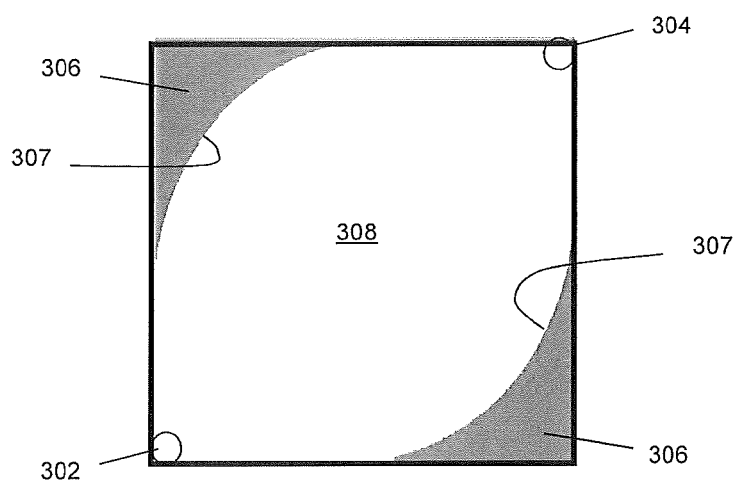
FIG. 3B is a top view of a mask used for fabricating a sensor array of floating gate chemFETs, where floating gates of chemFETs outside of a diagonal flow region are electrically connected in the manufacturing process, in order to eliminate or minimize noise contributions from unused sensors outside of the diagonal flow region.
Figure 3C:
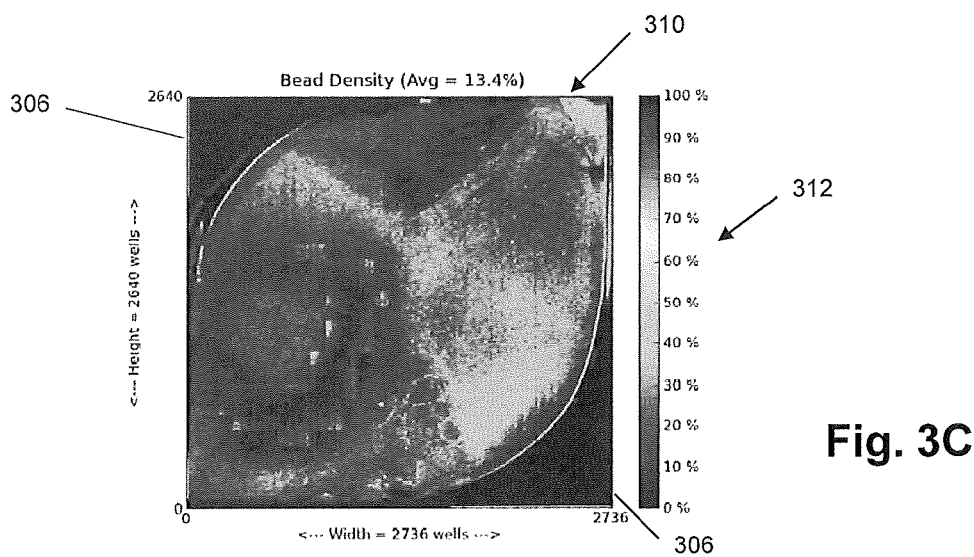
FIG. 3C is a display showing the density of analyte deposition in a large-scale microwell array as determined by sensor output signal changes in response to exposure to a step-function pH change.

As illustrated in FIG. 2C, when sensor-active reagent flows into the flow chamber, it diffuses from flow chamber (206) through microwell (201) that contains particle (212) as well as through microwell (250) and to the region of passivation layer (216) opposite of sensor plate (220). Whenever microwell (201) contains analyte or particle (212), diffusion front (252) of the charging reagent is retarded relative to front (254) in empty well (250) either by the physically obstruction in the diffusion pathway by the analyte/particle or by chemical interactions with the analyte/particle or its associated solid support, if present. Thus, microwells containing analyte may be determined by correlating a time delay (256) in the change of output signal of the sensor with the presence of analyte/particle. In one embodiment, where the sensors are configured to measure pH, the charging reagent is a solution having a predetermined pH, which is used to replace a first reagent at a different predetermined pH. In embodiments for nucleic acid sequencing, the retardation of hydrogen ion diffusion is affected both by the physical obstruction and buffering capacity of the analyte or particle. Preferably, the first reagent pH is known and the change of reagents effectively exposes sensors of the microwells to a step-function change in pH, which will produce a rapid change in charge on their respective sensor plates. In one embodiment, a pH change between the first reagent and the charging reagent (or sometimes referred to herein as the "second reagent" or the "sensor-active" reagent) is 2.0 pH units or less; in another embodiment, such change is 1.0 pH unit or less; in another embodiment, such change is 0.5 pH unit or less; in another embodiment, such change is 0.1 pH unit or less. The changes in pH may be made using conventional reagents, e.g. HCl, NaOH, or the like. Exemplary concentrations of such reagents for DNA pH-based sequencing reactions are in the range of from 5 to 200 µM, or from 10 to 100 µM. The variation in charge at a microwell surface opposite a sensor plate indicative of the presence or absence of analyte (or a byproduct from a reaction on an analyte) is measured and registered as a related variation in the output signal of the sensor, e.g. a change in voltage level with time. FIG. 2D shows data from sensors on an array manufactured in accordance with Rothberg et al, U.S. patent publication 2009/0127589, with sensor layout, pitch (9 µm), and floor plan as described in FIGS. 10, 11A, and 19. A microwell corresponding to a first sensor is loaded with a 5.9 µm diameter bead with template, primer and polymerase attached and a microwell corresponding to a second sensor is empty. The output signals from each sensor are recorded while the reagent in a flow cell is changed from pH 7.2 to pH 8.0 and maintained at the pH 8.0 value for 5.4 sec. Curve (270) shows the values of the output signal from the first sensor (whose microwell contains a bead) and curve (272) shows values of the output signal from the second sensor (whose microwell is empty). Both curves show a change from a high value corresponding to pH 7.2 to a low value corresponding to pH 8.0. However, the signal corresponding to the empty well reaches the low value noticeably faster than the signal corresponding to the bead-bearing microwell. The difference in time, $\Delta t$ (274), at which the respective output signals reach the lower value, or a comparable measure, is readily determined with conventional data analysis techniques. Locations and densities of particle-containing microwells within an array may be displayed graphically in a number of ways, including as a contour map or "heat" map, as illustrated in FIG. 3C.

In one aspect of the present teaching, microwell arrays may be provided with locations of randomly distributed analytes determined Such a product, or article of manufacture, comprises (i) a sensor array comprising a plurality of sensors formed in a circuit-supporting substrate, each sensor of the array being configured to generate at least one electrical signal related to a concentration or presence of one or more predetermined species proximate thereto and a microwell array disposed on the circuit-supporting substrate such that each microwell thereof has an opening on a surface of the microwell array and is disposed on at least one sensor; and (ii) a plurality of analytes randomly distributed in the microwells at locations determinable by an output signal generated by its corresponding sensor. In one embodiment, the analytes comprise particles having attached thereto clonal populations of DNA fragments, e.g. genomic DNA fragments, cDNA fragments, or the like.

Instrumentation Systems/Electronics & Software
Pixel Classification

As noted above, each chip or sensor array may contain a plurality of microwells or reaction chambers. In such systems, it may be desirable identify or classify the contents of each micro-well. Such an approach may improve the overall analysis accuracy or improve the performance of the system. Exemplary classifications may include determining whether a well or reaction chamber is empty or contains an analyte or substrate associated with an analyte such as a bead/particle/nanoball/etc. In one exemplary embodiment relating to nucleic acid sequencing it may be desirable to not only identify if a well contains an analyte or substrate but also determine if there is a "productive" analyte reaction or detection mode that takes place. Thus for sequencing wells (those containing or associated with a bead/particle/nanoball/etc) it may be desirably to identify whether a selected well or reaction chamber contains or is associated with an active sequencing entity (e.g. "live" or "dud", test fragment, library fragment, or ambiguous sequencing entity). Furthermore, it may be useful to be able to identify the location or presence of empty, non-responsive, and or inactive wells. Such an identification may be desirably used to account for and in some instances remove correlated noise from wells that are being used in analysis (e.g. used during sequencing).

In one exemplary embodiment pertaining to nucleic acid sequencing, classification may be performed in two stages. In the first stage, a selected pH buffer at a different pH than a selected wash buffer is passed over or exposed to the chip or sensor array. In certain configurations, the chip sensors detect the pH change over time. In one aspect, due to the diffusion rates on the wells and the pH concentration, one may measure the change over time. It may be observed that empty wells may have a different rate of change than wells with a particle in them due to the change in diffusion properties of those wells with a particle. In one embodiment, for a selected well, a decision as to whether the well contains a particle or not may be made on the basis of the average of neighbor wells is compared to the well in question. In various embodiments, if the diffusion rate in the well in question is slower than the average rate of surrounding neighbors, then this well may be identified as containing a particle and otherwise not containing a particle. It will be appreciated that there may be additional methods for establishing a baseline (e.g. pH change over time) such as fitting the signal to exponentials or other models of the expected background signal, performing regional "time-warp" functions on the data to fit the well in question to the time-warp model, etc.

In a second stage, one may observe wells containing particles. For example, using the first few flows, and the instance where two different sequencing keys at the beginning of each read are used (described in greater detail below), one may perform a threshold test to determine the relative activity of the particle (e.g. identify the particle as live or dud). For live particles, one may observe the signal compared to each key for each flow, thus for positive signals detected for either key, the particle may be marked or associated as that type (e.g. TF or Lib). In various embodiments, for those particles that pass the test for both key types, those particles may be identified or marked as ambiguous.

Flow Cells and Output Signal Collection

Flow cell designs of many configurations are possible; thus the system and methods presented herein are not dependent on use of a specific flow cell configuration. Design and performance specifications of a flow cell of the present teaching include, but are not limited to the following: (i) minimization of the time required to change reagents that analytes are exposed to, (ii) minimization of mixing of successive reagents, that is, providing a uniform flow front between successive reagents, (iii) provide a laminar flow and uniform transit times of fluids across an array (including minimization or elimination of any regions (such as dead volumes) where fluids become trapped so that mixing between successive flows can occur), (iv) provide sufficient volume of flow over microwells (for example, by providing a flow chamber of sufficient volume above the microwell array) so that efficient exchange of material by diffusion occurs between the microwell volumes and the flow), (v) minimization of bubble formation (including reducing sharp corners or edges that promote bubble formation, controlling dissolved gas in the reagents, and providing surfaces that are readily wetted by aqueous reagents), (vi) facilitation of the placement of a reference electrode, (vii) facilitation of loading analytes into microwells or reaction chambers in an array, and the like.

In one aspect, a flow cell of the present teaching directs reagent flows to a microwells array such that each microwell is exposed to substantially the same flow conditions, including flow rate, concentration, and the like, at substantially the same time throughout the microwell array, as reagents are delivered to the array. By "substantially the same time" in reference to such exposure it is meant that the transit time through the flow chamber of a boundary between two successive reagents is small in comparison to the length of time a microwell is exposed to any one reagent. For some flow cell configurations identical flow rates at each microwell are not possible, such as with flow cells having inlets and outlets located diagonally in a flow chamber constrained to a rectilinear space. Nonetheless, a preferred design feature is that differences in flow conditions, such as flow rate, experienced by different microwells are minimized by a flow chamber and the flow path it defines. As mentioned above, a flow cell can have a variety of designs for achieving the above performance and manufacturing criteria, such as disclosed in Rothberg et al, U.S. patent publication 2009/0127589; Rothberg et al, U.K. patent application GB24611127. A flow cell of the present teaching that meets such design and performance criteria is illustrated in FIGS. 4A to 4E. The illustrated designs provide for simple manufacture where a flow cell is formed by attaching a component with inlet and outlet to a chip, or encapsulated microwell array-sensor array unit. In this embodiment, a flow chamber is the interior space formed when such pieces are combined, or attached to one another. In the design, an inlet is positioned at a corner of the flow chamber and an outlet at the diagonally opposed corner. This design is simple in that it requires only two manufactured pieces and the diagonal positioning of the inlet and outlet minimizes regions (e.g. (301) in FIG. 3A) of the flow chamber where reagent may be trapped or their transit times retarded. FIG. 3A illustrates flow paths (300) of a reagent as it transits a flow chamber along its diagonal axis from inlet (302) to outlet (304). In one embodiment, a flow chamber is defined by reference to such flow paths, as shown in FIG. 3B. That is, in the example of FIG. 4A, walls (410) and the boundary (307) (defining "pinned" sensors, described more fully below) are shaped to substantially follow the flow paths that reagents would follow through a square or rectangular flow chamber with diagonally opposed inlet and outlet. The result is that reagent flows are confined to central region (308) and corner regions (306), where reagents could mix or form eddies, are rendered inaccessible. The curvature of boundary (307) may be estimated (for example using a section of a quadratic or like standard curve) or it may be computed using commercially available fluid dynamics software, e.g., SolidWorks from Dassault Systems (Concord, Mass.); Flowmaster from FlowMaster USA, Inc. (Glenview, Ill.); and OpenFOAM (open source code for computational fluid dynamics available on the world wide web, www.opencfd.co.uk). In embodiments employing floating gate chemFETs as sensors, preferably, sensors in the reagent-inaccessible regions (306) are electrically connected so as not to introduce spurious voltage levels into output signals generated in those sections of the sensor array. That is, in such embodiments, readout circuitry of the sensor array continues to readout all columns and all rows, so that specialized circuits or programming is not required to avoid the sensors in the inaccessible regions. Instead, constant predetermined output signals are registered from sensors in such regions.

In one aspect of the present teaching described above, reaction chambers or microwells containing analytes are identified by introducing successive reagents (referred to herein as a first reagent and a predetermined reagent) into the flow cell that change the charge sensed by the sensors of the array in a predetermined manner. As shown in FIG. 3C, results of such identification may be displayed as a density map of the microwell array (310) in the flow chamber, where the distribution of analytes within microwells of the array are indicated by color scale (312). In this embodiment, colors of scale (312) indicate a local percentage of microwells (e.g. percentage of each non-overlapping regions of 100 microwells) containing analytes throughout the array, except for unused regions (306).

Figure 4A:
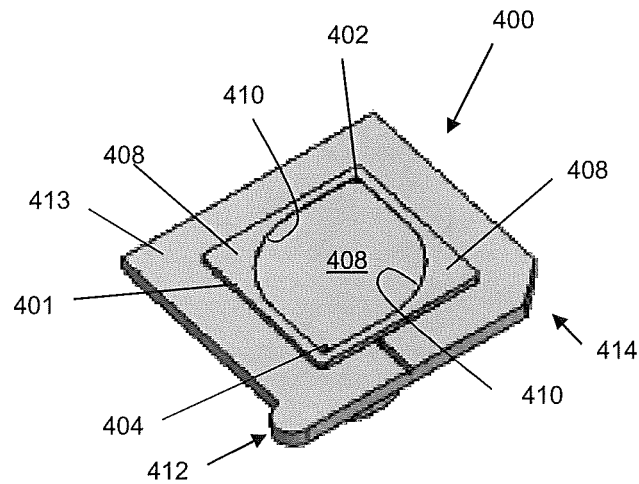
FIG. 4A-4D show different views of flow cell components and their integration with a microwell-sensor array chip.
Figure 4B:
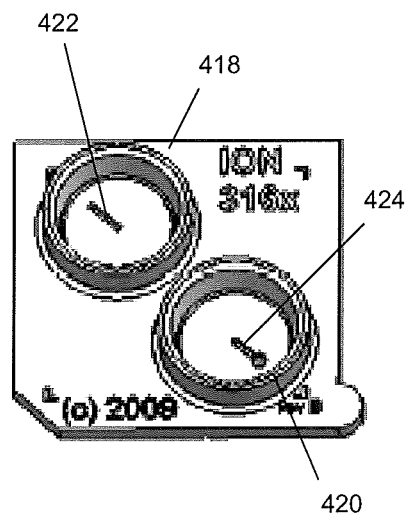
Figure 4C:
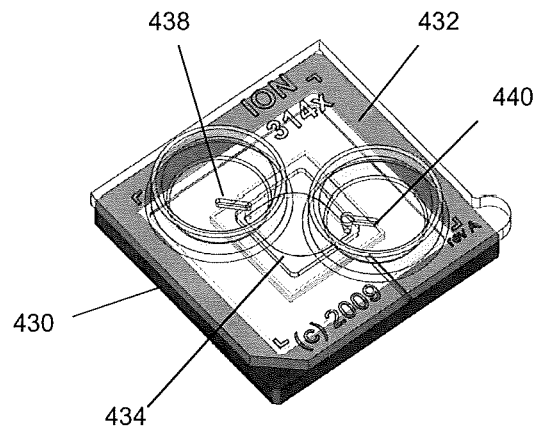
Figure 4D:
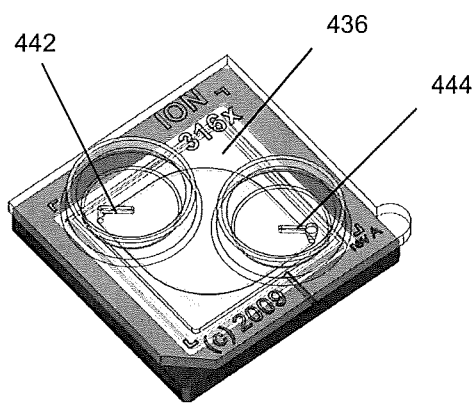

Flow cells may be assembled with a microwell array and sensor array in a variety of ways, such as disclosed in Rothberg et al, U.S. patent publication 2009/0127589 and Rothberg et al, U.K. patent application GB24611127, which are incorporated by reference. In one embodiment, illustrated in FIGS. 4A-4D, a flow cell (e.g., an embodiment of a sensor cartridge) is made by attaching a fluidic interface member to a housing containing a sensor chip. Typically, an integrated microwell-sensor array (i.e., a sensor chip) is mounted in a housing or package that protects the chip and provides electrical contacts for communicating with other devices. A fluidics interface member is designed to provide a cavity or flow chamber for reagents to pass through when it is sealingly attached to such packaging. In one aspect, such attachment is accomplished by gluing the pieces together. FIG. 4A shows a bottom view (or face) of component (400) (referred to below as a "rectilinear body") of a flow cell of the present teaching. In the illustrated embodiment, a complete flow cell is formed by attaching component (400) to a package containing a sensor array (as shown in FIGS. 4C and 4D). Ridge (401) is elevated from surface (413) and forms walls (410) of ellipsoidal flow chamber (408) when mated with chip (430) shown in FIG. 4C. Component (400) may be glued to chip housing (430) (referred to below generically as "rectilinear interface package") to form a fluid-tight seal. FIG. 4B shows a top view (or face) (416) of component or member (400) showing inlet and outlet collars (418) and (420) that permit the flow cell to be sealingly connected to a fluidic system. Inlet and outlet tubes connected to elastomeric annular members that are inserted into collars (418) and (420) so that the elastomeric material forms a seal along the floor and walls of collars (418) and (420). Other means of connecting a flow cell to a fluidics system may be used, including other types of pressure fittings, clamp-based fittings, screw-on fittings, or the like, which are design choices for one of ordinary skill. Component (400) may be adapted to accommodate different sized chips with a simple design change, as illustrated by passages (422) and (424). Namely, for a small array (434) shown in FIG. 4C, a passage having an opening at the center of inlet collar (418) and of outlet collar (420) may be directed by such passage towards the center of component or member (400) to an inlet port and outlet port over array (430). Likewise, for a large array (436), shown in FIG. 4D, similar passages (442 and 444) may be directed away from the center of component (400) and to the inlet and outlet of array (436). This has the advantage of providing a single basic flow cell design that can be used with multiple sensor array sizes. Protruding tab (412) and bevel (414) are employed to ensure correctly oriented placement of a chip into a complementary socket or appliance for making fluidic and electrical connections to the rest of the apparatus.

In one aspect, the present teaching includes a flow cell member (exemplified in FIGS. 4A and 4B) for forming a fluidics interface with sensor arrays of different rectilinear sizes disposed in a rectilinear interface package. Such a member comprises the following elements: (a) a rectilinear body having an upper face and a lower face and a shape matched with that of the rectilinear interface package so that the lower face of the rectilinear body may be bonded to the rectilinear interface package to form a fluid-tight enclosure for a sensor array, wherein an inlet is disposed at one end of the upper face, and an outlet is disposed at an opposite end of the upper face; (b) an inlet passage interior to the rectilinear body providing a fluid passage from the inlet to the fluid-tight enclosure forming an inlet port in the lower face of the rectilinear body positioned above and at one end of the sensor array; and (c) an outlet passage interior to the rectilinear body providing a fluid passage from the outlet to the fluid-tight enclosure forming an outlet port in the lower face of the rectilinear body positioned above and at an end of the sensor array opposite of that of the inlet port. In one embodiment, the inlet is concentrically disposed with an inlet collar in a corner of said upper face and said outlet is concentrically disposed with an outlet collar in a diagonally opposite corner of said upper face as said inlet and inlet collar. In another embodiment, the inlet and outlet collars each have a radius and wherein said inlet port and said outlet port are each positioned within perpendicular projections of the radii of said inlet and outlet collars, respectively, onto said lower face of said rectilinear body. In another embodiment, a plurality of fluid-tight enclosures are formed when a rectilinear body is bonded to a rectilinear interface package, as exemplified in FIG. 4E.

Figure 4E:
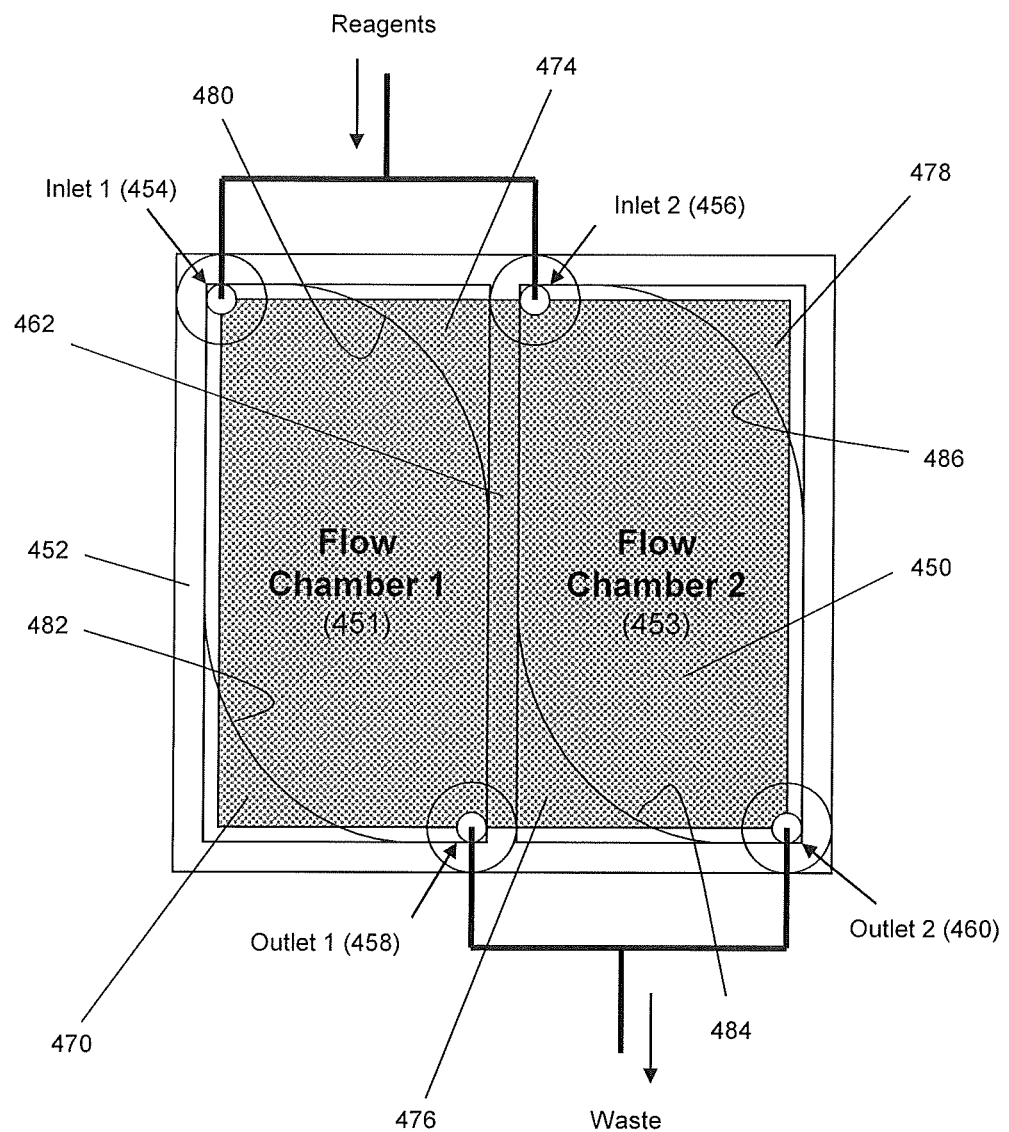
FIG. 4E shows a flow cell with two flow chambers integrated with a microwell-sensor chip.

FIG. 4E illustrates how the above design concepts may be used to make a plurality of separate flow cells using a single large sensor array. Fluidics interface member (462) mounts on and is sealingly attached to a housing (not shown) that holds sensor array (450) and defines two flow chambers (451) and (453), each having separate inlets (454 and 456, respectively) and separate diagonally opposed outlets (458 and 460, respectively) that are connected to a common source of reagents and to a common waste line, respectively. Interior walls (480, 482, 484 and 486) formed by attachment of fluidics interface member (452) to the chip housing defines the flow paths through flow chambers (451) and (453) and exclude opposing corner regions (470, 474, 476, and 478) from having contact with reagents passing through the flow chambers. Preferably, in embodiments employing floating gate FETs, sensors in corner regions (470, 474, 476, and 478) are pinned as described above. Likewise, sensors in the region defined by, or under, central partition (462) are also pinned so that they do not contribute to output signal noise of active sensors.

Flow cells and fluidic circuits of the present teaching (described below) may be fabricated by a variety of methods and materials. Factors to be considered in selecting materials include degree of chemical inertness required, operating conditions, e.g. temperature, and the like, volume of reagents to be delivered, whether or not a reference voltage is required, manufacturability, and the like. For small scale fluid deliveries, microfluidic fabrication techniques are well-suited for making fluidics circuits of the present teaching. For mesoscale and larger scale fluid deliveries, conventional machining techniques may be used to fabricate parts that may be assembled into flow cells or fluidic circuits of the present teaching. In one aspect, plastics such as polycarbonate, polymethyl methacrylate, and the like, may be used to fabricate flow cells and fluidics circuits of the present teaching.

Figure 5A:
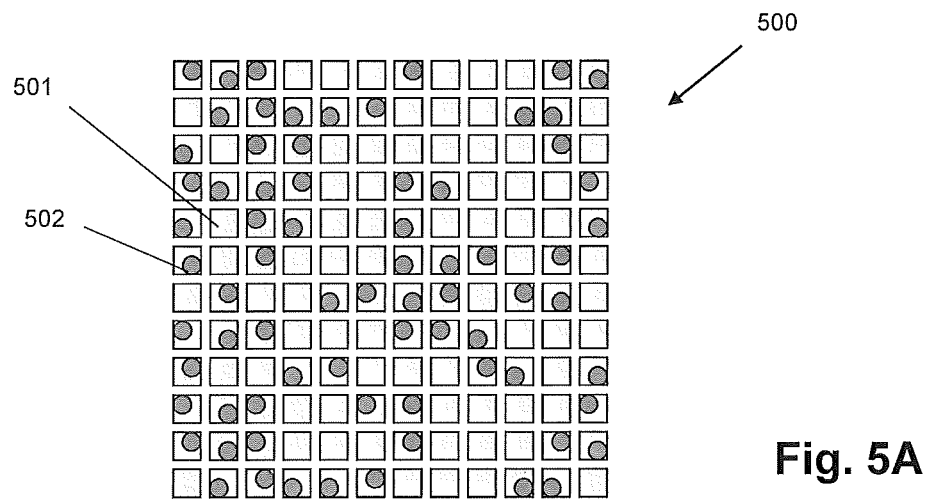
FIG. 5A illustrates analytes randomly disposed in microwells of a microwell array.
Figure 5B:
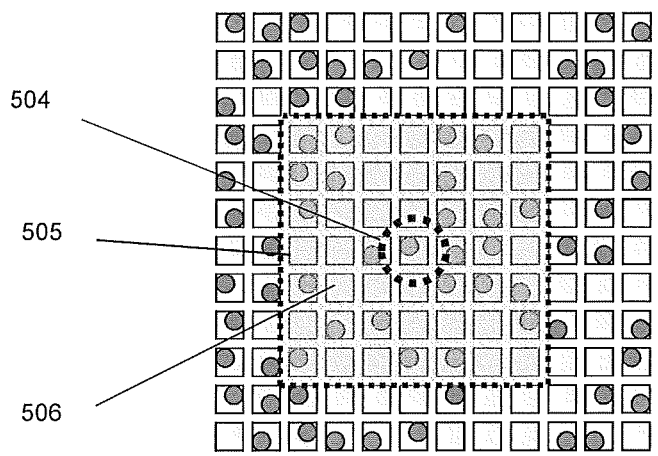
FIGS. 5B and 5C illustrate different ways of identifying empty microwells in the vicinity of a selected microwell.
Figure 5C:
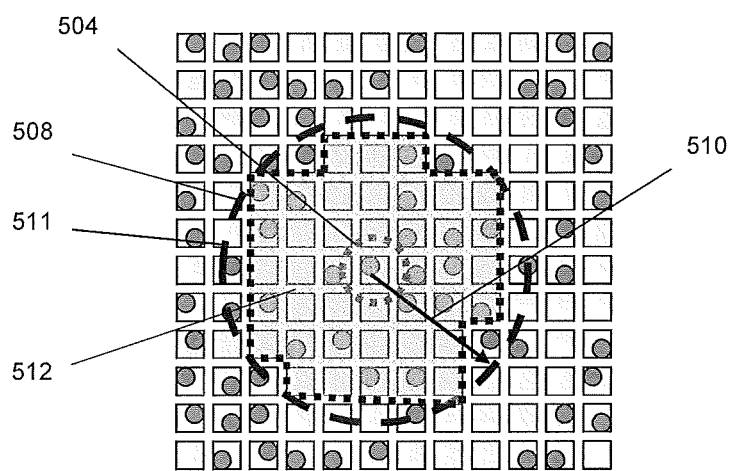

As mentioned above, analytes are randomly distributed in microwells of an array, as illustrated for array section (500) in FIG. 5A, where microwells either are empty (501) or contain analyte (502), such as a bead. Output signals collected from empty wells may be used to reduce or subtract noise in output signals collected from sensors of microwells containing analyte. Empty well output signals contain signal noise components common to all microwells within a local region of the array, so that such common noise components may be obtained from the empty well output signals and subtracted from the output signal of microwells with analyte using conventional signal processing techniques. In other words, output signals from wells containing analyte are improved by subtracting a component of noise determined from output signals of neighboring empty wells. In one aspect, a measure of such common noise is based on an average of output signals from multiple neighboring empty wells. As described more fully below in the case of DNA sequencing, the type of information used from neighboring microwells and how it is used may vary with nature of assays being carried out and measured. As used herein, the term "average" includes weighted averages, and functions of averages, for example, based on models of physical and chemical processes taking place in the microwells. Types of microwells used in the averages may be generalized in particular applications where, for example, further sets of microwells may be analyzed for further information on common noise, such as, in addition to empty wells, wells containing particles without analyte may be included, and so on. In one embodiment, time domain functions of average empty well noise may be converted to frequency domain representations and Fourier analysis, e.g. using fast Fourier transforms, may be used to remove common noise components from output signals from non-empty well. As mentioned above, the empty well signal subtracted in this manner may be an average of empty well signals of empty wells in the vicinity of a microwell of interest. The number and location of local empty wells for such computation may be selected and carried out in a variety of ways. Exemplary approaches for making such selections are illustrated in FIGS. 5B and 5C. In FIG. 5B, for each microwell containing analyte (504), a fixed region (506) may be defined by a 7×7 square (505) of microwells. In other embodiments, such a fixed region may vary in the range from 3×3 to 101×101, or in the range from 3×3 to 25×25. Selection of the size of such regions depends on several factors, including the degree of loading of analytes in microwells, the amount of time available for computing during a step, and the like. Returning to FIG. 5B, output signals from empty wells in region (506) are used in the above subtraction computation. Alternatively, a region of empty wells may be determined by distance from the microwell of interest, as illustrated in FIG. 5C. There fixed circular region (512) is defined by a distance (510) from the microwell of interest (504) and empty well signals from empty wells falling entirely within region (512), that is, in region (508), are used in the above subtraction computation. Not all of the empty well signals in a given region need be used. For example, when a microwell array is sparsely loaded with analytes or particles, e.g. less than 25 percent microwells being loaded, a portion of the empty wells in a defined region (e.g. 512) may be used for background subtraction. In one aspect, such portion or subset may be a randomly selected subset of available empty wells. In some circumstances it may be advantageous to use the least number of empty well output signals as possible in order to minimize computation time for determining output signals from non-empty wells. The area or number of wells selected for determining an average empty well signal may change according to the density of analytes in microwells. For example, the size of a local region may be selected depending on the availability of empty wells. If a minimum of N empty well output signals, e.g. 10, 20, or 30, must be measured to ensure a reliable representation of local noise, then a local region, e.g. (512), may be increased until such number is present. In one aspect, local noise subtraction using a fixed area is used whenever ninety-five percent or less of the microwells in an array contain analyte. In some embodiments, in addition to, or in lieu of empty wells, particles carrying analyte may be spiked with particles not carrying analyte and the background noise subtraction may be with respect to an average signal recorded for microwells containing analyte-free particles.

Instrumentation Systems/Electronics & Software
Leak Detection

In various embodiments, it may be desirable to detect anomalies within the system including for example leaks or misaligned components. A leak can occur for example as a result of operator error, or a flow cell leak. Such occurrences may arise for example if the operator releases a chip clamping mechanism from the chip during a run or where fluid may leak out of the flowcell due to a crack or faulty flow cell attachment. Detection of a valid connection between the chip and the instrument may desirably permit detection of such potential fault cases.

In one aspect, fault monitoring may be provided by the system software which may be configured to monitor the connection of the chip to the instrument. In various embodiments, such monitoring may be performed by measuring a value returned in the reference pixels while clocking the chip out. For example, if the chip loses connectivity to the instrument through a spacer or paraposer, the software may detect a loss of signal (e.g. no signals detected back on the reference pixels). Such an event may be configured to trigger an alarm or notice which may be brought to the attention of the user through a graphical user interface or audio alert. Furthermore the system can be configured to provide an automated response such as for example responding to an anomalous event by turning off the flow across the chip. In certain instances, a leak onto the paraposer or space surface may potentially affect measured values being returned on the reference pixels which may also be configured in software to trigger a notice event or automated response.

In an embodiment, a system receives a sensor cartridge that is engaged with a communications interface and a fluidic interface. Leak detection can be performed by monitoring a sensor of the sensor cartridge and detecting a leak based on characteristics of the sensor. In a particular example, the sensor is of a sensor array in fluid communication with a fluid subsystem. When a signal is lost from the sensor or the signal exhibits particular characteristics, fluid flow to the sensor cartridge can be stopped or an interface can be provided to a user. In an example, the interface includes an element or control operable by a user to override the fluidic subsystem.

In various embodiments, a fluidic interface system may be adapted for use with sample analysis devices that involves analyzing a liquid sample containing analytes of interest using one or more electronic sensors. In aspects, the electronic sensors comprise one or more electrical contacts which couple the sensor to other electronic components. A portion of the electronic sensor may be exposed to the liquid sample and it is desirable to insure that the liquid sample remain sequestered away from the other electronic components while at the same time providing electrical connectivity between the sensor and the other components. In an exemplary application using a chemFET array comprising a plurality of chemically sensitive or responsive sensors, the fluidic interface system should provide a mechanism to provide connectivity between the contacts on the chemFET array or sensor chip to contacts associated with a corresponding interconnect surface. The interconnect surface further provides electrical connectivity to ancillary electronic components while at the same time isolating them from potential sample liquid exposure or intrusion.

In other aspects of the present teachings, the fluidic interface system provides mechanisms to address or overcome warping, surface anomalies or other manufacturing imperfections of either the sensor array or the corresponding interconnect surface. In certain instances, imperfections or the like may result in the sensor array or corresponding interconnect surface to not position evenly or provide a non-uniform contact between the sensor array and the interconnect surface resulting in partial or improper connectivity between the two components.

A further feature of the fluidic interface system of the present teachings is that the device may be configured to be resistant to corrosion resulting from exposure to the liquid sample including potential galvanic corrosion that may occur for example between a chemFET sensor array and the electronic processing device adapted to receive or interact with the array. Susceptibility to corrosion may also be mitigated for the electrical contacts on the corresponding interconnect surface, which may result for example where one metal at the interface of electrical contact is fabricated from a different type of metal than that of the electrical contacts of the chemFET sensor or the electrical contacts of the corresponding surface.

As will be described in greater detail hereinbelow, applications of the present teachings are useful for providing a component capable of establishing a fluidic barrier or leak-proof electrical interface between chemFET sensors chips and ancillary electronic components. In various embodiments, the interface may be used to establish an electrical connection between contacts on a chemFET sensor chip and contacts on the corresponding surface (which electrically connects to ancillary electronic components). Such a component may further be configured to reduce or eliminate galvanic corrosion that might otherwise occur between the device and either the chemFET sensor chip or the electrical contacts on the corresponding surface.

Figure 9A:
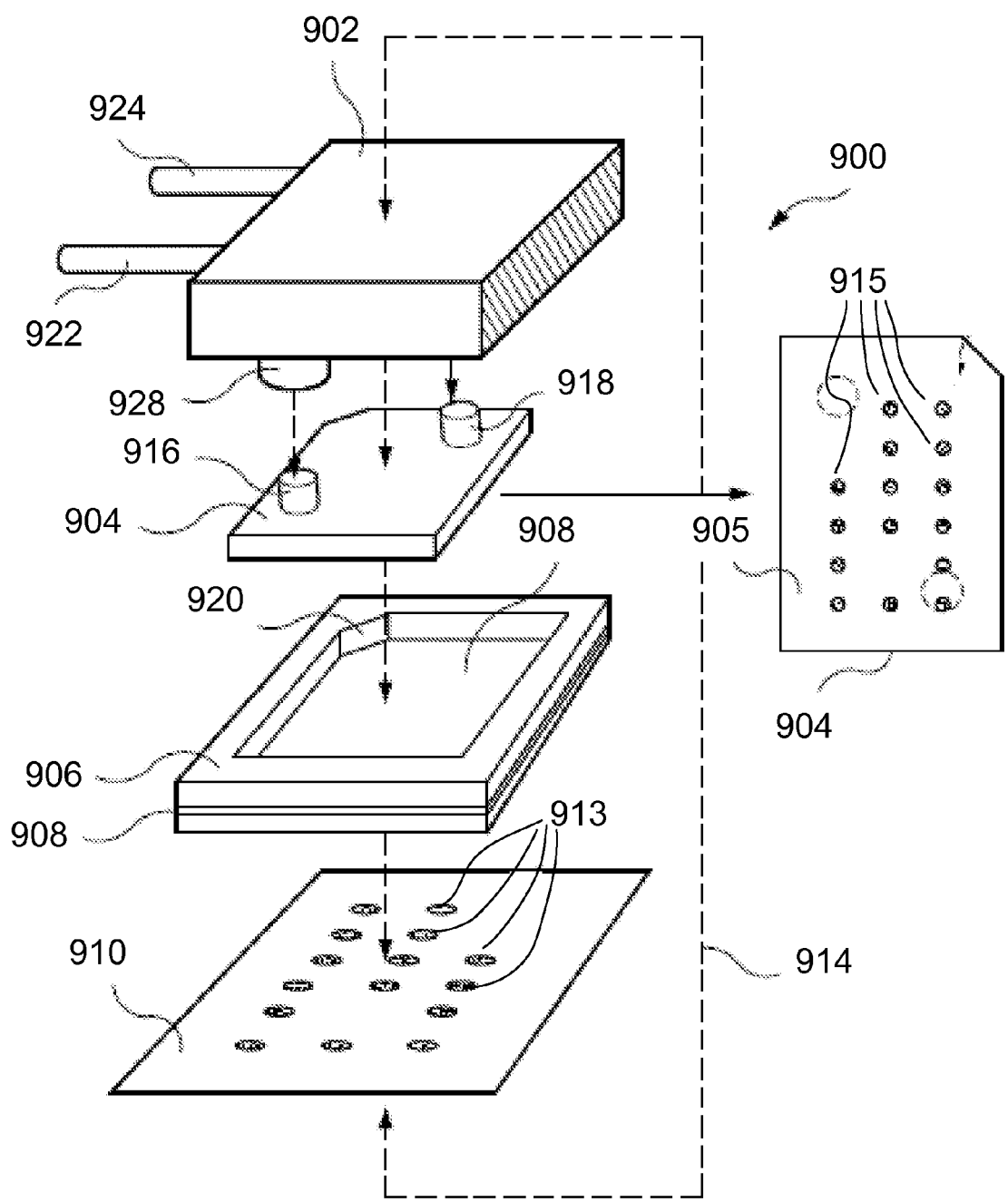
FIG. 9A includes an illustration of an exemplary clamp assembly.

One embodiment of the present teachings is illustrated in FIG. 9A. Elements of connector (900) include clamp member (902), socket (906) (e.g., an embodiment of a setting) containing anisotropic conducting membrane (908), surface (910) containing electrical contacts (913) to processing electronics (e.g., an embodiment of a communication interface), and forcing element (914) for providing a clamping action. Forcing or coupling element (914) urges clamp member (902) against sensor cartridge (904) which, in turn, is urged against anisotropic conducting membrane (908) which, in turn, provides one or more electrically conductive pathways between contacts (915) on the bottom of sensor cartridge (904) and corresponding contacts (913) of the processing electronics on surface (910). Forcing or coupling element (914) can be solely or partially mechanical (as exemplified below), electrically actuated via solenoids, motors, hydraulics, or operated in other ways manually and automatically as will be appreciated by one of skill in the art. In various embodiments, it is preferable for the forcing or coupling element (914) to urge by application of force or pressure evenly over sensor cartridge (904) so that the one or more conductive pathways between electrical contacts through membrane (908) are substantially uniformly engaged. Additionally, a uniform urging force may be desirable so that membrane (908) does not evidence localized wear or compression over time or through repeated use.

Figure 9B:
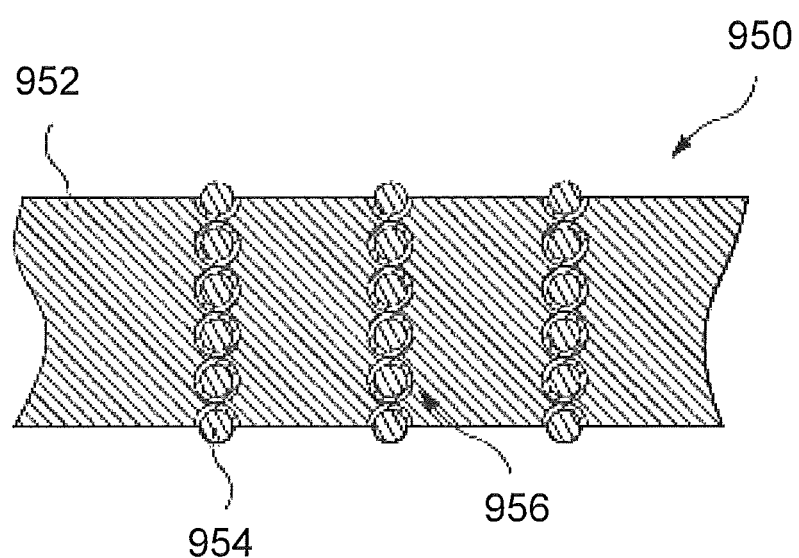
FIG. 9B includes an illustration of an exemplary anisotropic conductive membrane.

An example of an anisotropic conducting membrane or elastomer (908) is illustrated in FIG. 9B. In various embodiments, commercially available materials may be used to fabricate such conformable or elastomeric membranes (e.g. Paricon Technologies Corp. (Fall River, Mass.), which manufactures the PariPoser interconnection system and the like). In various embodiments, such membranes (950) may comprise an elastomeric material (952) in which columns (956) of conductive particles (954) are aligned substantially perpendicularly to the plane of the membrane. In such configurations, where electrical contacts touch opposing sides of the membrane, a conductive pathway is established between them. These electrical contacts may further be isolated from other contacts touching the membrane at other locations and may further provide connectivity for multiple independent electrical contacts based upon the configuration and orientation of the membrane. In accordance with various embodiments of the present teachings, the membrane may be fabricated from a material that is substantially impermeable or non-reactive to fluids and chemical components contained therein, particularly aqueous fluids and reagents associated with the sample analysis.

It will be appreciated that the materials used to form the membrane may be selected from a number of different materials as will be described in greater detail hereinbelow. Additionally, the dimensionality and thickness of the membrane can be tailored for specific applications or instrumentation. Likewise the inter-membrane connectivity may be provide by conductive materials other than beads and may be present in orientations other than that exemplified in FIG. 9B. For example, electrical connectivity through the membrane may result from flexible wires or traces which are aligned with the electrical contacts on the receiving or contacting surfaces of the membrane. In such instances, the membrane's conformability characteristics may allow deformation of portions of the membrane when engaged with the sensor cartridge or the processing electronics. The electrical conductivity is further preserved as the inter-membrane conductivity features are also tolerant to deformation of the membrane and thus may preserve conductive pathways between the surfaces of the membrane.

As previously described, the membrane may be advantageously used to provide electrical connectivity between desired components such as the sensor chip and processing electronics even where the electrical contacts or surface features of the components are not perfectly matched. For example, imperfections in the construction of the sensor cartridge (905) or the surface (910) can result in some of the contacts (915) of the sensor cartridge (904) and the corresponding contacts (913) of the processing electronics on surface (910) to not maintain good electrical conductivity or connectivity when positioned in proximity to one another due to partial contact or misalignment of at least a portion of the contacts. Additionally, the required urging force provided by the coupling element (914) may be reduced by use of the membrane which may aid in providing more uniform connectivity between the contacts rather than necessitating a relatively large urging force to conductively join each of the desired contacts. The reduction in urging force required further reduces the risk of damaging or breaking components within the system which might otherwise occur to establish the electrically connective pathways between components. Such damage might occur as a result of the force applied to insure connectivity between desired contacts or through repeated use or operation with multiple sensors. In certain instances, the membrane may also be used in situations where warping or deformation of the sensor cartridge or the corresponding contacts of the processing electronics may occur which cause either the sensor cartridge or surface (910) contacts to lie outside of a substantially 2-dimensional plane. As a result, without the membrane, some contacts between the sensor cartridge (915) and the surface (913) may not readily electrically connect when positioned substantially adjacent to one another in a desired orientation.

In one embodiment of the present teachings, the elastomeric material (952) of the membrane (950) is designed such that the elastomeric material (952) in combination with the forcing element (914) compensates for any imperfections in the construction of the individual components, such that electrical connections are established between desired contacts (915) on the sensor cartridge (904) and the corresponding contacts (913) of the processing electronics on surface (910). In another embodiment, either the surface (910) which contains the contacts (913) of the processing electronics, or the sensor cartridge (904) which contains the contacts (915) may be manufactured using flex circuit technology. In various embodiments, flex circuitry relates to technology for assembling electronic circuits by mounting electronic devices or components on at least partially flexible substrates (such as a flexible polymer, plastic, or nylon surface).

In another embodiment of the present teachings, either the contacts (915) on the sensor cartridge (904) or the contacts (913) of the processing electronics on surface (910) are selectively re-plated during manufacturing. With regard to the surface (910), the contacts (913) a portion or substantially all of the contacts may undergo a re-plating operation in order to alter the physical geometry of desired contacts so as to improve connectivity between components. In various embodiments, the re-plating operation may include creating thicker or taller contacts (913), capping the contacts, thinning or resizing the contacts, or performing other modifications to at least a portion of the contacts in order to obtain a desired height or profile for the electrical connections. The aforementioned re-plating operations may further be utilized in connection with the anisotropic conducting membrane (908) to establish positive or uniform connectivity of the contacts (915) on the bottom of sensor cartridge (904) with the contacts (913) of the processing electronics on surface (910). In various embodiments, the re-plating operations cause other areas besides the contacts (913) on the surface (910) to retain substantially their original height, profile, or thickness.

In an exemplary circuit board embodiment, selective re-plating may be accomplished by masking at least a portion of the circuit board that is not desirably re-plated and subsequently passing the circuit board through the plating process thereby preserving the surface features or contour of contacts or surfaces that have been masked. In another embodiment of the present teachings, the conducting membrane (908) may be comprised of interspersed areas of conductive and non-conductive material such as a polymer, plastic, nylon, silicone, glass or other material. The conducting membrane may further comprise one or more columns of conductive material such as metal impregnated or conductively modified polymer, nylon, silicone, or other suitable material or mixtures thereof in selected areas to contact, join, or mate the contacts (915) on the bottom of sensor cartridge (904) and the corresponding contacts (913) of the processing electronics on surface (910). In various embodiments, the column may be substantially perpendicularly aligned to the plane of the membrane. The conductive column may create or establish a desired or uniform electrical connection from the top to the bottom of the membrane (908), similar to the columns (956) of conductive particles (954). The conducting membrane (908) may further comprise portions of non-conductive or insulating material (e.g. polymer, nylon, silicone, glass, or other suitable material or mixture thereof) in areas between the different contacts (915) on the bottom of sensor cartridge (904), to reduce or eliminate undesired cross-talk or conductivity between contacts (915) on the bottom of sensor cartridge (904). In accordance with the present teachings, the membrane may be manufactured such that it is impermeable to or resilient to fluids, particularly aqueous fluids and reagents/chemicals which might come into contact with the membrane.

In various embodiments, it may be desirable to prevent oxidation or galvanic corrosion of selected components within the system. Such oxidation or galvanic corrosion may occur for example between the electrical contacts (915) on the bottom of sensor cartridge (904) and the anisotropic conducting membrane (908), or the electrical contacts (913) of the processing electronics on surface (910) and the anisotropic conducting membrane (908). In certain embodiments, the anisotropic conducting membrane (908), the contacts (915) on the bottom of sensor cartridge (904), and the contacts (913) of the processing electronics on surface (910) may be fabricated from or coated with substantially the same or similar metal or formed to create conductive surfaces of compositions which are compatible or resistant to oxidation or galvanic corrosion. In one such embodiment, the contacts (915) on the bottom of sensor cartridge (904) and corresponding contacts (913) of the processing electronics on surface (910) may be gold-plated with the columns (956) of conductive particles (954) in the anisotropic conducting membrane (908) also being gold-plated. In such instances, gold-plating the columns (956) of conductive particles (954) in the anisotropic conducting membrane (908) may aid in reducing oxidation or galvanic corrosion which might otherwise occur between the membrane (908) and the contacts (915) on the bottom of sensor cartridge (904), or the membrane (908) and the contacts (913) of the processing electronics on surface (910). In additional to coating with gold, it will be appreciated that other coatings or materials may be used to confer the desired resistance to oxidation or corrosion. Thus, other metals or conductors may be used to confer a desired oxidation or corrosion resistant property. In certain embodiments, the existing material used to form the conductor may be chemically altered or modified directly rather than coated with a different material.

Returning to FIG. 9A, clamp member (902) may comprise conduits (922 and 924) and passages (not illustrated) for transferring fluid through fluid connectors (exemplary element 928 shown) into and out of sensor cartridge (904) through inlet (916) and outlet (918) when in a clamp-closed configuration. In addition to providing a fluidic connection, when in such configuration or position, sensor cartridge (904) may be forced or urged onto conducting membrane (908) to establish, creates, or maintain conductive pathways between contacts (915) on the bottom of senor cartridge (904) and corresponding processing electronics contacts (913) on surface (910).

Other embodiments of the present teachings are illustrated in FIGS. 10A-10G. Selected embodiments may include features such as: Substantially the same action or force associated with the clamp (1000) may provide both electrical connectivity and fluid port sealing with respect to the chip (1002). The clamp design may also protect underlying electronics components within the system such as a PC board containing processing electronics from fluid spills or reagent/liquid contamination. Furthermore, a lever or actuator (1008) may be provided with a substantially high mechanical advantage or a retention feature to engage the sensor chip (1002) in a clamped position and secured position. Furthermore, a compression-spring mechanism (1022) may be provided in connection with the clamping mechanism to at least partially reduce the required clamping energy or to facilitate urging of the various components together. To facilitate fluidic engagement with the sensor chip (1002) tapered fluid-port bosses or receivers may be utilized to facilitate engagement of the fluidic ports and provide a self-aligning feature for the fluid connections. These fluid-ports may further comprise elastomeric seals or gaskets (exemplified in FIG. 10C) to further enhance or improve the sealing or leak resistance of the system.

In various embodiments, a mechanically floating fluid manifold may be provided that at least partially self-aligns for example in X & Y directions. In various embodiments, the manifold may also be configured so as to possess an angular float to allow substantially equivalent forces to be applied to each of the fluidic seals or ports. Certain configurations also provide for fluidic seals that permit or direct a substantially lateral flow path so that various sizes, profiles, or configurations of sensors or flowcells can be accommodated. Additionally, the clamping mechanism may provide accessibility to desired components by its movable or pivoting orientation. For example, the clamping mechanism may be configured so as to open by pivoting sufficiently to provide access to the top of the sensor or flowcell to permit desired operations such as fluidic/reagent introduction or withdrawal. (See exemplary positioning of the clamping mechanism shown in FIGS. 10A-10G) These operations may include manual activities such as pipetting into the flowcell ports which may be made accessible to the user when the clamping mechanism is in the open position. Furthermore, the sensor or flowcell ports may be designed to accept, mate with or seal with components having standardized dimensions (such as a 1 mm outer diameter tapered pipette tip).

Figure 10A:
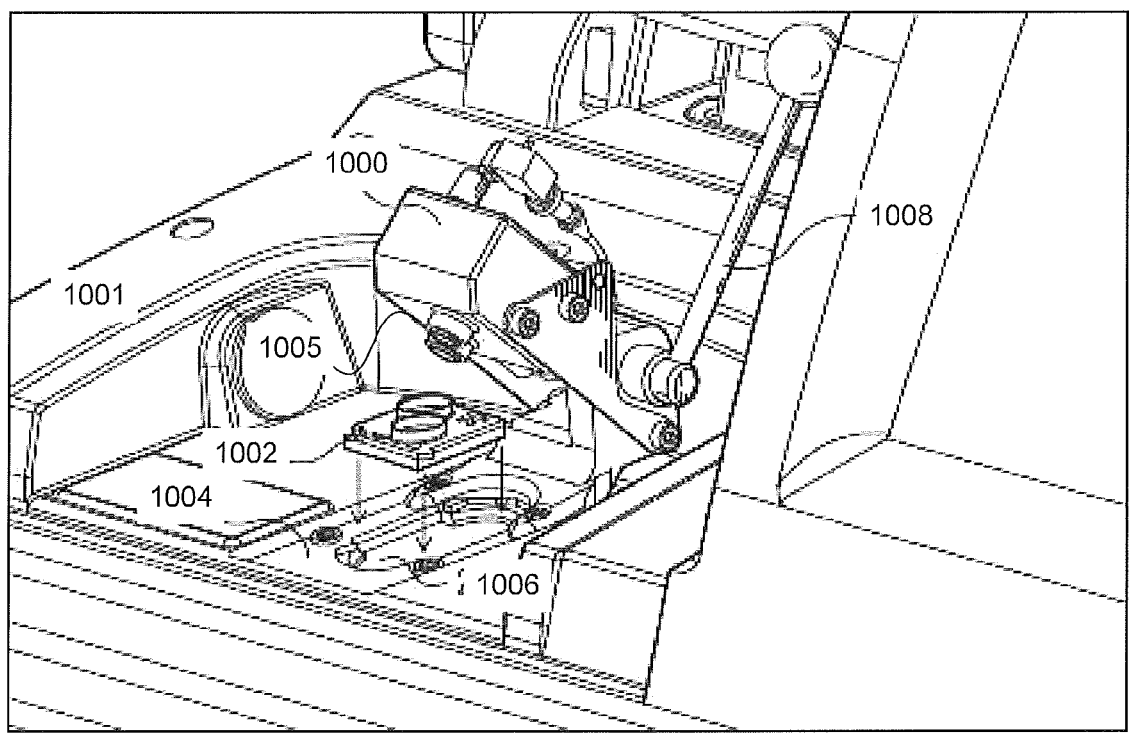
FIGS. 10A-10G include illustrations of an exemplary clamp assembly.

As exemplified in FIG. 10A, clamp member (1000) may be positioned in a substantially open position allowing positioning of the sensor or flowcell (1002) within or removal from the instrument (1001). Likewise, as previously discussed when clamp member (1000) resides in the substantially open position additional operations such as manual fluidic operations may be performed on the sensor or flowcell (1002). The clamp member (1000) may further be operationally associated with a mechanical forcing element comprising a spring-actuated self-locking mechanism operated by lever (1008). One embodiment of such a mechanism is exemplified in FIGS. 10A-10G where the actuator (1008) operates in connection with a compression spring assembly (1022) such that in the closed position the assembly may be "locked" into position to insure positive fluidic or electrical connectivity. In other embodiments, the mechanical forcing element may comprise an automatic or electrically operated component such as a servo driven actuator which applies a suitable force to actuate and position the clam member (1000) as desired. Clamp member (1000) (e.g., an embodiment of a manifold) may also include fluidics connectors (1005) for delivering reagent to sensor cartridge (1002). In the Figure, the sensor cartridge is shown suspended under clamp member (1000) and above socket (1004) depicting an exemplary relative positioning of the components with respect to one another. In the illustrated embodiment, anisotropic conducting membrane (1006) is shown at the base of socket (1004) (e.g., an embodiment of a setting) and provides desired alignment and connectivity for the sensor cartridge (1002) with the instrument (1001) as described previously. It will be appreciated that the membrane (1006) may be positioned in a number of manners such as being integrated into or attached to a surface of the sensor cartridge (1002) and not necessarily limited to those depicted in the illustrations.

Figure 10B:
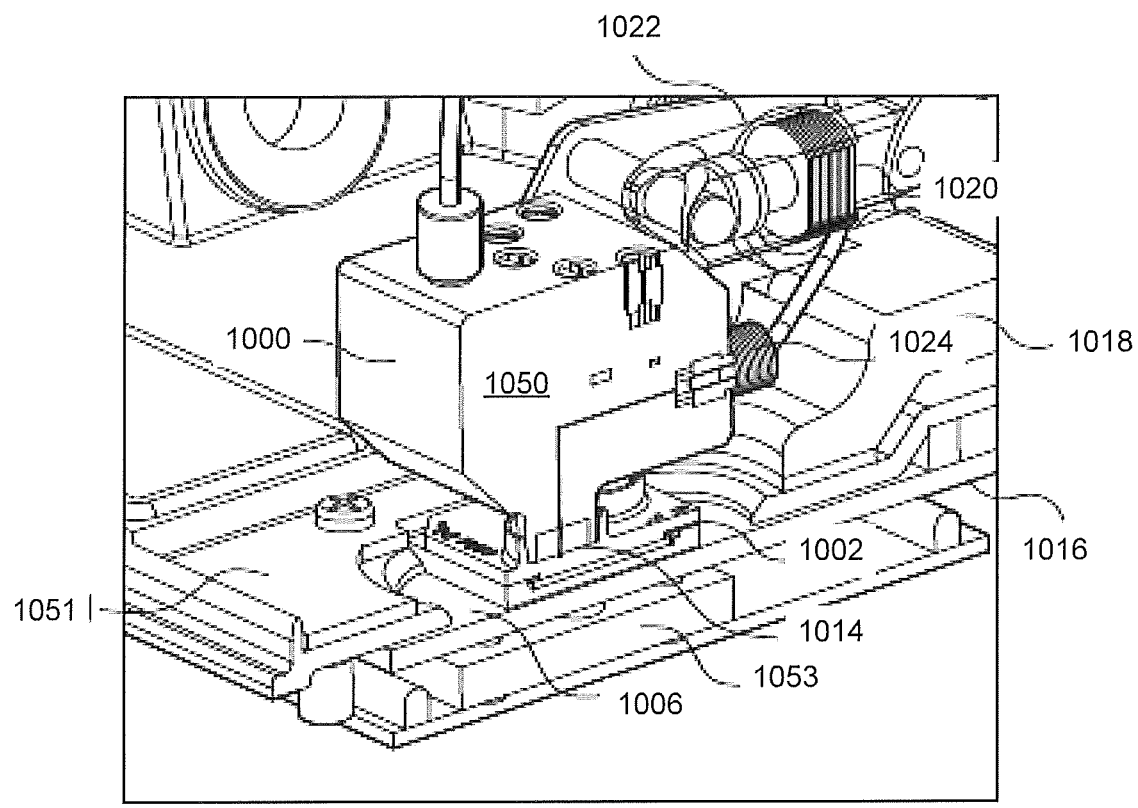

FIG. 10B illustrates a cut-away view of the device of FIG. 10A with the clamp member shown in a substantially closed position. Clamp member (1000) may be configured to retain the sensor cartridge (1002) (also referred to as the "flowcell or chip assembly") and firmly urge the cartridge (1002) against anisotropic conducting membrane (1006) (also referred to as "silicone ball-wire interposer"). Clamp member (1000) may be operationally associated with spring actuated mechanism (1022) (also referred to a "compressible spring assembly") for generating a substantially evenly distributed downward force onto clamp member (1000) and through contact sensor cartridge (1002). Clamp member (1000) further serves as a fluid manifold for delivering reagents to and from sensor cartridge (1002) through conduit (1024) and other conduits not shown.

Figure 10C:
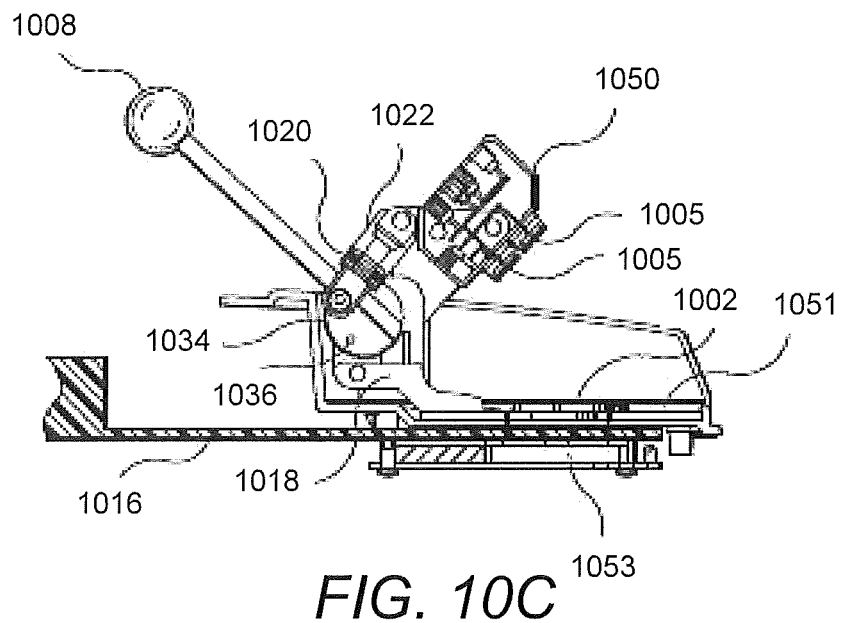
Figure 10D:
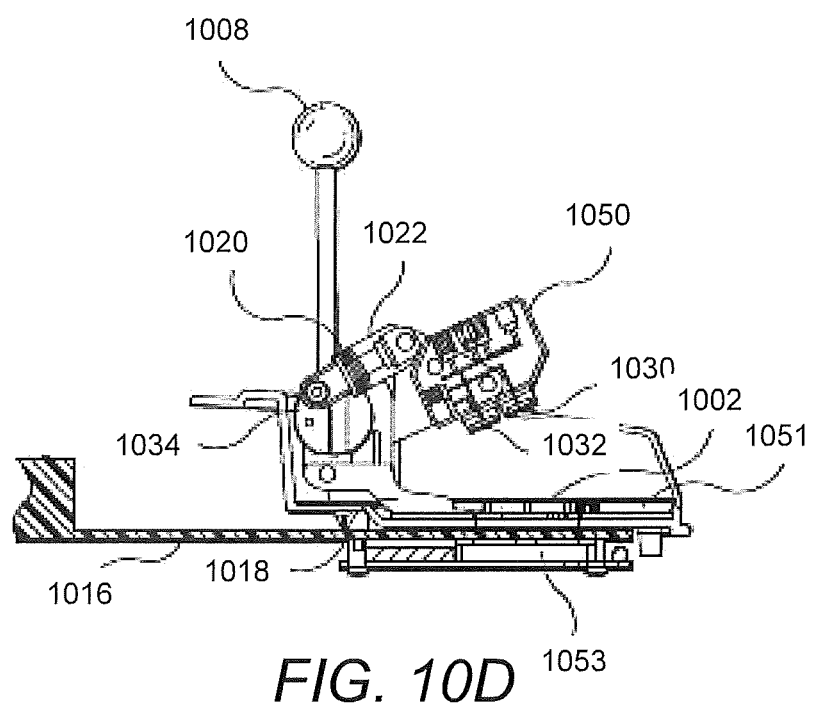
Figure 10E:
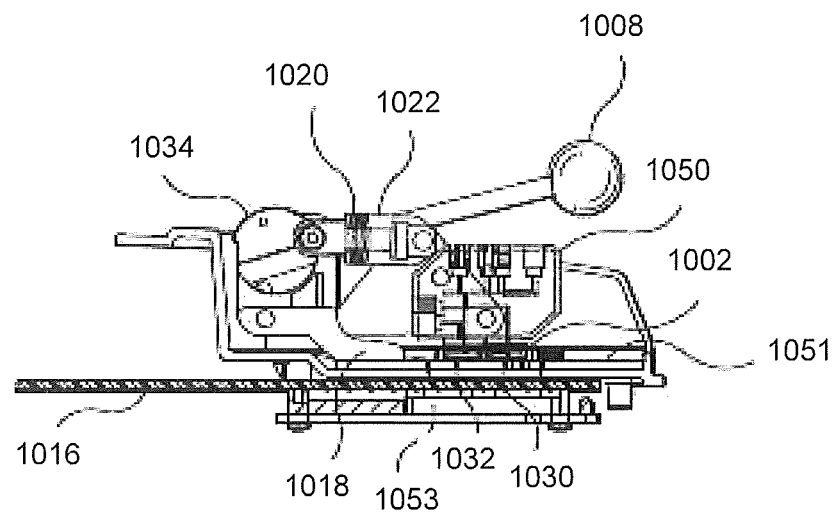
Figure 10F:
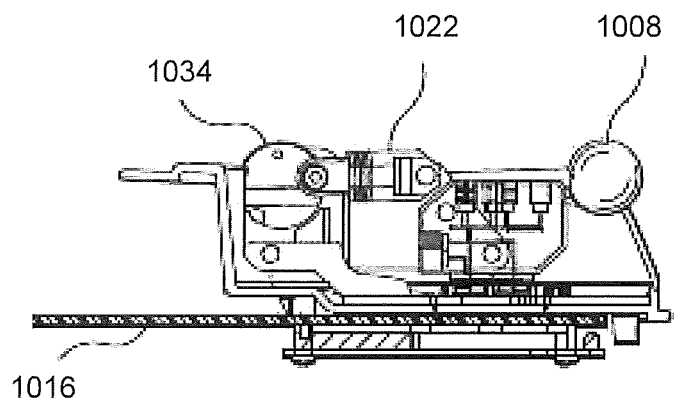
Figure 10G:
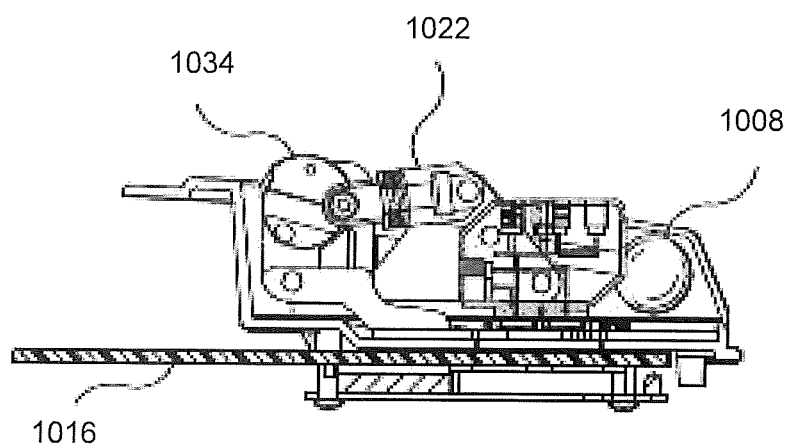

FIGS. 10C-10G show further operational embodiments of the present teachings using an exemplary manual actuator assembly for imparting the urging and positioning force to the instrument assembly which retains the sensor array or flowcell (1002). As previously discussed, the configuration of the components for retaining the flowcell (1002), the flowcell configuration itself, and the mode of imparting position or securing force to the flowcell (1002) may be modified as desired, for example using an automated actuator assembly versus a manual actuator without departing from the scope of the present teachings. Likewise, while a singular flowcell is depicted in the Figures, the system may be designed to accommodate multiple flowcells as desired. As shown in FIG. 10C, the chip clamp (1000) may be positioned in an open position through the use of the actuator assembly or lever (1008) to disengage the fluid manifold (1050) and associated fluid transfer ports (1005) from the flowcell (1002). The fluid transfer ports (1005) may comprise elastomeric seals positioned in a manner so as to engage with one or more mating or complementary ports on the flowcell (as shown in FIG. 10A) to provide a substantially fluid-tight or leakproof seal when the chip clamp resides in a closed position. Additionally, various structural enhancements may be included within the system such as a stiffener (1051) or back-up plate (1053) to improve the structural integrity of the mechanism. In various embodiments, such features may be used to provide a substantially rigid surface to engage the flowcell (1002) aiding in maintaining a desired position or profile of the flowcell (1002).

The step-wise operation and positioning of the various components illustrated in FIGS. 10C-10G depict one possible operational embodiment for securing the flowcell and engaging the fluidic and electronic components. The configuration and components as illustrated provide a "self-locking" feature such that the flowcell (1002) may be retained in a selected position with sufficient force to urge the appropriate electrical and fluidic contacts and connections providing a substantially leak-free system with good electrical connectivity. It will be appreciated that other configurations may be also used or adapted based on the preference or requirements of the system. For example, as previously described operation of the spring actuated clamp (1022) may be controlled by lever (1008) or an automated actuator assembly such as a motor or servo-driven mechanism without departing from the scope of the present teachings.

A fluid manifold 1050 includes ports, such as port 1024 for access to the remainder of the fluidic subsystem and includes ports 1005 to engage the sensor cartridge 1002. The ports 1005 can include elastomeric seals illustrated as 1014 in FIG. 10B.

A compressible spring assembly 1022 can provide force against the fluid manifold 1050 to secure the sensor cartridge 1002 in place and against the conductive membrane 1006. The assembly 1022 can include springs, such as compression spring wave washers 1020.

The clamp body 1018 can be disposed over a stiffener plate 1051 overlying a circuit board 1016. A backup plate 1053 can provide support to the circuit board 1016 by providing an opposing force to that applied by the fluid manifold 1050. As illustrated in FIG. 10C-10G, a joint 1034 can be activated by actuator 1008 to move the spring assembly 1022 and thus motivate the fluid manifold 1050 toward the sensor cartridge 1002.

In an embodiment, the system includes a setting, such as a socket, to engage a sensor cartridge and align the sensor cartridge with a communications interface, such as the contact pad or anisotropic conductive membrane. A fluidics subsystem can engage the sensor cartridge, such as through a manifold. The fluidic subsystem provides reagent flow to the sensor cartridge. The communication interface is communicatively coupled to a computational circuitry, such as a signal analysis circuitry, a fluid control system, or a combination thereof. The computational circuitry receives a signal from the sensor cartridge via the communications interface and monitors or analyzes the sensor signal. A leak can be detected based on a characteristic of the sensor signal. In response to detecting a leak, the computational circuitry can change or stop flow of the fluidic subsystem.

In an example, the sensor cartridge includes an array of sensors. The sensors can be chemical sensitive sensors, such as ion sensitive sensors. In particular, the sensors can be ion sensitive field effect transistors (ISFET). In another example, one or more sensors of the sensor array can be temperature sensors, flow sensors, pressure sensors, or any combination thereof.

In an example, the sensor signal monitored by the computational circuitry to detect leaks can be associated with a reference sensor. In particular, the reference sensor may be an ion sensitive sensor of an array of ion sensitive sensors. In another example, the sensor can be a temperature sensor. Alternatively, the sensor can be an electronic component, such as an electrode, capacitor, a transistor, or combination thereof, designed to generate a signal having a particular characteristic.

The computational circuitry can detect a leak based on a change in a characteristic of the sensor signal. For example, the characteristic may include the presence or absence of the signal. Detecting a leak may include detecting an absence of the signal. In another example, the characteristic can include a noise characteristic. For example, the noise characteristic can include a detection of line noise, such as a 60 Hz signal, noise resulting from crosstalk from one or more sensors, or combination thereof. In a further example, the characteristic can include a value of the sensor signal, and detecting a leak can include detecting a change in value that crosses or is beyond a designated threshold. For example, a leak may result in the sensor signal value being beyond a reasonable value based on the physical system. For example, a temperature measurement may exceed the boiling point of water or may be below the freezing point of water. In another example, an ion sensitive sensor to detect pH can indicate a pH of extreme acidity or alkalinity.

In response to detecting a leak, the computational circuitry may direct the fluidic subsystem to stop flow, redirect flow or in general, prevent flow from or to the sensor cartridge. For example, the computational circuitry may direct the fluidic system to cease flow to the sensor cartridge, while initiating flow of a rinse solution throughout the remainder of the fluidic subsystem. In another example, the computational circuitry can direct the fluidic subsystem to stop flow of each of the reagent solutions. In a further example, the computational circuitry can direct the fluidic subsystem to redirect any flow away from the sensor cartridge into a waste receptacle.

Figure 11:
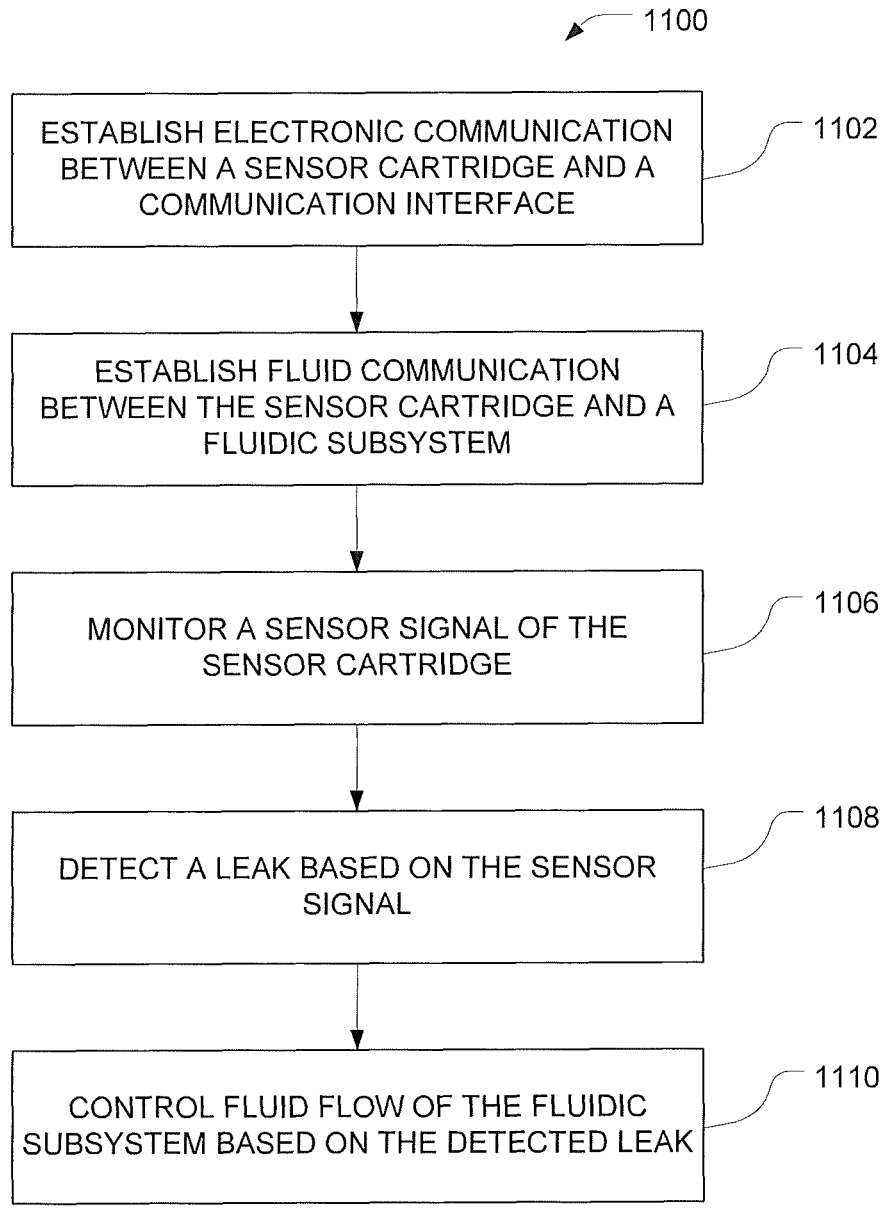
FIG. 11 includes a block flow illustration of an exemplary method.

FIG. 11 illustrates an exemplary method 1100 for controlling fluid flow within the system. As illustrated at 1102, electronic communication can be established between the sensor cartridge and a communication interface of the system. For example, the electronic cartridge can be positioned within a setting or socket and aligned with the communications interface, such as a contact pad or an anisotropic conductive membrane.

In addition, fluid communication can be established between the sensor cartridge and a fluidic subsystem, as illustrated at 1104. For example, a manifold of the fluidic subsystem can engage the sensor cartridge. The sensor cartridge can include inlet and outlet ports to be engaged by the manifold of the fluidic subsystem.

Computational circuitry can monitor a sensor signal the sensor cartridge, as illustrated at 1106. For example, a computational circuitry can monitor the sensor signal of an active sensor or of a reference sensor of the sensor cartridge via the communications interface.

Further, the computational circuitry can detect a leak based on the sensor signal, as illustrated at 1108. For example, the computational circuitry may detect a change in characteristic of the sensor signal, such as a loss of signal, a change in noise within the signal, or change in value of the signal. Noise can include line noise or crosstalk from another sensor signal. In another example, detecting a leak can include detecting a change in value of the sensor signal beyond a threshold.

As illustrated at 1110, the computational circuitry can control fluid flow of the fluidic subsystem based on the detected leak. For example, the computational circuitry may direct the fluidic subsystem to redirect flow away from the sensor cartridge and to stop flow or flow a rinse solution through the remainder of the fluid subsystem. Further, the computational circuitry can initiate user interfaces to provide an indication of the detected leak and provide an option to override control of the fluidic subsystem.

Portions of the method illustrated in FIG. 11 can be implemented through computer operable instructions and stored in a non-transitory medium.

While the present teaching has been described with reference to several particular example embodiments, those skilled in the art will recognize that many changes may be made thereto without departing from the spirit and scope of the present teaching. The present teachings are applicable to a variety of sensor implementations and other subject matter, in addition to those discussed above. It will be understood that the conformable conductive membrane configurations described above may be adapted for use with components other than flowcells in which an electrically conductive fluid-tolerant connection/or coupling is desirable. Additionally, the number of discrete electrical contacts which are to be coupled may vary widely in number from as little as one to hundreds, thousands, millions, or more connections. Other configurations of membrane connections may also be established including "sandwiching" a desired component between two or more membranes or partially or completely enclosing or encapsulating the desired component within or about the membrane to achieve the desired positioning, coupling, or connectivity effects. Similarly, the membrane may be formed as an integrated member of the desired component or fashioned in shapes or structures other than as a substantially flat or planar membrane to achieve a desired positioning, coupling, or connectivity.

As used herein, "microfluidics" devices or components, "fluidics" device or components, "fluid transfer" devices or components may comprise integrated systems having one or more chambers, ports, or channels that may be interconnected and/or in fluid communication with various other components within the system. These components may further be designed for containing, transporting or carrying out one or more analytical reactions or process, either alone or in cooperation with an appliance or instrument that provides additional support functions, such as sample introduction, fluid or reagent driving or delivery features, temperature control mechanisms, sample or analyte detection systems, data collection, data processing or data integration systems, and the like. The aforementioned devices may further include valves, pumps, conduits and other fluid transfer or fluid containment components with functional coatings or treatments applied, such as for example specialized coatings on the interior walls to substantially reduce or prevent adsorption of sample components or reactants, to facilitate reagent movement by electro-osmosis, or to impart other desired effects or properties. Such devices may be fabricated in or as a solid or formed substrate, which may be for example glass, plastic, or other polymeric materials, and may have an at least partially planar format or surface for facilitating detecting or monitoring sample and reagent movement, especially via optical or electrochemical methods.

Features of the aforementioned devices may have cross-sectional dimensions of less than a few hundred square micrometers and passages may have capillary dimensions, e.g. having cross-sectional dimensions of from about 500 μm to about 0.1 μm although other dimensionalities may be utilized readily as well. Microfluidics devices may have volume capacities in the range of from about 1 μL to a few nL, e.g. 10-100 nL although other volumes may be utilized readily as well.

System for Nucleic Acid Sequencing

Figure 6A:
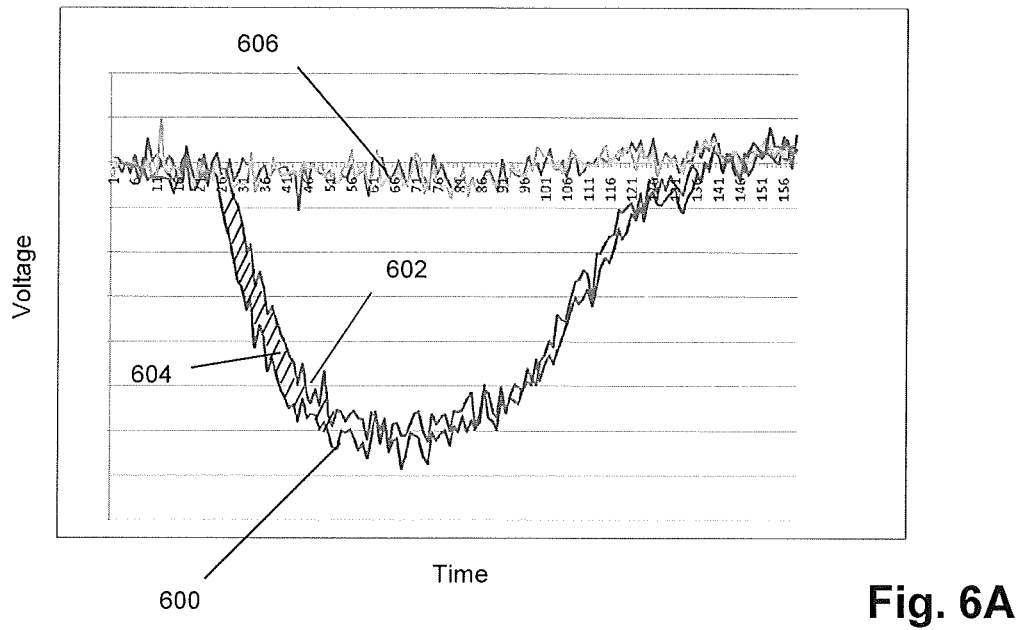
FIGS. 6A-6F illustrate the use of signals from local microwells to reduce noise in an output signal of a sensor of a selected microwell.
Figure 6B:
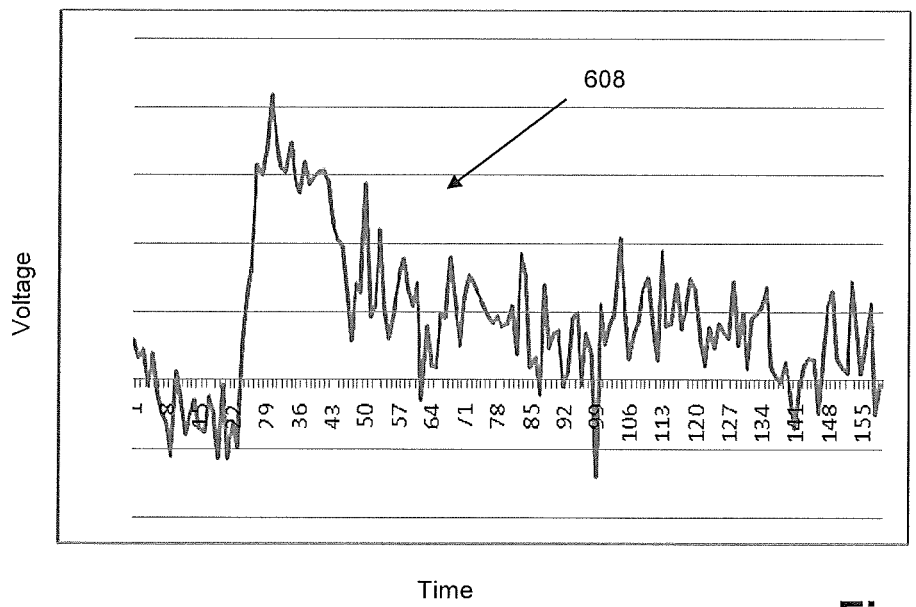
Figure 6C:
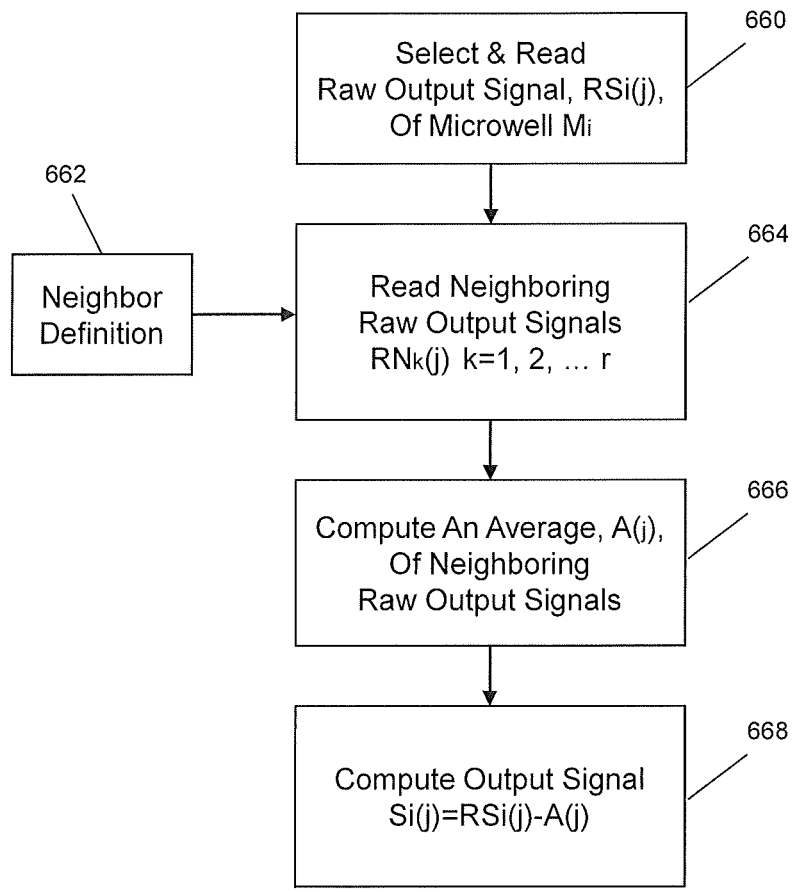
Figure 6D:
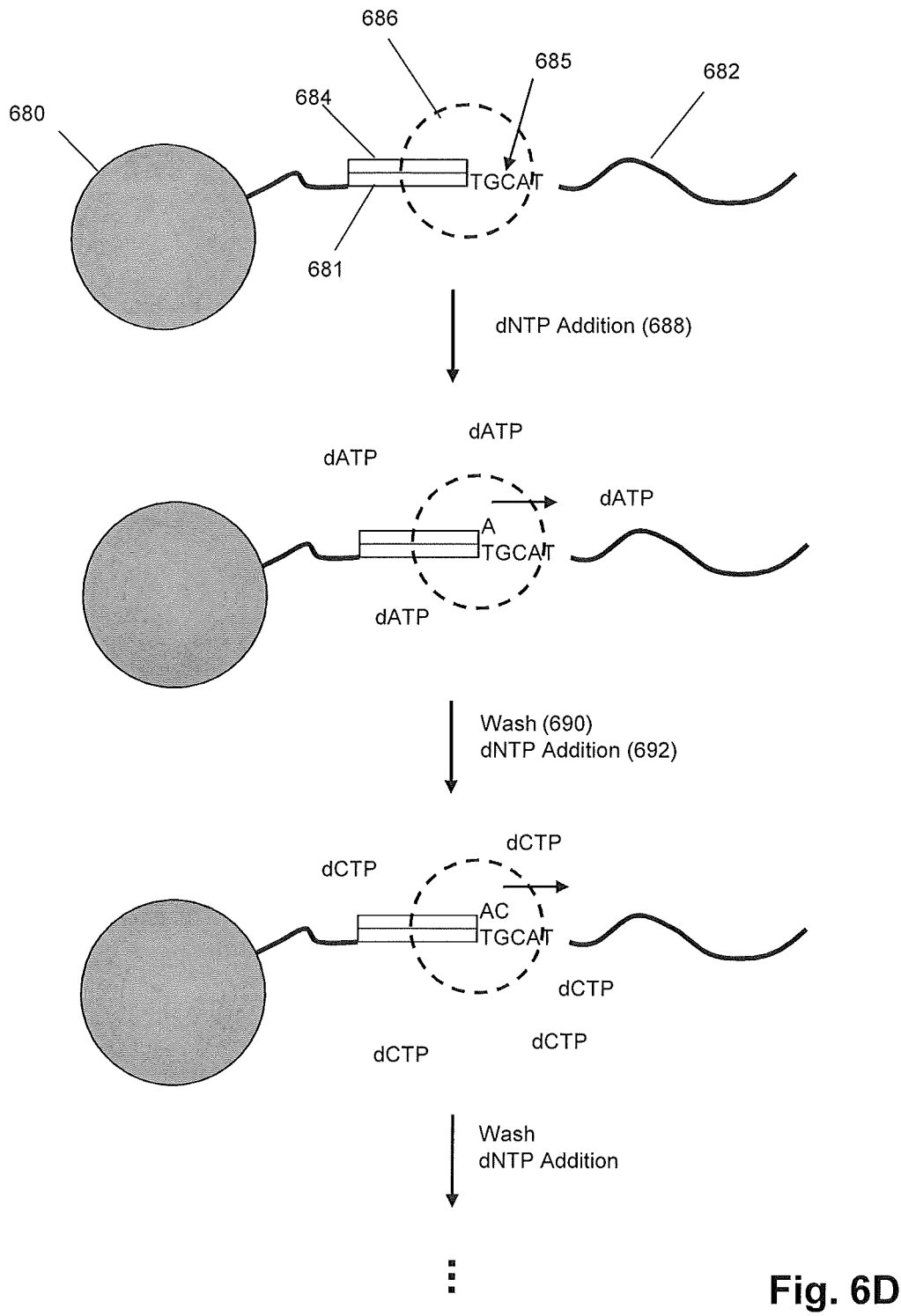

In one aspect, the present teaching provides methods and apparatus for carrying out label-free DNA sequencing, and in particular, pH-based DNA sequencing. Briefly, in pH-based DNA sequencing, base incorporations are determined by measuring hydrogen ions that are generated as natural byproducts of polymerase-catalyzed extension reactions. In one embodiment, templates each having a primer and polymerase operably bound are loaded into reaction chambers (such as the microwells disclosed in Rothberg et al, cited above), after which repeated cycles of deoxynucleoside triphosphate (dNTP) addition and washing are carried out. In some embodiments, such templates may be attached as clonal populations to a solid support, such as a microparticle, bead, or the like, and such clonal populations are loaded into reaction chambers. For example, templates may be prepared as disclosed in U.S. Pat. No. 7,323,305, which is incorporated by reference. As used herein, "operably bound" means that a primer is annealed to a template so that the primer's 3' end may be extended by a polymerase and that a polymerase is bound to such primer-template duplex, or in close proximity thereof so that binding or extension takes place whenever dNTPs are added. In each addition step of the cycle, the polymerase extends the primer by incorporating added dNTP only if the next base in the template is the complement of the added dNTP. If there is one complementary base, there is one incorporation, if two, there are two incorporations, if three, there are three incorporations, and so on. With each such incorporation there is a hydrogen ion released, and collectively a population of templates releasing hydrogen ions changes the local pH of the reaction chamber. The production of hydrogen ions is monotonically related to the number of contiguous complementary bases in the template (as well as the total number of template molecules with primer and polymerase that participate in an extension reaction). Thus, when there is a number of contiguous identical complementary bases in the template (i.e. a homopolymer region), the number of hydrogen ions generated, and therefore the magnitude of the local pH change, is proportional to the number of contiguous identical complementary bases. (The corresponding output signals are sometimes referred to as "1-mer", "2-mer", "3-mer" output signals, and so on). If the next base in the template is not complementary to the added dNTP, then no incorporation occurs and no hydrogen ion is released (in which case, the output signal is sometimes referred to as a "0-mer" output signal.) In each wash step of the cycle, an unbuffered wash solution at a predetermined pH is used to remove the dNTP of the previous step in order to prevent misincorporations in later cycles. Usually, the four different kinds of dNTP are added sequentially to the reaction chambers, so that each reaction is exposed to the four different dNTPs one at a time, such as in the following sequence: dATP, dCTP, dGTP, dTTP, dATP, dCTP, dGTP, dTTP, and so on, with each exposure followed by a wash step. The process is illustrated in FIG. 6D for template (682) with primer binding site (681) attached to solid phase support (680). Primer (684) and DNA polymerase (686) operably bound to template (682). Upon the addition (688) of dNTP (shown as dATP), polymerase (686) incorporates a nucleotide since "T" is the next nucleotide in template (682). Wash step (690) follows, after which the next dNTP (dCTP) is added (692). Optionally, after each step of adding a dNTP, an additional step may be performed wherein the reaction chambers are treated with a dNTP-destroying agent, such as apyrase, to eliminate any residual dNTPs remaining in the chamber, which may result in spurious extensions in subsequent cycles.

In one embodiment, a sequencing method exemplified in FIG. 6D may be carry out using the apparatus of the present teaching in the following steps: (a) disposing a plurality of template nucleic acids into a plurality of reaction chambers disposed on a sensor array, the sensor array comprising a plurality of sensors and each reaction chamber being disposed on and in a sensing relationship with at least one sensor configured to provide at least one output signal representing a sequencing reaction byproduct proximate thereto, and wherein each of the template nucleic acids is hybridized to a sequencing primer and is bound to a polymerase; (b) introducing a known nucleotide triphosphate into the reaction chambers; (c) detecting incorporation at a 3' end of the sequencing primer of one or more nucleotide triphosphates by a sequencing reaction byproduct if such one or more nucleotide triphosphates are complementary to corresponding nucleotides in the template nucleic acid; (d) washing unincorporated nucleotide triphosphates from the reaction chambers; and (e) repeating steps (b) through (d) until the plurality of template nucleic acids are sequenced. For embodiments where hydrogen ion is measured as a reaction byproduct, the reactions further should be conducted under weak buffer conditions, so that the maximum number of hydrogen ions reacts with a sensor and not extraneous components (e.g. microwell or solid supports that may have surface buffering capacity) or chemical constituents (in particular pH buffering compounds). In one embodiment, a weak buffer allows detection of a pH change of at least ±0.1 in said reaction chamber, or at least ±0.01 in said reaction chambers.

Several potential sources of noise may affect output signals from sensors when a large number of electrochemical reactions are carried out in a microwell array integrated with a sensor array, such as described by Rothberg et al (cited above). Such sources of noise include thermal sensitivity of the sensors, electrical potential disturbances in the fluid (such as resistive or thermal noise in the fluids, reference voltage changes due to different fluids contacting the reference electrode, and the like) and pH changes due to bulk changes in fluids that are passed over the sensor array (referred to herein as "reagent change noise"). Additional sources of noise may also arise in DNA sequencing applications from the nature of a particular DNA sequencing chemistry employed. For example, noise may arise due to the stochastic behavior of polymerase function (incomplete extensions) or failure to completely wash away all dNTPs in a given step (inappropriate incorporation), e.g. Chen et al, International patent publication WO/2007/098049.

Thermal sensitivity of a sensor array is addressed by maintaining the sensor array at a predetermined temperature that is suitable for extension reactions and that permits measurement of hydrogen ion concentrations or changes in the pH. In one aspect, such temperature is within the range of from 25° C. to 75° C. Preferably the predetermined temperature is constant throughout the entire multistep reaction. Such temperature may be regulated by conventional techniques, e.g. Peltier device, or the like. In one embodiment, temperature is maintained by controlling the temperature of the reagents that flow through the flow cell, such that the rate of flow and heat capacity of the fluid is sufficient to remove excess heat generated by the sensors or analytical reactions.

As mentioned above, disturbances in the reference voltage arise from a variety of sources, including changes in the type of fluid a reference electrode is in contact with, and noise from other components of the fluidics system. For example, other components of the fluidics system may act as antennas for extraneous electrical noise, e.g. 60 Hz noise, noise from power supplies, and the like, which affect the reference voltage. In accordance with the present teaching, a reference electrode is provided that contacts only one kind of reagent throughout a sequencing operation, thereby eliminating a component of reference voltage variability. In another aspect, low frequency noise introduced into the fluidics system may be reduced or eliminated by capacitively coupling the reference electrodes to other components of the fluidics system, such sections of reagent passages in the fluidic systems, as illustrated in FIGS. 7B and 7C.

Another source of noise may arise when successive reagent flows pass over a sensor array (i.e., reagent change noise). The magnitude of such noise depends on several factors including the nature of the measurement being made (e.g. pH, inorganic pyrophosphate (PPi), other ions, or the like) whether a leading or trailing reagent in a reagent change has a property or constituent, e.g. pH, which affects sensor performance and the magnitude of the influence, the relative magnitude of the reagent change effect in comparison with the reaction signal being monitored, and so on. For pH-based DNA sequencing applications (for example), pH-sensitive sensors may generate a signal in response to a reagent change in that is large in comparison to the signal due to hydrogen ion byproduct, as illustrated by the data of FIG. 6A. In such applications, different reagents, such as solutions containing different dNTPs, have slightly different buffering capacities and pKa's, so that at a boundary of different reagent flows, e.g. a wash solution flow followed by a dNTP flow, the sensors register a significant voltage change, as illustrated in FIGS. 2D and 6A. FIG. 6A shows the magnitudes of four output signals from different microwells of a DNA sequencing chip as disclosed is Rothberg et al (cited above), which employs conventional ion-sensitive field-effect transistor (ISFET) sensors. Curves (606) illustrate signals from microwells during a wash step with no changes in reagent. Curve (600) shows an output signal from a microwell containing a particle with template attached where a primer on the template has been extended by one nucleotide. Curve (602) is the output signal from a microwell that contains a particle with a template where there has been no extension. Region (604) is the difference between the two output signals ((602) and (604)) that is due to generation of hydrogen ion in the microwell where extension has taken place. Curve (608) in FIG. 6B, which is the difference between the values of curves (600) and (602), is the part of the raw output signal of curve (600) which is due to hydrogen ion produced in the extension reaction, i.e. the signal of interest. In accordance with the present teaching, such reagent change noise and other noise components common to local groups of microwells may be subtracted from an output signal of a selected sensor by using information from output signals generated from neighboring microwells. In one embodiment, such neighboring microwell information is obtained from at least one average value of output signals from a plurality of neighboring wells. In another embodiment, neighboring microwell information is obtained from output signals of empty wells. In still another embodiment, neighboring microwell information is obtained from output signals of non-empty microwells where no extension reaction took place. Correction of raw output signals by subtracting reagent change noise may be carried out after each reagent change based on averages computed after each such change, or such corrections may be carried out using averages computed from a previous reagent change, depending on the rate at which averages change during a multi-step or multi-cycle electrochemical process. For example, in a DNA sequencing embodiment, an average may be computed for each different dNTP flow in a cycle (where a succession of the four different dNTPs is introduced into reaction chambers) and used to correct raw output signals for from 1 to 5 cycles of reagent change.

As is noted from FIG. 2D, output signals from neighboring microwells may be systematically altered relative to signals from a microwell of interest depending on the type of neighboring microwells selected for noise subtraction. For example, in FIG. 2D, the same phenomena (e.g., signal delay) that permits the detection of empty wells, may also require that such signals must be transformed to account for such differences if subtraction from the signal of interest is going to make sense. For example, because the presence of a particle in the microwell of interest distorts the signal corresponding to reagent change (delay and flattening due to chemical interaction with the particle), an empty well signal must be modified to remove the changes due to the absence of a particle and chemical interactions, which may readily be done using conventional numerical analysis. If neighboring microwell information is restricted to only 0-mer neighbors, then such transformation is much less, or not necessary, in order to subtract reagent change noise from a signal of interest. As mentioned above, "an average" of neighboring microwell output signals may include weighted averages or transforms of the neighboring microwells' average output signals to reflect the different physical and chemical conditions of the selected microwell and its neighbors. Steps of an embodiment of such a process are illustrated in FIG. 6C. Raw output signal, $RS_i(j)$, for times j=1, 2 . . . t, recorded by a sensor of selected microwell, $M_i$, is read (660). "Raw output signal" means the recorded values of the output signal prior to data analysis. Neighboring microwells are defined (662) so that raw output signals of neighboring microwells, $RN_k(j)$, can also be read (664). Definitions of neighbors may include a local region from where neighbor signals are collected, for example, as described for FIGS. 5A-5C, and such definitions may include the types of neighboring microwells whose output signals are taken, e.g. empty wells, microwells with analyte or particle but no reaction, and the like. In one aspect, neighboring output signals are selected from neighboring microwells that are as physically and chemically similar to the Mi microwell, except for the presence of a signal, e.g. pH level, from the analyte that is to be detected or measured. After raw output signals from neighboring microwells are read, an average, $A(j)$, is computed (666) and subtracted (668) from raw output signal, $RSi(j)$, to give a noise-reduced output signal, $Si(j)$.

Figure 6E:
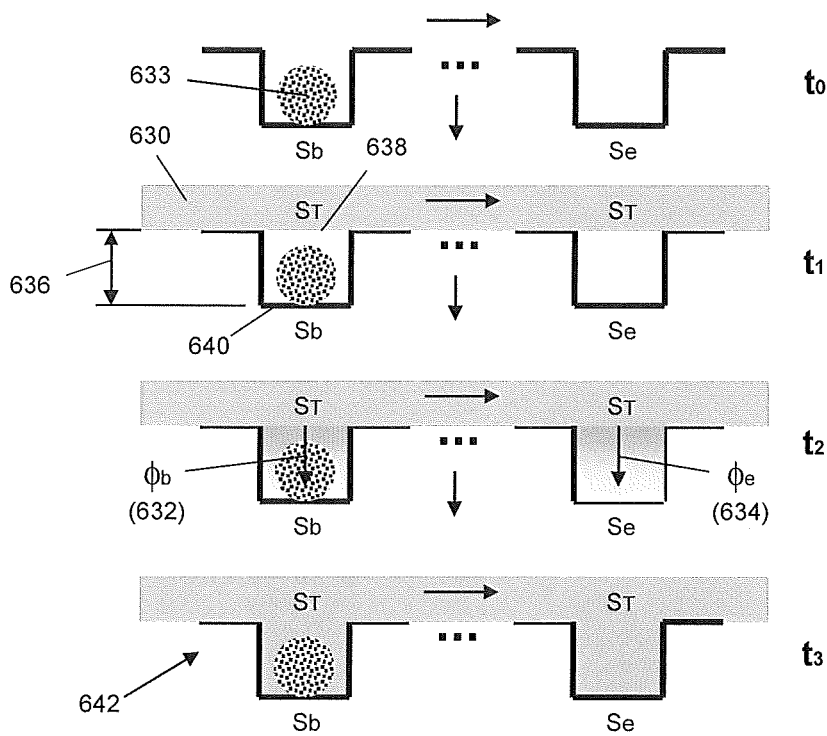
Figure 6F:
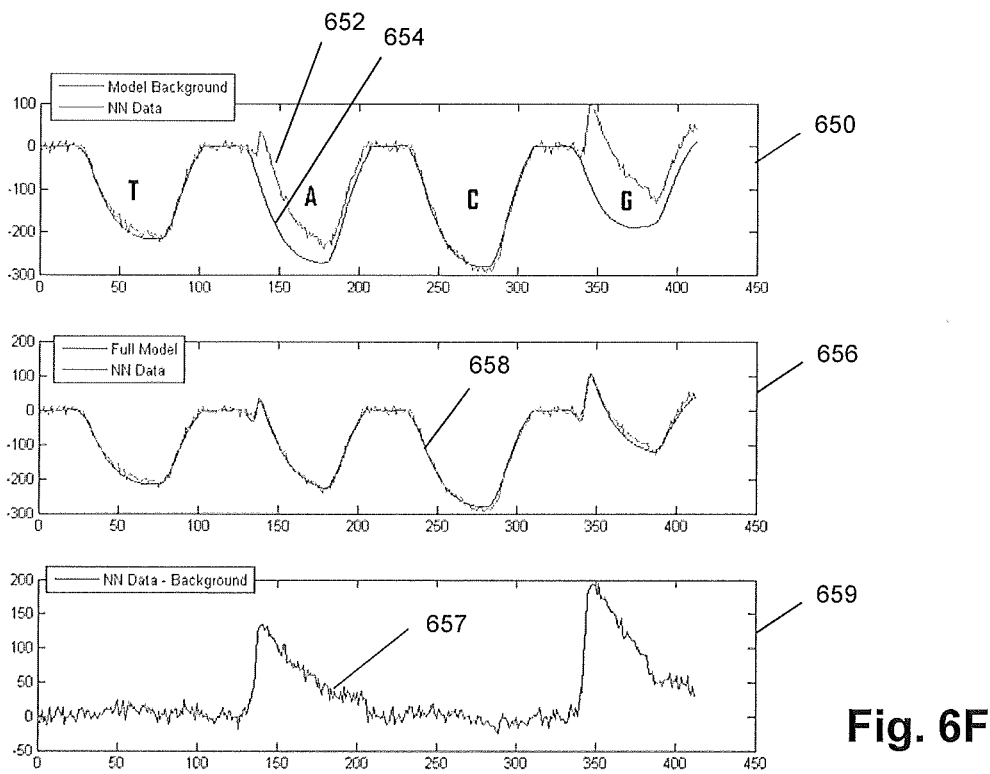

FIG. 6E illustrates another embodiment that uses an average neighbor signal to remove noise from a signal of interest (e.g. change in pH due to nucleotide incorporation). The figure shows two neighboring microwells (631) and (641) at four different times: before a next reagent is introduced ($t_0$), immediately after the next reagent is exposed to the microwells ($t_1$), a time during equilibration of the next reagent with the microwell contents ($t_2$), and after equilibrium has been achieved ($t_3$). The change in sensor signal due to such a reagent change is described as a two compartment model, where one compartment is the next reagent (e.g. the next flow of dNTPs) in region (638) adjacent to the opening of a microwell and the other compartment is the surface (640) at the bottom of a microwell adjacent to the sensor. Immediately after new reagent (630) enters a flow cell a concentration difference (636) is created between the two compartments, so that a flux of hydrogen ions is established both in microwells with particles $\phi_b$ (632) and in empty wells $\phi_c$ (634). For microwells having particles (633) where extension reactions occur, hydrogen ions are also created, which adds to the flux. Eventually equilibrium is reached (642) and the flux of hydrogen ions goes to zero. One of ordinary skill in the art would recognize that a variety of alternative models and models of differing complexity are available for describing the physical and chemical phenomena of the electrochemical reactions taking place in the microwells. Returning to the model of FIG. 6E, the generation of hydrogen ions by extension reactions and the fluxes through microwells with beads and those without may be described by simple reaction-diffusion equations, which give the change in hydrogen ion concentrations at the sensors, as illustrated by the following equations:

$$\frac{s_T - s_b}{\alpha_b} - \varphi_b - \frac{\delta s_b}{\delta t} B_b \quad \frac{s_T - s_e}{\alpha_e} - \varphi_e - \frac{\delta s_e}{\delta t} B_e$$

where $\alpha_b$ and $\alpha_e$ are diffusion constants of the hydrogen ions in the solvent, and $\beta_b$ and $\beta_c$ are constants that reflect the interaction (e.g. buffering) of the hydrogen ions with microwell wall or particle or analyte in the microwell. Manipulation of these terms and integration of the differentials gives $s_b$ as a function of $s_e$ and an integral of the differences between $s_b$ and $s_e$. To this expression is added a source term, $I_{ext}$, for the hydrogen ions generated in an extension reaction.

$$s_b = s_s R + \frac{\int s_e - s_b}{\tau_b} + I_{ext}$$

where $R = (\alpha_e \beta_e / \alpha_b \beta_b)$. Curves for $s_b$ are readily generated numerically for fitting data to remove reagent change noise. FIG. 6F illustrates data fit by such a model and use of the model to subtract reagent change noise. Panal (650) shows an output signal (652) ("NN Data") from a sensor of a microwell in which extension reactions occur when exposed to flows of dATP and dGTP. Curve (654) ("Model Background") is from the above model of the reagent change noise. Panel (656) shows curve (658) which models both the reagent change noise and the generation of hydrogen ions. Panel (659) shows output signal (657) after the reagent change noise has been subtracted.

In FIG. 6D, each template includes calibration sequence (685) that provides a known signal in response to the introduction of initial dNTPs. Preferably, calibration sequence (685) contains at least one of each kind of nucleotide. In one aspect, calibration sequence (685) is from 4 to 6 nucleotides in length and may contain a homopolymer or may be non-homopolymeric. Calibration sequence information from neighboring microwells may be used to determine which neighboring microwells contain templates capable of being extended which, in turn, allows identification of neighboring microwells that may generate 0-mer signals, 1-mer signals, and so on, in subsequent reaction cycles. Information from such signals from neighboring microwell may be used to subtract undesired noise components from output signals of interest. In other embodiments, an average 0-mer signal may be modeled (referred to herein as a "virtual 0-mer" signal) by taking into account (i) neighboring empty well output signals in a given cycle, and (ii) the effects of the presence of a particle or template on the shape of the reagent change noise curve. The latter factor as noted in FIG. 2D is a delay, which is reflected in a flattening and shifting in the positive time direction of an output signal of a particle-containing microwell relative to an output signal of an empty well. As noted, such effects are readily modeled to convert empty well output signals to virtual 0-mer output signals, which may be used to subtract reagent change noise.

Figure 7A:
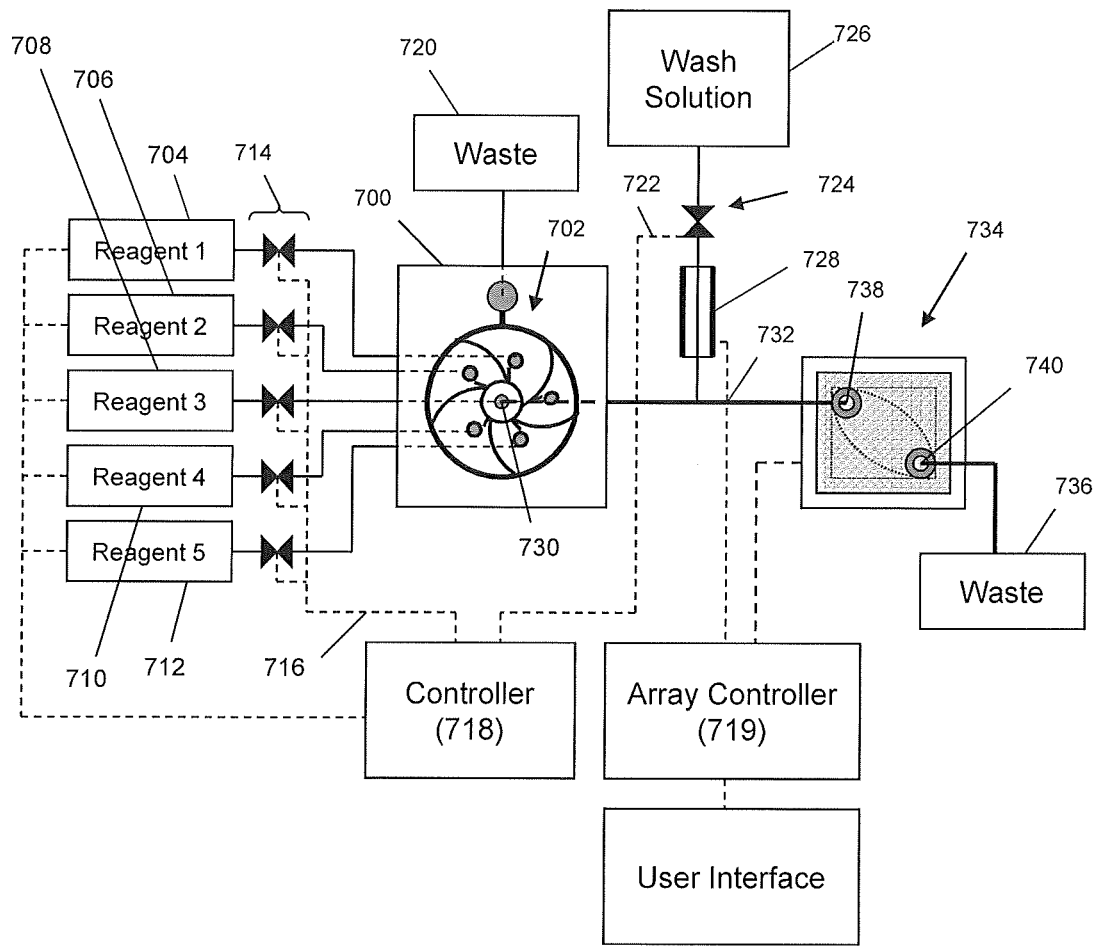
FIGS. 7A-7C are diagrammatic illustrations of components of an apparatus of the present teaching adapted for pH-based DNA sequencing.
Figure 7B:
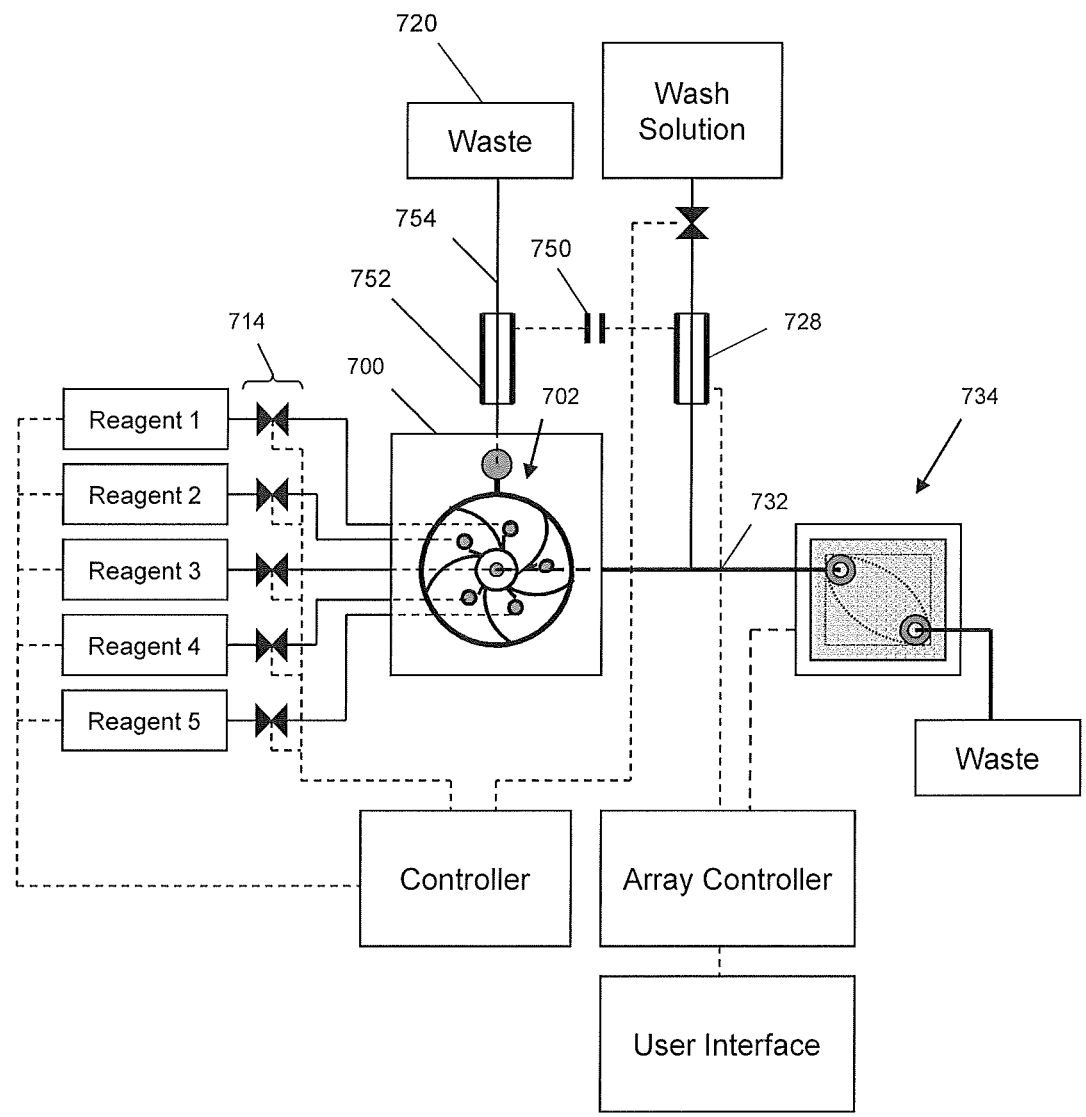
Figure 7C:
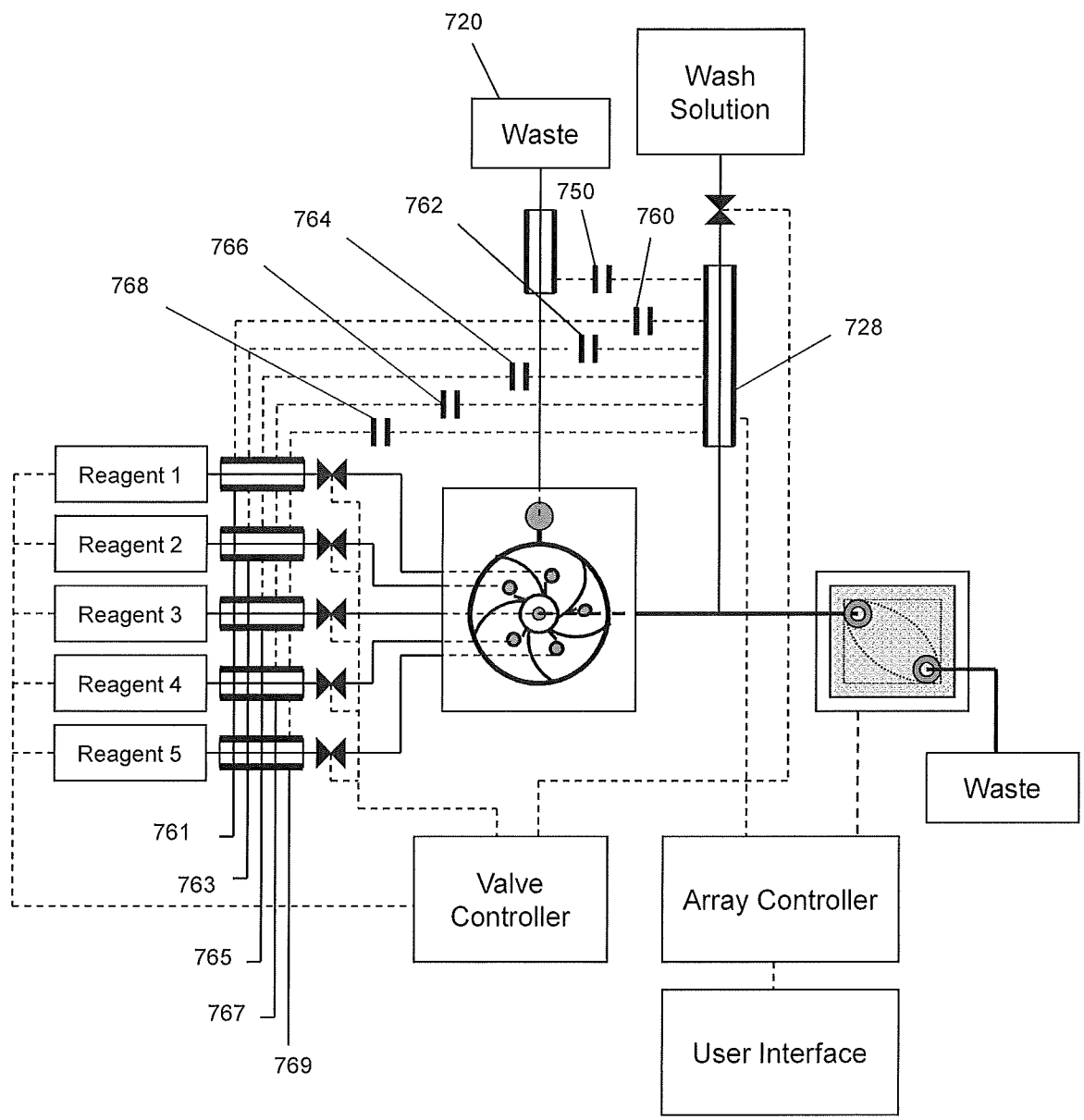

FIG. 7A diagrammatically illustrates an apparatus that may be used to carry out pH-based nucleic acid sequencing in accordance with Rothberg et al, U.S. patent publication 2009/0026082. Housing (700) containing fluidics circuit (702, described more fully below, e.g., an embodiment of a fluidic subsystem) is connected by inlets to reagent reservoirs (704, 706, 708, 710, and 712), to waste reservoir (720), and to flow cell (734) by passage (732) that connects fluidics node (730) to inlet (738) of flow cell (734). Reagents from reservoirs (704, 706, 708, 710, and 712) may be driven to fluidic circuit (702) by a variety of methods including pressure, pumps, such as syringe pumps, gravity feed, and the like, and are selected by control of valves (714). Controller (718) includes controllers for valves (714) that generate signals for opening and closing via electrical connection (716). Controller (718) also includes controllers for other components of the system, such as wash solution valve (724) connected thereto by (722). Array controller (719) (e.g., an embodiment of a computational circuitry) includes control and data acquisition functions for flow cell (734) and reference electrode (728). In one mode of operation, fluidic circuit (702) delivers a sequence of selected reagents (1, 2, 3, 4, or 5) to flow cell (734) under programmed control of controller (718), such that in between selected reagent flows fluidics circuit (702) is primed and washed, and flow cell (734) is washed. Fluids entering flow cell (734) exit through outlet (740) and are deposited in waste container (736). Throughout such an operation, the reactions or measurements taking place in flow cell (734) are assured a stable reference voltage because fluidics circuit (702) provides reference electrode (728) with a continuous, i.e. uninterrupted, electrolyte pathway with flow cell (734), although it is in physical contact with only the wash solution.

FIGS. 7B and 7C illustrate further measures that may be taken to reduce noise introduced into other parts of fluidics system that may affect the reference voltage. In FIG. 7B, electrode (752) forming part of waste stream (754) is coupled to reference electrode (728) by capacitor (750), which filters low frequency noise introduced through waste stream (754). Likewise, as shown in FIG. 7C, such electrodes (761, 763, 765, 767, and 769) may be fitted on flow paths for process reagents, such as reagents 1 through 5, and coupled to reference electrode (728) through separate capacitors (760, 762, 764, 766, and 768, respectively).

Sequencing Keys

In various embodiments, such as in the case of nucleic acid sequencing operations using the electrochemical detection system, a coding and identification system using sequencing keys may be implemented. In various embodiments, sequencing keys may be used to aid in the identification of or drive the separation of various nucleic acid fragments or segments under analysis (e.g. test fragments (TF's) and library fragments (Lib's)). Further sequencing keys may aid in resolving how the flow order determines the flow-space sequence.

| Default Sequencing Keys & Flow Order | | |
| --- | --- | --- |
| | Base-space | Flow order TACG vector |
| Library Key | TCAG | 1010010X |
| TF Key | ATCG | 0100101X |

The table above depicts default library and TF sequencing keys, both in base-space and in flow-space for the given default flow order TACG. The 'X' in the vector above indicates that the value is at least a one, but could be higher since the next base after the key could also match, thus creating a longer homopolymer.

Separation

In various embodiments, when particles/beads have been identified within the wells, separation may then be performed. In this exemplary operation, the two sequencing keys are used to compare each read. In those instances where a sample chamber or well is determined to contain a bead the flow may be converted into a sequence by testing against each key. In the examples shown, the test may be performed against both keys with the number of flows used to sequence each key determined, and the lower number of the two used. Such an approach may be desirable where adding more bases to one of the two keys may not necessarily result in better separation since the shorter of the two may drive the number of flows used.

In one exemplary embodiment, with the default keys & flow order above, two vectors are provided:
TACGTACG
1010010
0100101

Using this information one may attempt to identify valid comparison nucleotide pairs. In one aspect, a valid comparison nucleotide pair occurs where in order to compare two sequences, selected rules are satisfied. By way of example, two rules are shown below. In various embodiments, when both rules are satisfied for a given nucleotide, a separator 'event' to be identified. In various embodiments, identified 'events' improve the separation of the two keys:

1: Given a 0-mer and a 1-mer for the given nucleotide in the key

2: The 1-mer from one key may be firing during the 0-mer event in the other nucleotide.

Thus one may attempt to observe nucleotide pairs that are orthogonal in flow-space for the two keys, as in the bolded/undelined vertical highlighted pairs:

'T' nucleotide satisfies the above-described rules:
1010010
$\overline{0}100\overline{1}01$ Above, for the 'T' nucleotide flow, the library key incorporates on the first flow, and has a 0-mer on the second 'T' flow, whereas the TF key may comprises substantially the opposite.

A similar case may be observed for the 'A' nucleotide, and the 'C' nucleotide. In one exemplary embodiment, the 'G' nucleotide may remain unused since there is no 1-mer event observe until the 8th flow. In this case, that flow is not included since that 'G' in the library can be part of a larger homopolymer stretch. It may therefore be desirably to not include as there may not be a guarantee that one would have exactly a 1-mer in that flow. Further, the TF key does not have a 1-mer in the first 'G' flow, it has a 0-mer 'G' in the first 'G' flow which is substantially the same as the library key.

For the 'A' nucleotide the rules are satisfied:
1010010
$0\overline{1}001\overline{0}\overline{1}$ Likewise 'C' nucleotide satisfies the rules:
1010010
$01\overline{0}010\overline{1}$ Alternate Library Key Example In another exemplary embodiment and alternate library key, CTAGT is selected. Given a standard flow order of TACG, the flow-space vector may be defined as 00101101X. Comparing this vector against the TF vector one may observe how many separation events should be used.

Initially, the number of flows to be used is determined. In the example, the new library key sequences in 9 flows, the TF key in 8. Since the last base is unknown in each, 8 and 7 flows respectively are used, with 7 flows being the lower of the two. Again, 7 flows can be used to separate the two.

Testing the rules for each nucleotide one may observe how many separator events can be used, for example:

'T' nucleotide test would not pass under the specified rules (they both incorporate on the same flow)
0010110
$\overline{0}100\overline{1}01$ 'A' nucleotide test passes:
0010110
$0\overline{1}001\overline{0}\overline{1}$ 'C' nucleotide test passes:
0010110
$01\overline{0}010\overline{1}$ Based on this information two 'events' may be used for separating the two keys.

Flow Order

When altering the flow order, the same rules described above may be applied. In various embodiments, one difference is in the flow-space vectors that get formed. It will be appreciated that a sequencing analysis pipeline may be configured that supports arbitrary flow orders. For substantially any flow order, a form flow-space vector may be determined from the sequences. Following the exemplary/analogous nucleotide comparison rules above it may be observed whether there are sufficient separator 'events' in order to separate the beads into library and TF's. In general, it may be desirable to maintain two or more such events. In certain instances, three or more may be desirable. In various instances, it may be undesirable to provide too many flows in order to get 3 or 4 events (in the case of analysis for 4 different nucleotides 4 may be the maximum).

Fluidics Circuits for Sequential Reagent Delivery

Figures 8A, 8B:
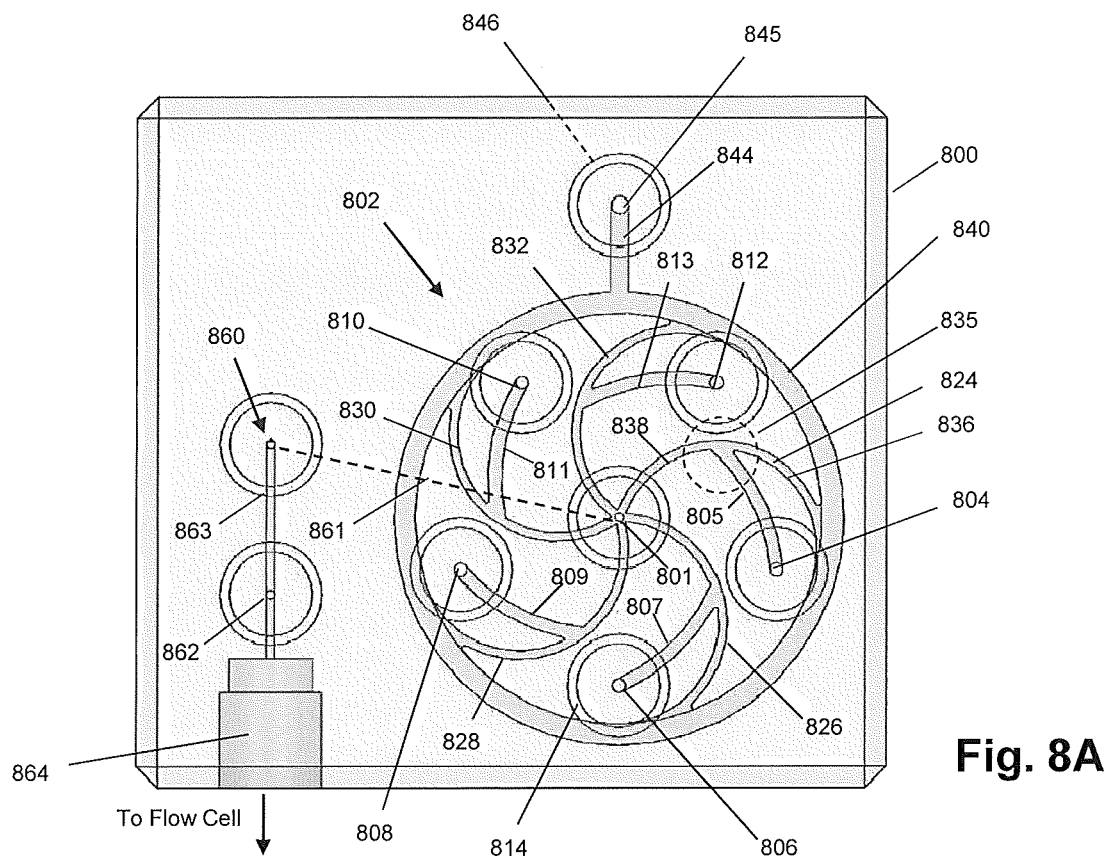
FIGS. 8A-8C diagrammatically illustrate a fluid circuit for delivering successively different reagents to a flow cell for DNA sequencing, where a reference electrode is in continuous fluid contact with solely a wash solution.
Figure 8C:
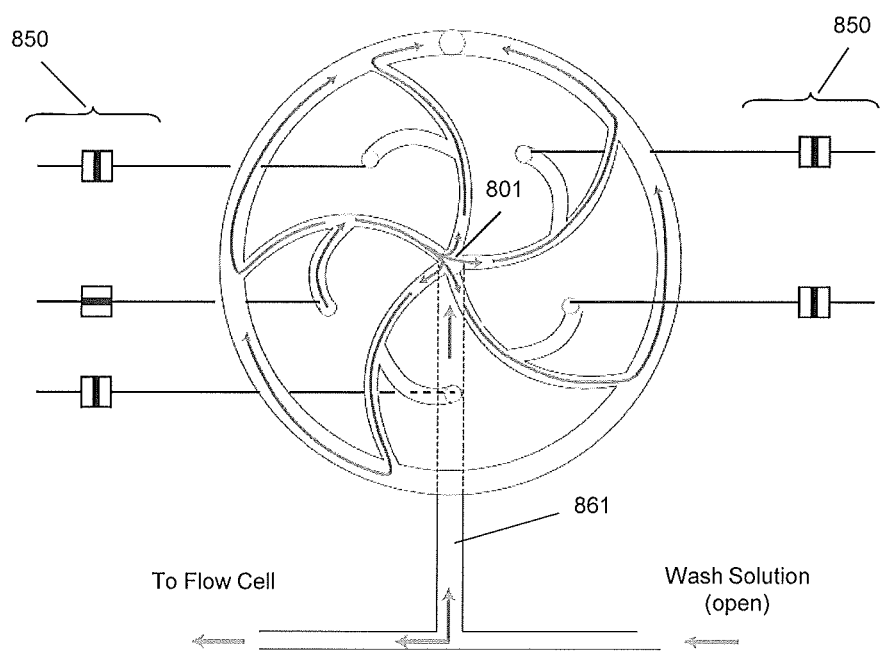

As mentioned above, in one embodiment, a reference electrode of the present teaching is kept in contact with only a single reagent by use of a fluidic circuit, such as (702) in FIG. 7A. FIGS. 8A-8C diagrammatically illustrate an embodiment of a fluidics circuit which provides this contact for the reference electrode and which accommodates five input reagents in a planar circuit structure. FIG. 8A is a top view of a transparent body or housing (800) containing fluidic circuit (802) which may comprise a microfluidics device. Housing (800) may be constructed from a variety of materials, including metals, glass, ceramics, plastics, or the like. Transparent materials include polycarbonate, polymethyl methacrylate, and the like. Inlets (or input ports) (804, 806, 808, 810, and 812) are connected by a passage to their respective connector slots (814) located on the bottom side of housing (800) (shown as double circles concentric with the inlets) from which reagents enter fluidic circuit (802). Inlets (804, 806, 808, 810, and 812) are in fluid communication with passages (805, 807, 809, 811, and 813, respectively) which, in turn, are connected to curvilinear passages (824, 826, 828, 830, and 832, respectively). Each curvilinear passage consists of two legs, such as (836) and (838), identified for curvilinear passage (824) at a "T" junction (835), also identified for only curvilinear passage (824). One leg is an inner leg (for example (838)) which connects its respective inlet to node (or multi-use central port) (801) and the other leg is an outer leg (for example (836)) which connects its respective inlet to waste passage (or ring) (840). As mentioned above, the cross-sectional areas and lengths of the inner and outer legs of the curvilinear passages may be selected to achieve the desired balance of flows at the "T" junctions and at node (801). Through passage (844), waste passage (or channel) (840) is in fluid communication with waste port (845) which connects to a waste reservoir (not shown) by connector slot (846) on the bottom side of body (800). Node (801) is in fluid communication with port (860) by passage (861) which in this embodiment is external to body (800) and is illustrated by a dashed line. In other embodiments, passage (861) may be formed in body (800) so that connector slots for node (801) and port (860) are not required. Port (860) is connected by passage (863) to wash solution inlet (862), where a "T" junction is formed, and to connector slot (864) which, in turn, provides a conduit to a flow cell, reaction chamber, or the like. FIGS. 8B and 8C illustrate two of three modes of using the fluidics circuit to distribute fluids to a flow cell. The modes of operation are implemented by valves (850) associated with each of the input reagents and with the wash solution. In a first mode of operation (selected reagent valve open, all other reagent valves closed, wash solution valve closed) (FIG. 8B), a selected reagent is delivered to a flow cell; in a second mode of operation (selected reagent valve open, all other reagent valves closed, wash solution valve open) (FIG. 8C), the fluidic circuit is primed to deliver a selected reagent; and in a third mode of operation (all reagent valves closed, wash solution valve open) (not shown), all passages in the fluidics circuit are washed. As mentioned above, associated with each inlet is a valve (850) which can be opened to allow fluid to enter fluidic circuit (802) through its respective inlet (as shown for valve (852)), or closed to prevent fluid from entering circuit (802) (as shown with all valves, except for (852)). In each case, when an inlet's valve is open and the others are closed (including the wash solution valve) as shown for inlet (870) in the FIG. 8B, fluid flows through passage (854) to "T" junction (856) where it is split into two flows, one of which is directed to waste passage (840) and then the waste port (845), and another of which is directed to node (801). From node (801) this second flow again splits into multiple flows, one of which exits node (801) through passage (861) and then to passage (863) and to a flow cell, and the other flows to each of the passages connecting node (801) to the other inlets, and then to waste passage (840) and waste port (845). The latter flows pass the other inlets carrying any material diffusing or leaking therefrom and directing it to waste port (845). A sequence of different reagents may be directed to a flow cell by opening the valve of a selected reagent and simultaneously closing the valves of all of the non-selected reagents and the wash solution. In one embodiment, such sequence may be implemented by a sequence of operating modes of the fluidics circuit such as: wash, prime reagent $x_1$, deliver reagent $x_1$, wash, prime reagent $x_2$, deliver reagent $x_2$, wash, and so on. The reagent priming mode of operation is illustrated in FIG. 8C. As in the reagent delivery mode, all reagent inlet valves are closed, except for the valve corresponding to the selected reagent. Unlike the reagent delivery mode, however, the wash solution valve is open and the relative pressure of the selected reagent flow and the wash solution flow is selected so that wash solution flows through passage (861) and into node (801) where it then exits through all the passages leading to waste passage (840), except for the passage leading to the selected reagent inlet.

Instrumentation Systems/Electronics & Software
Frame Averaging & Compression

In various embodiments, it may be desirable to provide mechanisms for efficient data storage and analysis using the electrochemical detection system. Oftentimes, such systems are capable of generating large amounts of information and there is a desire to reduce raw data size where possible. In various embodiments, the below-described forms of compression may be used. These compression routines may further be combined or used independently or in connection with other data processing routines. The first approach may comprise a frame averaging methodology. Frame averaging may used as a form of compression capable of reducing the overall data size. Frame averaging may further include both lossless and lossy compression. Lossy compression algorithms such as MP2 or MP4 as used in the video and DVD industry may be used in connection with the data obtained from the electrochemical sensor. In various embodiments, data acquisition from the sensor array may be taken as time slices or intervals. In one aspect, such an approach may provide a 2D array of pixels captured multiple times per time interval (e.g. multiple times per second). Such an approach may be analogous to that of obtaining information in the format of raw digital video. Data obtained in this manner can be processed utilizing lossless compression techniques including keyframe/delta compression. Lossy compression algorithms such as MP4 may also be applied. Further, it will be appreciated that one may utilize custom compression algorithms developed to leverage specific knowledge of the character of the data (e.g. biology-based data or samples) and instrument fluidics.

The discussion below provides details of one exemplary data compression approach that may be applied to the present teachings. There are opportunities both on the FPGA and on the CPU where one or more compression algorithms can be used.

Frame Averaging—FPGA & CPU

In various embodiments, frame averaging may be applied as an approach whereby two or more pixel measurements in successive frames are averaged together for each pixel of every frame considered. The output may be taken as the average measurement for each pixel of all frames. In this style of compression, a gain of a reduction in noise by averaging two or more sampled frames together (per pixel) may be realized. Frame averaging may be configured to occur on both the FPGA and on the CPU. In performing frame averaging on the FPGA side, one may make effective use of available RAM, a limited resource, and thus provide a mechanism to facilitate faster imaging and in various embodiments to image longer. Additional frame averaging on the CPU may be used to reduce noise as well as manage the data rate for streaming to storage (e.g. a hard drive) and over data transmission routes (e.g. Ethernet) to external file servers.

Variable Frame Rate Frame Averaging—FPGA & CPU

In various embodiments, variable frame rate averaging may be used as an approach similar to frame averaging discussed above with the additional feature allowing use of a variable number of frames to be averaged together. The number of frames averaged and output to a single frame can be done at any point during the acquisition. In certain instances such averaging may be desirable configured to occur to enhance or maximize the signal focused around events of interest (e.g. the biological event being detected). For example, in nucleic sequencing operations, during the incorporation event itself, it may be desirable to capture the shape of that curve over the measurement interval. However, before the incorporation event, it may be more desirable beneficial to average frames together to reduce noise. Signal obtained during this time interval may also not be as much of interest (e.g. generally a flatline measurement prior to the incorporation). After the incorporation, while the measured signal may follow a normal decay pattern, it may then acceptable to average more frames together to reduce noise without losing the information about the incorporation event being measured.

Keyframe Delta Compression—FGPA & CPU

In still other embodiments, Keyframe/Delta compression may be used where an initial measurement per pixel may be stored in the first frame as normal, using for example 16 bits. For subsequent frames, each pixel may be compared with the 'keyframe' value, and the difference or delta value stored using 8 bits. This process may continue until a pixel cannot be stored using 8 bits, at which point a new keyframe value is stored with 16 bits. New pixel values are compared against the most recent keyframe. This compression step can occur after any frame averaging, or directly from the raw data. Such an algorithm may be performed on either the FPGA or the CPU.

Lossy Compression—CPU

In various embodiments, when considering the acquisition data contains multiple frames in time, each frame contains measurement information per pixel. Utilizing compression routines such as MP4 allows the data to be highly compressed without losing the information contained therein. Such algorithms can be implemented on the CPU and elsewhere and can be combined as a last step with other data modifications used earlier.

DEFINITIONS

"Amplicon" means the product of a polynucleotide amplification reaction; that is, a clonal population of polynucleotides, which may be single stranded or double stranded, which are replicated from one or more starting sequences. The one or more starting sequences may be one or more copies of the same sequence, or they may be a mixture of different sequences that contain a common region that is amplified, for example, a specific exon sequence present in a mixture of DNA fragments extracted from a sample. Preferably, amplicons are formed by the amplification of a single starting sequence. Amplicons may be produced by a variety of amplification reactions whose products comprise replicates of the one or more starting, or target, nucleic acids. In one aspect, amplification reactions producing amplicons are "template-driven" in that base pairing of reactants, either nucleotides or oligonucleotides, have complements in a template polynucleotide that are required for the creation of reaction products. In one aspect, template-driven reactions are primer extensions with a nucleic acid polymerase or oligonucleotide ligations with a nucleic acid ligase. Such reactions include, but are not limited to, polymerase chain reactions (PCRs), linear polymerase reactions, nucleic acid sequence-based amplifications (NASBAs), rolling circle amplifications, and the like. In one aspect, amplicons of the present teaching are produced by PCRs. As used herein, the term "amplifying" means performing an amplification reaction. A "reaction mixture" means a solution containing all the necessary reactants for performing a reaction, which may include, but not be limited to, buffering agents to maintain pH at a selected level during a reaction, salts, co-factors, scavengers, and the like. A "solid phase amplicon" means a solid phase support, such as a particle or bead, having attached a clonal population of nucleic acid sequences, which may have been produced by a process such as emulsion PCR, or like technique.

"Analyte" means a molecule or biological cell of interest that directly affects an electronic sensor at a sample retaining region, such as a microwell, or that indirectly affects such an electronic sensor by a byproduct from a reaction involving such molecule or biological cell located in such a sample retaining region, or reaction confinement region, such as a microwell. In one aspect, analyte is a nucleic acid template that is subjected to a sequencing reaction which, in turn, generates a reaction byproduct, such as hydrogen ions, that affects an electronic sensor. The term "analyte" also comprehends multiple copies of analytes, such as proteins, peptide, nucleic acids, or the like, attached to solid supports, such as beads or particles. In a one embodiment, the term "analyte" means a nucleic acid amplicon or a solid phase amplicon.

"Microfluidics device" means an integrated system of one or more chambers, ports, and channels that are interconnected and in fluid communication and designed for carrying out an analytical reaction or process, either alone or in cooperation with an appliance or instrument that provides support functions, such as sample introduction, fluid or reagent driving means, temperature control, detection systems, data collection or integration systems, and the like. Microfluidics devices may further include valves, pumps, and specialized functional coatings on interior walls, e.g. to prevent adsorption of sample components or reactants, facilitate reagent movement by electroosmosis, or the like. Such devices are usually fabricated in or as a solid substrate, which may be glass, plastic, or other solid polymeric materials, and typically have a planar format for ease of detecting and monitoring sample and reagent movement, especially via optical or electrochemical methods. Features of a microfluidic device usually have cross-sectional dimensions of less than a few hundred square micrometers and passages typically have capillary dimensions, e.g. having maximal cross-sectional dimensions of from about 500 µm to about 0.1 µm. Microfluidics devices typically have volume capacities in the range of from 1 µL to a few nL, e.g. 10-100 nL.

"Microwell," which is used interchangeably with "reaction chamber," means a special case of a "reaction confinement region," that is, a physical or chemical attribute of a solid substrate that permit the localization of a reaction of interest. Reaction confinement regions may be a discrete region of a surface of a substrate that specifically binds an analyte of interest, such as a discrete region with oligonucleotides or antibodies covalently linked to such surface. Usually reaction confinement regions are hollows or wells having well-defined shapes and volumes which are manufactured into a substrate. These latter types of reaction confinement regions are referred to herein as microwells or reaction chambers, and may be fabricated using conventional microfabrication techniques. Preferable configurations (e.g. spacing, shape and volumes) of microwells or reaction chambers are disclosed in Rothberg et al, U.S. patent publication 2009/0127589; Rothberg et al, U.K. patent application GB24611127, which are incorporated by reference. Microwells may have square, rectangular, or octagonal cross sections and be arranged as a rectilinear array on a surface. Microwells may also have hexagonal cross sections and be arranged as a hexagonal array, which permit a higher density of microwells per unit area in comparison to rectilinear arrays. Exemplary configurations of microwells are as follows: In some embodiments, the reaction chamber array comprises $10^2$, $10^3$, $10^4$, $10^5$, $10^6$ or $10^7$ reaction chambers. As used herein, an array is a planar arrangement of elements such as sensors or wells. The array may be one or two dimensional. A one dimensional array is an array having one column (or row) of elements in the first dimension and a plurality of columns (or rows) in the second dimension. The number of columns (or rows) in the first and second dimensions may or may not be the same. Preferably, the array comprises at least 100,000 chambers. Preferably, each reaction chamber has a horizontal width and a vertical depth that has an aspect ratio of about 1:1 or less. Preferably, the pitch between the reaction chambers is no more than about 10 microns. Briefly, in one embodiment microwell arrays may be fabricated as follows: After the semiconductor structures of a sensor array are formed, the microwell structure is applied to such structure on the semiconductor die. That is, the microwell structure can be formed right on the die or it may be formed separately and then mounted onto the die, either approach being acceptable. To form the microwell structure on the die, various processes may be used. For example, the entire die may be spin-coated with, for example, a negative photoresist such as Microchem's SU-8 2015 or a positive resist/polyimide such as HD Microsystems HD8820, to the desired height of the microwells. The desired height of the wells (e.g., about 3-12 μm in the example of one pixel per well, though not so limited as a general matter) in the photoresist layer(s) can be achieved by spinning the appropriate resist at predetermined rates (which can be found by reference to the literature and manufacturer specifications, or empirically), in one or more layers. (Well height typically may be selected in correspondence with the lateral dimension of the sensor pixel, preferably for a nominal 1:1-1.5:1 aspect ratio, height:width or diameter.) Alternatively, multiple layers of different photoresists may be applied or another form of dielectric material may be deposited. Various types of chemical vapor deposition may also be used to build up a layer of materials suitable for microwell formation therein. In one embodiment, microwells are formed in a layer of tetra-me-thyl-ortho-silicate (TEOS). The present teaching encompasses an apparatus comprising at least one two-dimensional array of reaction chambers, wherein each reaction chamber is coupled to a chemically-sensitive field effect transistor ("chemFET") and each reaction chamber is no greater than 10 $\mu m^3$ (i.e., 1 pL) in volume. Preferably, each reaction chamber is no greater than 0.34 pL, and more preferably no greater than 0.096 pL or even 0.012 pL in volume. A reaction chamber can optionally be $2^2$, $3^2$, $4^2$, $5^2$, $6^2$, $7^2$, $8^2$, $9^2$, or $10^2$ square microns in cross-sectional area at the top. Preferably, the array has at least $10^2$, $10^3$, $10^4$, $10^5$, $10^6$, $10^7$, $10^8$, $10^9$, or more reaction chambers. The reaction chambers may be capacitively coupled to the chemFETs, and preferably are capacitively coupled to the chemFETs.

"Primer" means an oligonucleotide, either natural or synthetic that is capable, upon forming a duplex with a polynucleotide template, of acting as a point of initiation of nucleic acid synthesis and being extended from its 3' end along the template so that an extended duplex is formed. Extension of a primer is usually carried out with a nucleic acid polymerase, such as a DNA or RNA polymerase. The sequence of nucleotides added in the extension process is determined by the sequence of the template polynucleotide. Usually primers are extended by a DNA polymerase. Primers usually have a length in the range of from 14 to 40 nucleotides, or in the range of from 18 to 36 nucleotides. Primers are employed in a variety of nucleic amplification reactions, for example, linear amplification reactions using a single primer, or polymerase chain reactions, employing two or more primers.

In a first aspect, a system includes a communication interface to communicatively couple to a sensor cartridge, a fluidic subsystem to exchange a reagent solution with the sensor cartridge, and a computational circuitry communicatively coupled to the communication interface and the fluidic subsystem. The computation circuitry is to monitor a sensor signal of a sensor of the sensor cartridge, detect a leak based on the sensor signal, and control fluid flow of the fluidic subsystem in response to detecting.

In an example of the first aspect, the sensor cartridge includes a sensor exposed to the reagent solution. In another example of the first aspect, the sensor cartridge includes an array of sensors, the sensor being of the array of sensors. For example, the sensor is a reference sensor of the array of sensors.

In a further example of the first aspect, the sensor is an ion sensitive sensor. In an additional example of the first aspect, the sensor is a temperature sensor.

In another example of the first aspect, the computational circuitry is to detect the leak based on a loss of the sensor signal. In a further example of the first aspect, the computational circuitry is to detect the leak based on a change in characteristic of the sensor signal. For example, the change in characteristic is a change in noise, such as line noise. In another example, the change in characteristic is a change in value beyond a threshold.

In an additional example of the first aspect, the system further includes a setting to receive the sensor cartridge in alignment with the communication interface.

In a further example of the first aspect, the fluidic subsystem includes a manifold having fluid ports to engage the sensor cartridge. In another example of the first aspect, the system further includes a user interface to provide an override option to a user.

In a second aspect, a method of controlling a system includes establishing communicative coupling between a communication interface and a sensor cartridge, establishing fluid communication between a fluidic subsystem and a sensor cartridge, monitoring a sensor signal of the sensor cartridge via the communication interface, detecting a leak based on a characteristic of the sensor signal, and controlling fluid flow of the fluidic subsystem in response to detecting the leak.

In an example of the second aspect, the characteristic is noise and wherein detecting a leak includes detecting an increase in noise, such as line noise or crosstalk from another sensor signal. In another example of the second aspect, detecting includes detecting a loss of the sensor signal. In a further example of the second aspect, the characteristic is a value, wherein detecting the leak includes detecting a value beyond a threshold.

In a third aspect, a computer readable medium includes non-transitory computer operable instructions operable by a computational circuitry to perform a method comprising monitoring a sensor signal of a sensor cartridge via a communication interface. The sensor cartridge is communicatively coupled to the communication interface and in fluid communication with a fluid subsystem. The method further includes detecting a leak based on a characteristic of the sensor signal and controlling fluid flow of the fluidic subsystem in response to detecting the leak.

Note that not all of the activities described above in the general description or the examples are required, that a portion of a specific activity may not be required, and that one or more further activities may be performed in addition to those described. Still further, the order in which activities are listed are not necessarily the order in which they are performed.

In the foregoing specification, the concepts have been described with reference to specific embodiments. However, one of ordinary skill in the art appreciates that various modifications and changes can be made without departing from the scope of the invention as set forth in the claims below. Accordingly, the specification and figures are to be regarded in an illustrative rather than a restrictive sense, and all such modifications are intended to be included within the scope of invention.

As used herein, the terms "comprises," "comprising," "includes," "including," "has," "having" or any other variation thereof, are intended to cover a non-exclusive inclusion. For example, a process, method, article, or apparatus that comprises a list of features is not necessarily limited only to those features but may include other features not expressly listed or inherent to such process, method, article, or apparatus. Further, unless expressly stated to the contrary, "or" refers to an inclusive-or and not to an exclusive-or. For example, a condition A or B is satisfied by any one of the following: A is true (or present) and B is false (or not present), A is false (or not present) and B is true (or present), and both A and B are true (or present).

Also, the use of "a" or "an" are employed to describe elements and components described herein. This is done merely for convenience and to give a general sense of the scope of the invention. This description should be read to include one or at least one and the singular also includes the plural unless it is obvious that it is meant otherwise.

Benefits, other advantages, and solutions to problems have been described above with regard to specific embodiments. However, the benefits, advantages, solutions to problems, and any feature(s) that may cause any benefit, advantage, or solution to occur or become more pronounced are not to be construed as a critical, required, or essential feature of any or all the claims.

After reading the specification, skilled artisans will appreciate that certain features are, for clarity, described herein in the context of separate embodiments, may also be provided in combination in a single embodiment. Conversely, various features that are, for brevity, described in the context of a single embodiment, may also be provided separately or in any subcombination. Further, references to values stated in ranges include each and every value within that range.

What is claimed is:

1. A system comprising:
    a communication interface to communicatively couple to a sensor cartridge;
    a fluidic subsystem to exchange a reagent solution with the sensor cartridge; and
    a computational circuitry communicatively coupled to the communication interface and the fluidic subsystem;
    wherein the computation circuitry is to monitor a sensor signal of a sensor of the sensor cartridge, detect a leak based on the sensor signal, and control fluid flow of the fluidic subsystem in response to detecting.

2. The system of claim 1, wherein the sensor cartridge includes a sensor exposed to the reagent solution.

3. The system of claim 1, wherein the sensor cartridge includes an array of sensors, the sensor being of the array of sensors.

4. The system of claim 3, wherein the sensor is a reference sensor of the array of sensors.

5. The system of claim 1, wherein the sensor is an ion sensitive sensor.

6. The system of claim 1, wherein the sensor is a temperature sensor.

7. The system of claim 1, wherein the computational circuitry is to detect the leak based on a loss of the sensor signal.

8. The system of claim 1, wherein the computational circuitry is to detect the leak based on a change in characteristic of the sensor signal.

9. The system of claim 8, wherein the change in characteristic is a change in noise.

10. The system of claim 9, wherein the noise is line noise.

11. The system of claim 8, wherein the change in characteristic is a change in value beyond a threshold.

12. The system of claim 1, further comprising a setting to receive the sensor cartridge in alignment with the communication interface.

13. The system of claim 1, wherein the fluidic subsystem includes a manifold having fluid ports to engage the sensor cartridge.

14. The system of claim 1, further comprising a user interface to provide an override option to a user.

15. A method of controlling a system, the method comprising:
    establishing communicative coupling between a communication interface and a sensor cartridge;
    establishing fluid communication between a fluidic subsystem and a sensor cartridge;
    monitoring a sensor signal of the sensor cartridge via the communication interface;
    detecting a leak based on a characteristic of the sensor signal; and
    controlling fluid flow of the fluidic subsystem in response to detecting the leak.

16. The method of claim 15, wherein the characteristic is noise and wherein detecting a leak includes detecting an increase in noise.

17. The method of claim 16, wherein the noise includes line noise.

18. The method of claim 16, wherein the noise includes crosstalk from another sensor signal.

19. The method of claim 15, wherein detecting includes detecting a loss of the sensor signal.

20. The method of claim 15, wherein the characteristic is a value, and wherein detecting the leak includes detecting a value beyond a threshold.

21. A computer readable medium comprising non-transitory computer operable instructions operable by a computational circuitry to perform a method comprising:
    monitoring a sensor signal of a sensor cartridge via a communication interface, the sensor cartridge communicatively coupled to the communication interface and in fluid communication with a fluid subsystem;
    detecting a leak based on a characteristic of the sensor signal; and
    controlling fluid flow of the fluidic subsystem in response to detecting the leak.

* * * * *